United States Patent
Liang et al.

(10) Patent No.: US 11,834,675 B2
(45) Date of Patent: Dec. 5, 2023

(54) T LYMPHOCYTE PRODUCTION METHODS AND T LYMPHOCYTES PRODUCED THEREBY

(71) Applicant: CELGENE CORPORATION, Summit, NJ (US)

(72) Inventors: Bitao Liang, Closter, NJ (US); Xiaohua Lu, Monmouth Junction, NJ (US); Wei Liu, Bridgewater, NJ (US); Kathy E. Karasciewicz-Mendez, Hillsborough, NJ (US); Christopher Wiwi, Basking Ridge, NJ (US); Kruti Shah, Piscataway, NJ (US)

(73) Assignee: CELGENE CORPORATION, Summit, NJ (US)

( * ) Notice: Subject to any disclaimer, the term of this patent is extended or adjusted under 35 U.S.C. 154(b) by 1282 days.

(21) Appl. No.: 16/067,536

(22) PCT Filed: Dec. 29, 2016

(86) PCT No.: PCT/US2016/069269
§ 371 (c)(1),
(2) Date: Jun. 29, 2018

(87) PCT Pub. No.: WO2017/117418
PCT Pub. Date: Jul. 6, 2017

(65) Prior Publication Data
US 2021/0163890 A1      Jun. 3, 2021

Related U.S. Application Data

(60) Provisional application No. 62/272,969, filed on Dec. 30, 2015.

(51) Int. Cl.
| | | |
|---|---|---|
| *C12N 5/0783* | (2010.01) | |
| *A61K 39/00* | (2006.01) | |
| *A61K 35/17* | (2015.01) | |
| *C07K 16/28* | (2006.01) | |

(52) U.S. Cl.
CPC ............ *C12N 5/0636* (2013.01); *A61K 35/17* (2013.01); *A61K 39/0011* (2013.01); *C07K 16/2818* (2013.01); *C07K 16/2827* (2013.01); *C12N 2501/2304* (2013.01); *C12N 2501/2307* (2013.01); *C12N 2501/2315* (2013.01)

(58) Field of Classification Search
None
See application file for complete search history.

(56) References Cited

U.S. PATENT DOCUMENTS

| | | | |
|---|---|---|---|
| 7,498,171 B2 | 3/2009 | Hariri et al. | |
| 2003/0082806 A1 | 5/2003 | Berenson et al. | |
| 2008/0031900 A1 | 2/2008 | Palucka et al. | |
| 2009/0136531 A1* | 5/2009 | Nakagawa | C12N 7/00 514/44 R |
| 2010/0189728 A1* | 7/2010 | Schendel | C12N 5/0636 435/325 |
| 2014/0112956 A1 | 4/2014 | Karlsson-Parra et al. | |
| 2014/0322214 A1 | 10/2014 | Banchereau et al. | |

FOREIGN PATENT DOCUMENTS

| | | | |
|---|---|---|---|
| CN | 103502439 A | 1/2014 | |
| CN | 104 946 588 | 9/2015 | |
| CN | 105 025 924 | 11/2015 | |
| WO | WO 1996/05309 | 2/1996 | |
| WO | WO 1998/33888 | 8/1998 | |
| WO | WO 2012/140130 | 10/2012 | |
| WO | WO-2015009604 A1 * | 1/2015 | ............ A61K 35/17 |

OTHER PUBLICATIONS

Pattacini et al., 2014, J. Virol. Meth. vol. 199: 17-24.*
Tan et al., 2002, J. Exp. Med. vol. 195: 1523-1532.*
Vera et al., 2010, J. Immunother. vol. 33: 305-315.*
Vella et al., 1998, PNAS. vol. 95: 3810-3815.*
Wu et al., 2010, Vir. J. vol. 7: 1-7.*
Schluns et al., 2003, Nat. Rev. vol. 3: 269-279.*
Gerdemann et al., "Rapidly generated multivirus-specific cytotoxic T lymphocytes for the prophylaxis and treatment of viral infections," Mol Ther (2012) 20(8):1622-1632.
Manzo et al., "Antigen-specific T cell therapies for cancer," Human Mol Gene (2015) 24(R1):R67-R73.
Ramos et al., "Human Papillomavirus Type 16 E6/E7 Specific Cytotoxic T Lymphocytes for Adoptive Immunotherapy of HPV Associated Malignancies," J Immunother (2013) 36(1):66-76.
Oxenius et al., "CpG-containing oligonucleotides are efficient adjuvants for induction of protective antiviral immune responses with T-cell peptide vaccines," J Virol. (1999) 73(5): 4120-6.

\* cited by examiner

*Primary Examiner* — Amy E Juedes
(74) *Attorney, Agent, or Firm* — MORRISON & FOERSTER LLP

(57) ABSTRACT

Provided herein are methods of generating T cells, e.g., cytotoxic T lymphocytes starting from peripheral blood mononuclear cells without a separate step of generating and isolating antigen-presenting cells, and with a single round of antigen stimulation. Also provided herein are methods of using said cytotoxic T lymphocytes, for example, to treat cancer and/or viral infection.

25 Claims, 32 Drawing Sheets

T LYMPHOCYTE PRODUCTION METHODS AND T LYMPHOCYTES PRODUCED THEREBY

Figure 1:
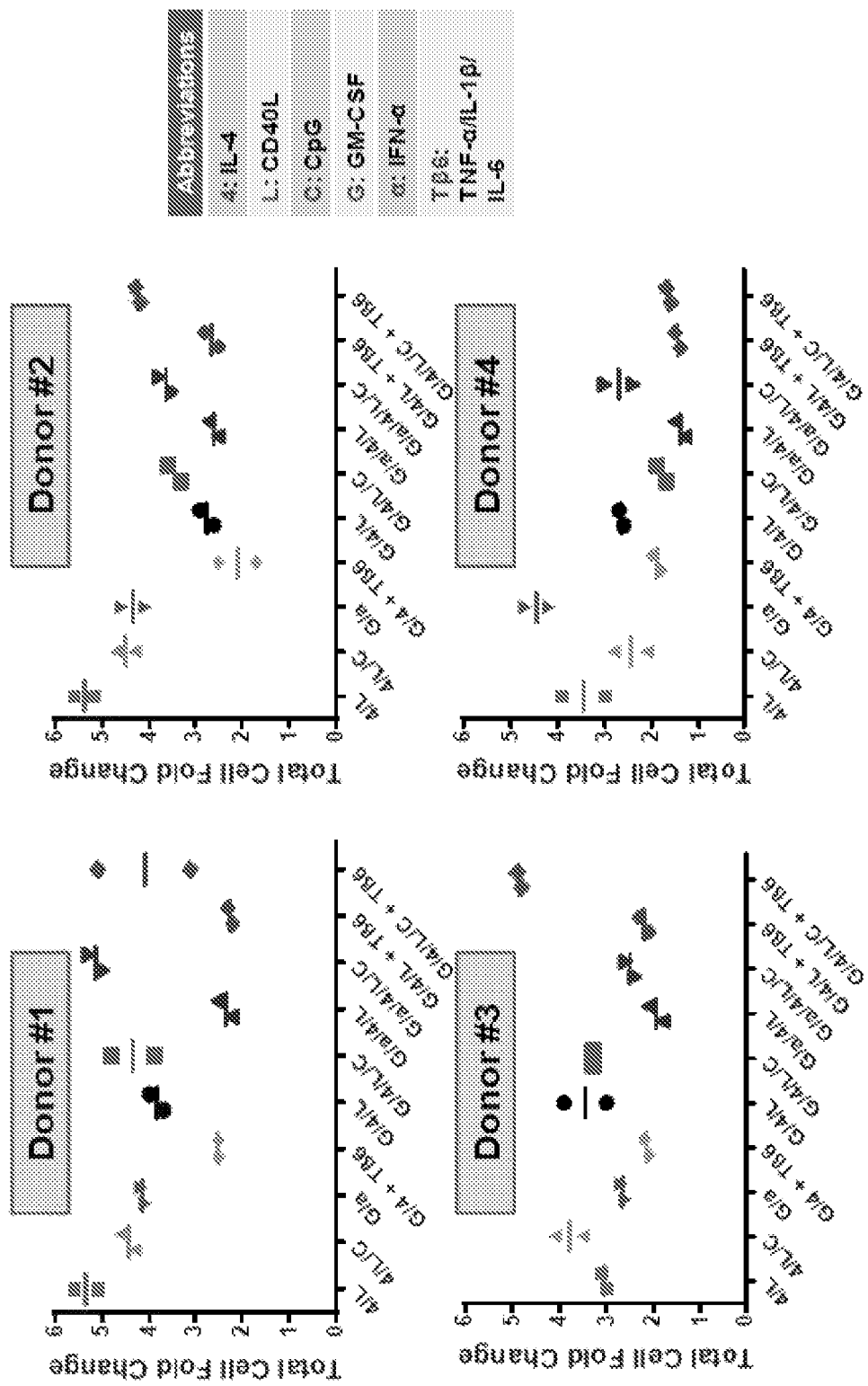

This application is a U.S. National Stage Application of International Patent Application No. PCT/US2016/069269, filed Dec. 29, 2016, which claims the benefit of U.S. Provisional Patent Application No. 62/272,969, filed Dec. 30, 2015, each of which is incorporated by reference herein in its entirety.

1. FIELD

The disclosure herein relates to the field of immunology, and more specifically, to the generation of antigen-specific T lymphocytes and methods of use thereof.

2. BACKGROUND

Generation of antigen-specific T cells, e.g., cytotoxic T lymphocytes (CTLs) ex vivo involves T cell antigen-specific activation followed, e.g., by T cell proliferation. Full activation of such T cells involves ligation of T cell receptor (TCR) with cognate MHC-peptide complexes presented by antigen presenting cells (APC), including dendritic cells (DC), macrophages, and B cells, and ligations of co-stimulatory molecules between T cells and APC. Sometimes, cell-free MHC-peptide complexes are used in lieu of MHC-peptide complexes presented by APCs. If co-stimulation activation is deficient, T cells will become either partially activated, undergo apoptosis, or enter into anergy status.

Both B cells and monocytes typically express HLA molecules required for MHC-peptide complex formation, but lack high expression of co-stimulatory molecules, such as CD80 and CD86. Without further activation or maturation to obtain fully activated APC, a failed or suboptimal antigen-specific T cell priming and amplification may ensue. Thus, a separate APC induction and isolation step is usually necessary prior to antigen-specific T cell priming ex vivo, by producing either mature dendritic cells (mDC) from the precursor monocytes, or activated B cells.

3. SUMMARY

Provided herein are methods of generating antigen-specific T cells, e.g., cytotoxic T lymphocytes (T cells), starting from peripheral blood mononuclear cells without a separate step of generating and isolating antigen-presenting cells, such as dendritic cells, macrophages, and B cells, and with a single round of antigen stimulation.

In one aspect, provided herein are methods of producing a cell population comprising antigen-specific T cells, e.g., CTLs, comprising the steps of: (a) isolating blood mononuclear cells, e.g., peripheral blood mononuclear cells (PBMCs) or cord blood mononuclear cells, from a subject; (b) culturing said blood mononuclear cells, e.g., PBMCs or cord blood mononuclear cells, in an antigen presenting cell (APC) induction medium comprising interleukin 4 (IL-4) and soluble CD40 ligand (sCD40L) and/or comprising granulocyte-macrophage colony-stimulating factor (GM-CSF) and interferon, e.g., interferon α (IFN-α), to produce a first population of cells; (c) culturing the first population of cells in the presence of one or more antigens, to produce a second population of cells; and (d) culturing the second population of cells in a T cell expansion medium comprising interleukin 7 (IL-7), interleukin 15 (IL-15), and, optionally, IL-4, to produce a third population of cells; wherein the third population of cells comprises T cells that are CD3+ and specific for an antigen added in step (c). In certain aspects, the method further comprises a step of culturing the third population of cells in a second T cell expansion medium comprising IL-7 and IL-15, but not comprising IL-4, to create a fourth population of cells; wherein the fourth population of cells comprises T cells that are CD3+ and specific for an antigen added in step (c). In certain aspects, the method further comprises a step of isolating T cells that are CD3+ from the third population of cells or the fourth population of cells. In certain aspects, step (c) is performed in APC induction medium. In certain aspects, the T cell expansion medium comprises IL-4. In certain aspects, the subject is a human. It certain aspects, the antigen is a human antigen. In certain aspects, the antigen is a full-length protein. In certain aspects, the antigen is a fragment of a protein. In certain aspects, the antigen is a peptide representing a part of the protein. In certain aspects, the APCs produce the antigen from exogenous genetic material.

In certain aspects, the third population of cells comprises T cells that are additionally CD4+. In certain aspects, the third population of cells comprises T cells that are additionally CD8+. In certain aspects, the third population of cells comprises T cells that are additional CD4+ and CD8+.

In certain aspects, the fourth population of cells comprises T cells that are additionally CD4+. In certain aspects, the fourth population of cells comprises T cells that are additionally CD8+. In certain aspects, the fourth population of cells comprises T cells that are additionally CD4+ and CD8+.

In certain aspects, the APC induction medium comprises IL-4 and sCD40L. In certain aspects, the APC induction medium comprises 1-50 ng/mL of IL-4 and 0.1-5 μg/mL of sCD40L. In certain aspects, the APC induction medium comprises 8-12 ng/mL of IL-4 and 0.8-1.2 μg/mL of sCD40L. In certain aspects, the APC induction medium comprises 10 ng/mL of IL-4 and 1 μg/mL of sCD40L.

In certain aspects, the APC induction medium further comprises synthetic oligonucleotides with one or more unmethylated CpG dinucleotide motifs. In certain aspects, the APC induction medium further comprises GM-CSF and IFN-α. In certain aspects, the APC induction medium consists essentially of GM-CSF and IFN-α.

In certain aspects, the one or more antigens are, or are contained within, a pool of peptides, e.g., lyophilized peptides. In specific aspects, the pool of lyophilized peptides cover the sequences of human HPV16E6, HPV16E7, HPV18E6, and/or HPV18E7 proteins. In specific aspects, the peptides are at a concentration of 1 μg/mL.

In certain aspects, the T cell expansion medium comprises 10-100 ng/mL of IL-7, 2-20 ng/mL of IL-15, and 10-100 ng/mL of IL-4. In certain aspects, the T cell expansion medium comprises 40-60 ng/mL of IL-7, 7-11 ng/mL of IL-15, and 45-65 ng/mL of IL-4. In specific aspects, the T cell expansion medium comprises 50 ng/mL of IL-7, 9 ng/mL of IL-15, and 55 ng/mL of IL-4.

In certain aspects, the second T cell expansion medium comprises 10-100 ng/mL of IL-7 and 2-20 ng/mL of IL-15. In certain aspects, the second T cell expansion medium comprises 40-60 ng/mL of IL-7 and 7-11 ng/mL of IL-15. In specific aspects, the second T cell expansion medium comprises 50 ng/mL of IL-7 and 9 ng/mL of IL-15.

In certain aspects, the duration of step (b) is 1-3 days. In specific aspects, the duration of step (b) is 1 day. In certain aspects, the duration of step (d) is 8-16 days. In specific aspects, the duration of step (d) is 12 days.

In certain aspects, the blood mononuclear cells, e.g., PBMCs or cord blood mononuclear cells, are isolated from whole blood, buffy coat, or an enriched leukapheresis product. In certain aspects, the blood mononuclear cells, e.g., PBMCs or cord blood mononuclear cells, are seeded in the APC induction medium at a density of $4-6\times10^6/cm^2$. In specific aspects, the blood mononuclear cells, e.g., PBMCs or cord blood mononuclear cells, are seeded at a density of $5\times10^6/cm^2$. In specific aspects, the blood mononuclear cells, e.g., PBMCs or cord blood mononuclear cells, are seeded at a density greater than $5\times10^6/cm^2$.

In certain aspects, the antigen-specific CD3+ cells are identified by, or are identifiable by, intracellular cytokine staining (ICCS). In certain aspects, the culturing steps are performed in a gas-permeable enclosure, e.g., a G-REX® device. In certain aspects, one or more culturing steps are performed in T-flasks. In certain aspects, one or more culturing steps are performed in bags. In specific aspects, the bags are static bags. In certain aspects, the bags are gas-permeable. In certain aspects, one or more culturing steps are performed in a WAVE™ bioreactor (GE Healthcare Life Sciences). In certain aspects, one or more culturing steps are performed in spinner flasks.

In one aspect, provided herein are populations of antigen-specific T cells produced by a method comprising the steps of: (a) isolating blood mononuclear cells, e.g., PBMCs or cord blood mononuclear cells, from a subject; (b) culturing said blood mononuclear cells, e.g., PBMCs or cord blood mononuclear cells, in an antigen presenting cell (APC) induction medium comprising interleukin 4 (IL-4) and soluble CD40 ligand (sCD40L) and/or comprising granulocyte-macrophage colony-stimulating factor (GM-CSF) and interferon α (IFN-α), to produce a first population of cells; (c) culturing the first population of cells in the presence of one or more antigens, to produce a second population of cells; and (d) culturing the second population of cells in a T cell expansion medium comprising interleukin 7 (IL-7), interleukin 15 (IL-15), and IL-4, to produce a third population of cells; wherein the third population of cells comprises T cells that are CD3+ and specific for an antigen added in step (c). In certain aspects, the populations of cells are produced by a method which further comprises a step of culturing the third population of cells in a second T cell expansion medium comprising IL-7 and IL-15, but not comprising IL-4, to create a fourth population of cells; wherein the fourth population of cells comprises T cells that are CD3+ and specific for an antigen added in step (c). In certain aspects, the populations of cells are produced by a method which further comprises a step of isolating T cells that are CD3+ from the third population of cells or the fourth population of cells. In certain aspects, step (c) is performed in APC induction medium.

In one aspect, provided herein are compositions, e.g., pharmaceutical compositions, comprising the antigen-specific T cells described herein. In certain aspects, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, or 45% or more of the cells in the composition are antigen-specific T cells. In certain aspects, 50% of the cells in the composition are antigen-specific T cells. In certain aspects, the compositions comprise a pharmaceutically acceptable excipient.

In one aspect, provided herein are methods of treating a cancer or a viral infection comprising administering to a patient in need thereof a population of antigen-specific T cells produced by the methods described herein, wherein the isolated blood mononuclear cells, e.g., PBMCs or cord blood mononuclear cells, are autologous to the patient. In another aspect, provided herein are methods of treating a cancer or a viral infection comprising administering to a patient in need thereof a population of antigen-specific T cells produced by the methods described herein, wherein the isolated blood mononuclear cells, e.g., PBMCs or cord blood mononuclear cells, are not autologous to the patient. In certain aspects, the viral infection is a human papillomavirus (HPV) infection. In certain aspects, the viral infection is an HPV infection and the antigen is an HPV antigen. In certain other aspects, the viral infection is an Epstein-Barr virus (EBV) infection. In certain aspects, the viral infection is an EBV infection and the antigen is an EBV antigen. In a specific embodiment of the foregoing embodiments, the antigens are expressed in tumor cells comprising the viral infection. In certain aspects, provided herein are methods of administering a population of antigen-specific T cells to a patient in need thereof. In certain aspects, the method further comprises administering to said patient an immunomodulatory drug or an epigenetic modifier. In specific aspects, the method further comprises administering to said patient an immune checkpoint inhibitor. In more specific aspects, the immune checkpoint inhibitor is selected from the group consisting of an anti-CTLA-4 antibody, an anti-PD1 antibody, and an anti-PD-L1 antibody.

In one aspect, provided herein are methods of treating a cancer comprising administering to a patient in need thereof a population of antigen-specific T cells produced by the methods described herein, wherein the isolated blood mononuclear cells, e.g., PBMCs or cord blood mononuclear cells, are autologous to the patient. In certain aspects, the cancer is an HPV positive (HPV+) cancer. In certain aspects, the HPV+ cancer is head and neck cancer. In certain aspects, the head and neck cancer is squamous cell carcinoma of the head and neck. In certain aspects, the head and neck cancer is oropharyngeal cancer. In certain aspects, the HPV+ cancer is penile cancer. In certain aspects, the HPV+ cancer is cervical cancer. In certain aspects, the HPV+ cancer is anal cancer. In certain aspects, the HPV+ cancer is vulval cancer. In certain aspects, the HPV+ cancer is vaginal cancer. In certain aspects, the HPV+ cancer is lung cancer. In certain aspects, the HPV+ cancer is metastatic. In certain aspects, the HPV+ cancer is recurrent. In certain aspects, the HPV+ cancer is metastatic and recurrent. In certain aspects, the method further comprises administering to said patient an immunomodulatory drug or an epigenetic modifier. In certain aspects, the method further comprises administering to said patient an immune checkpoint inhibitor. In certain aspects, the immune checkpoint inhibitor is selected from the group consisting of an anti-CTLA-4 antibody, an anti-PD1 antibody, and an anti-PD-L1 antibody.

4. BRIEF DESCRIPTION OF THE FIGURES

FIG. 1: Expansion fold change of cells of all donors under various APC induction cytokine conditions described in Example 1.

Figure 2:
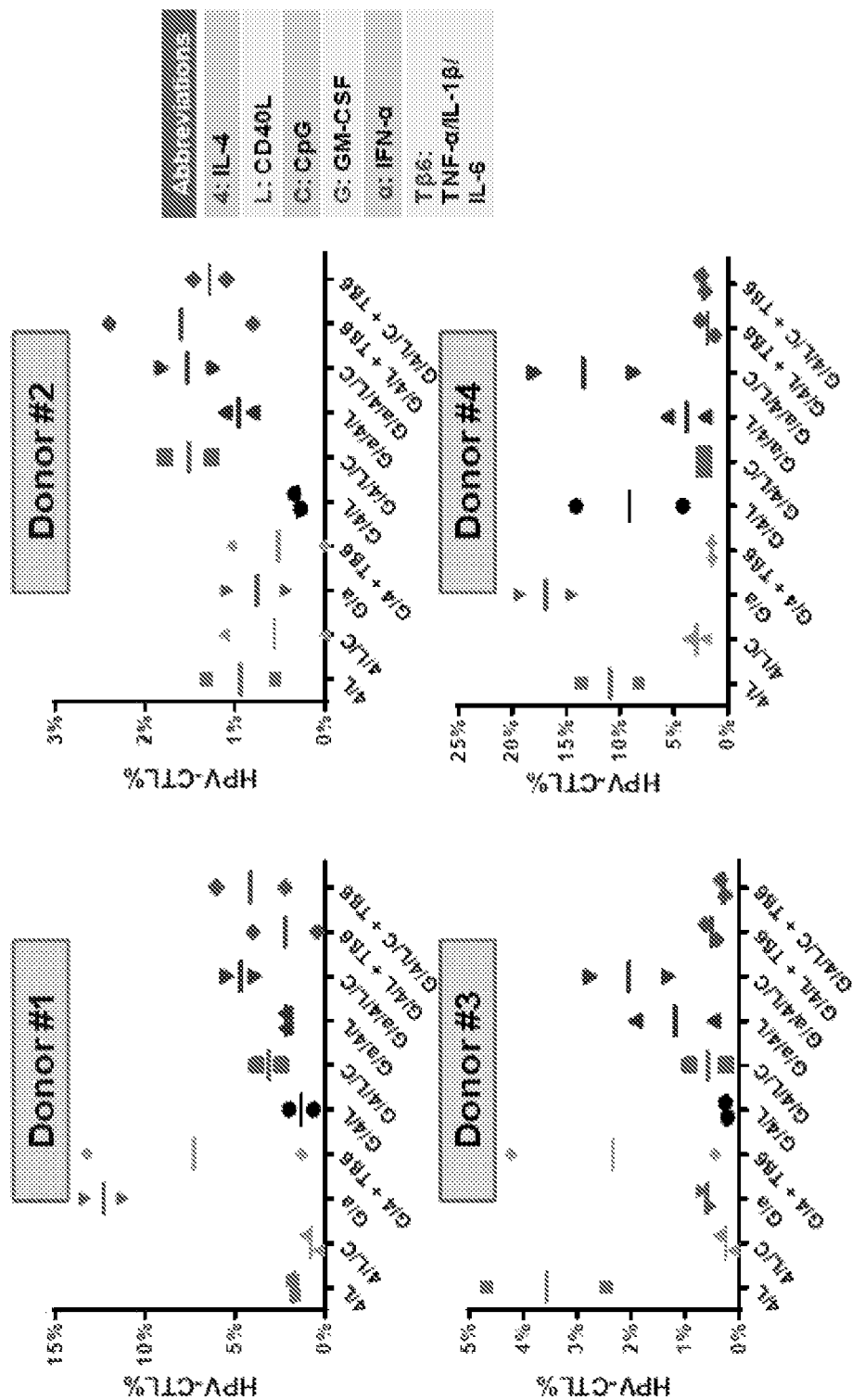

FIG. 2: HPV T cell frequency of all donors under various APC induction cytokine conditions described in Example 1.

Figure 3:
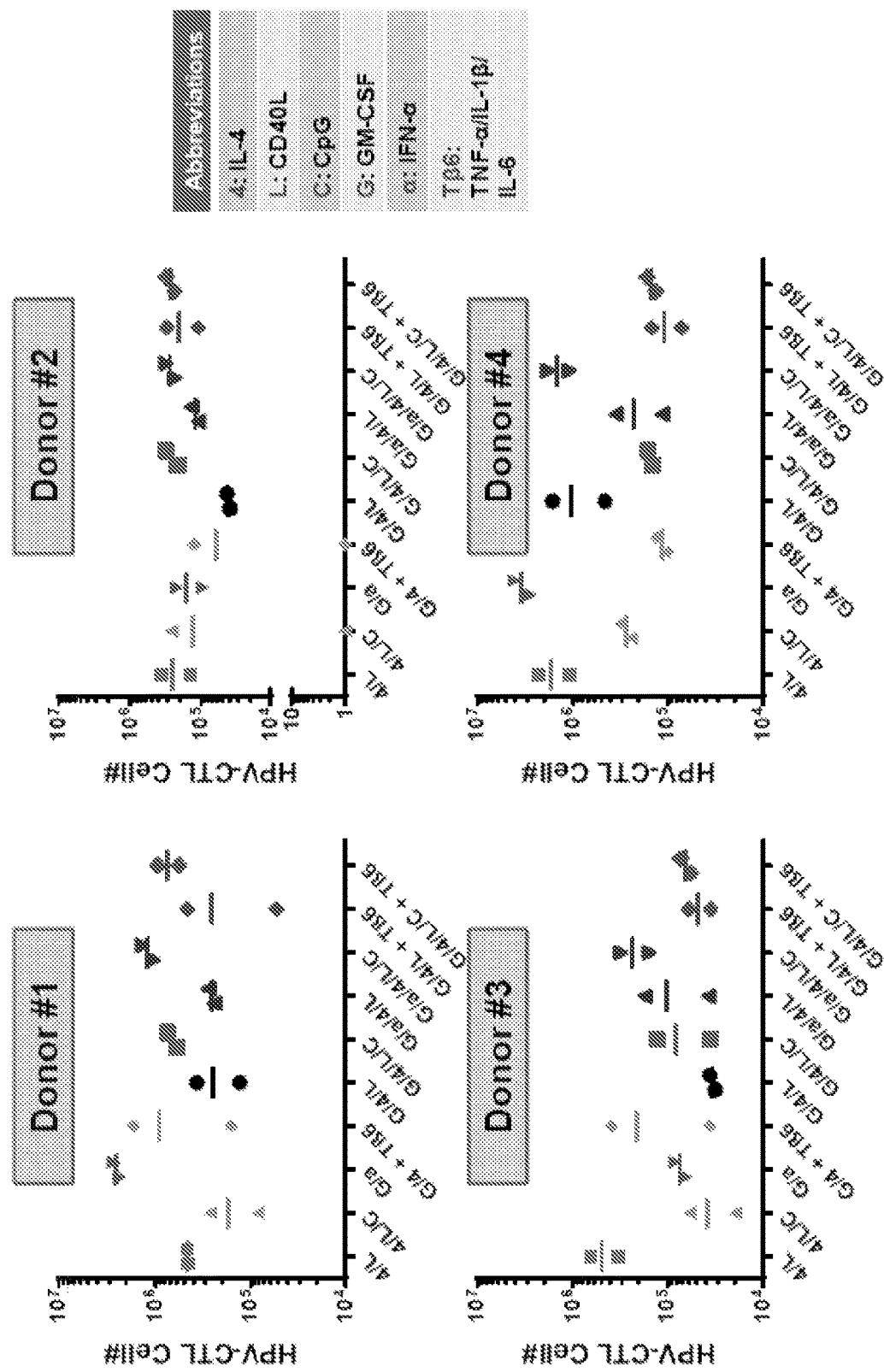

FIG. 3: HPV T cell yield in all donors under various APC induction cytokine conditions described in Example 1.

Figure 4A:
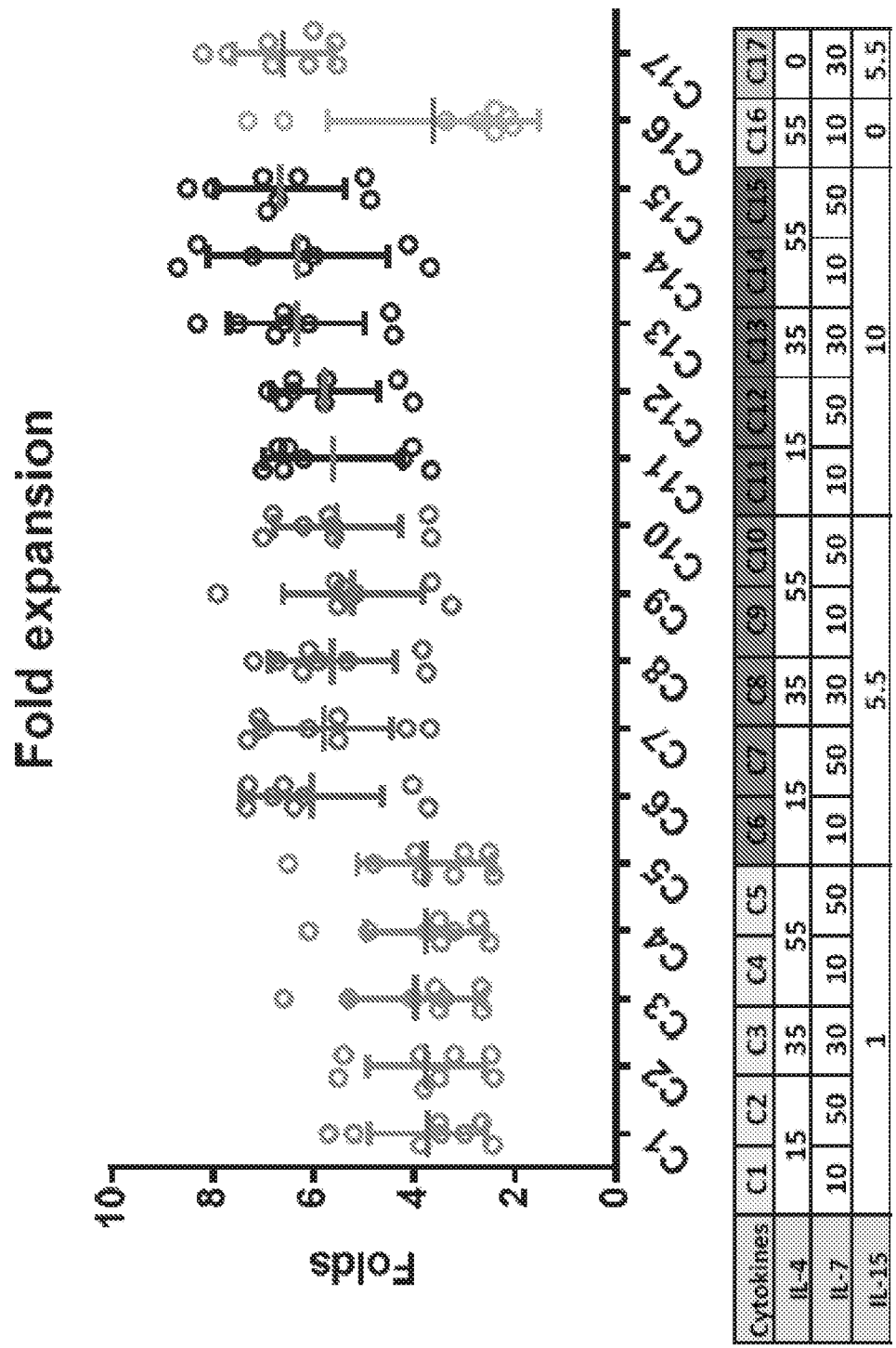
Figure 4B:
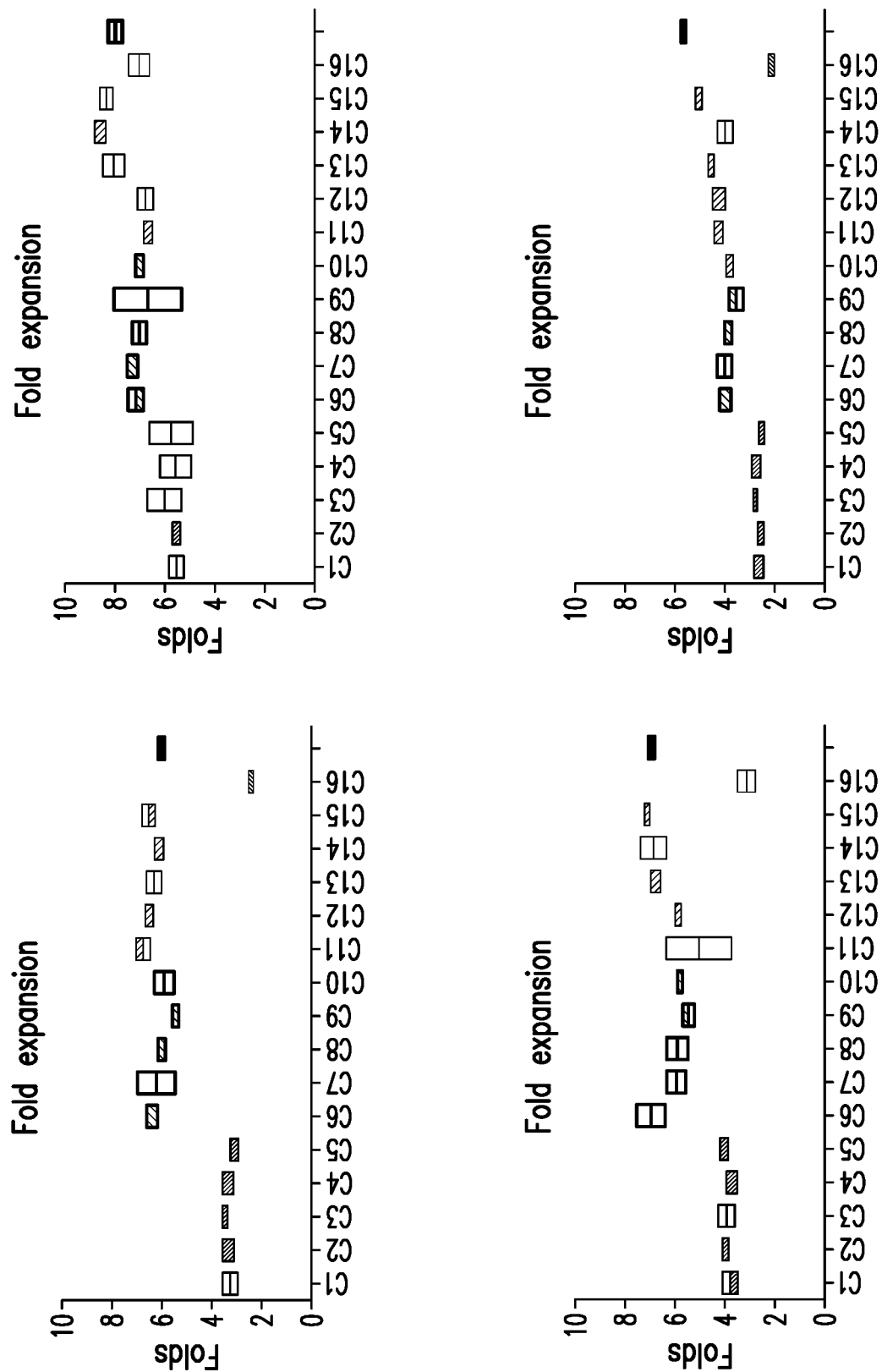

FIG. 4A-B: Total cell expansion folds at harvest under various T cell expansion cytokine conditions described in Example 2. (A) Summary plot of all 4 donors. (B) Individual plot for each donor.

Figure 5A:
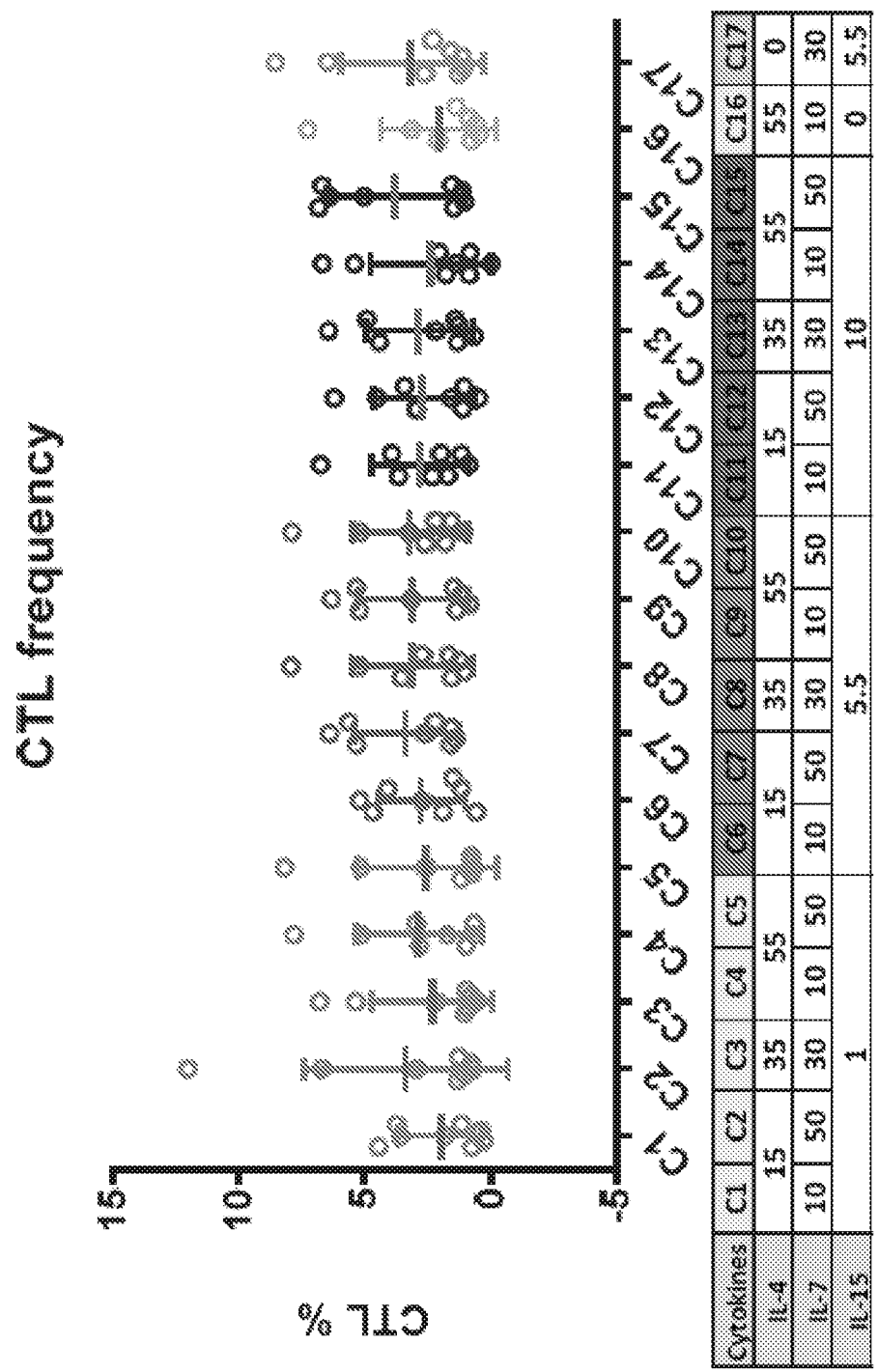
Figure 5B:
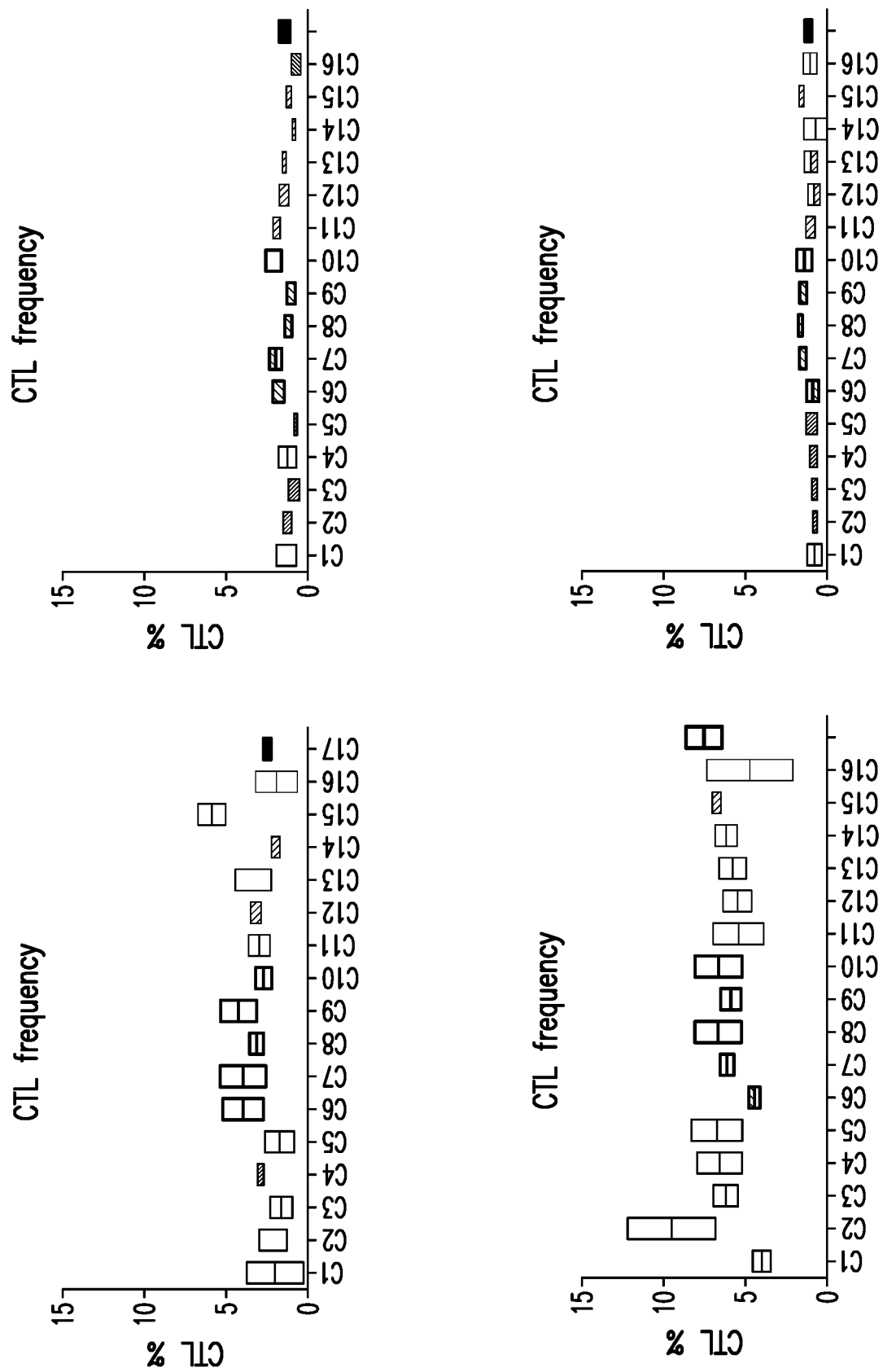

FIG. 5A-B: T cell frequency at harvest under various T cell expansion cytokine conditions described in Example 2. (A) Summary plot for all 4 donors. (B) Individual plot for each donor.

Figure 6A:
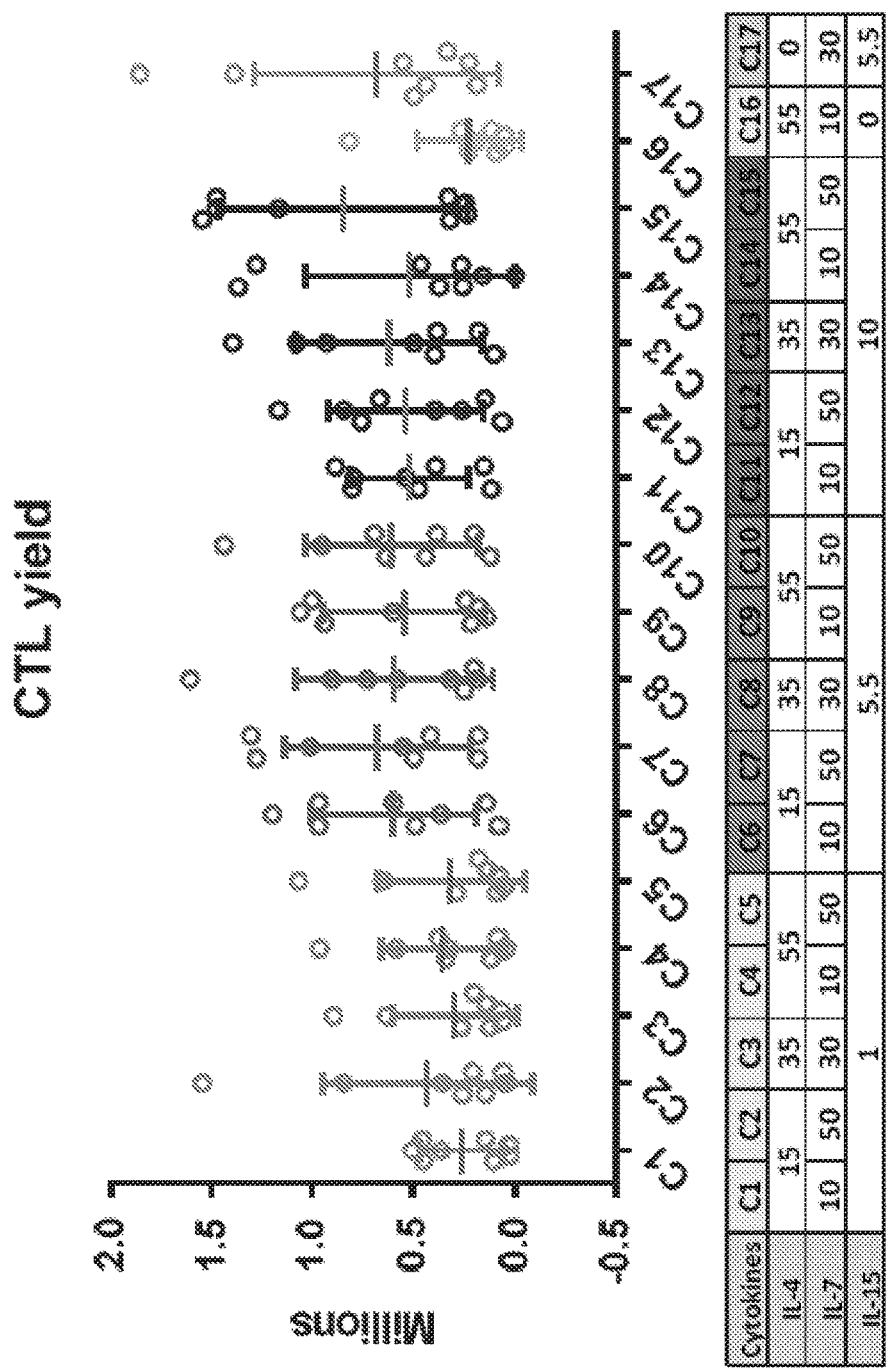
Figure 6B:
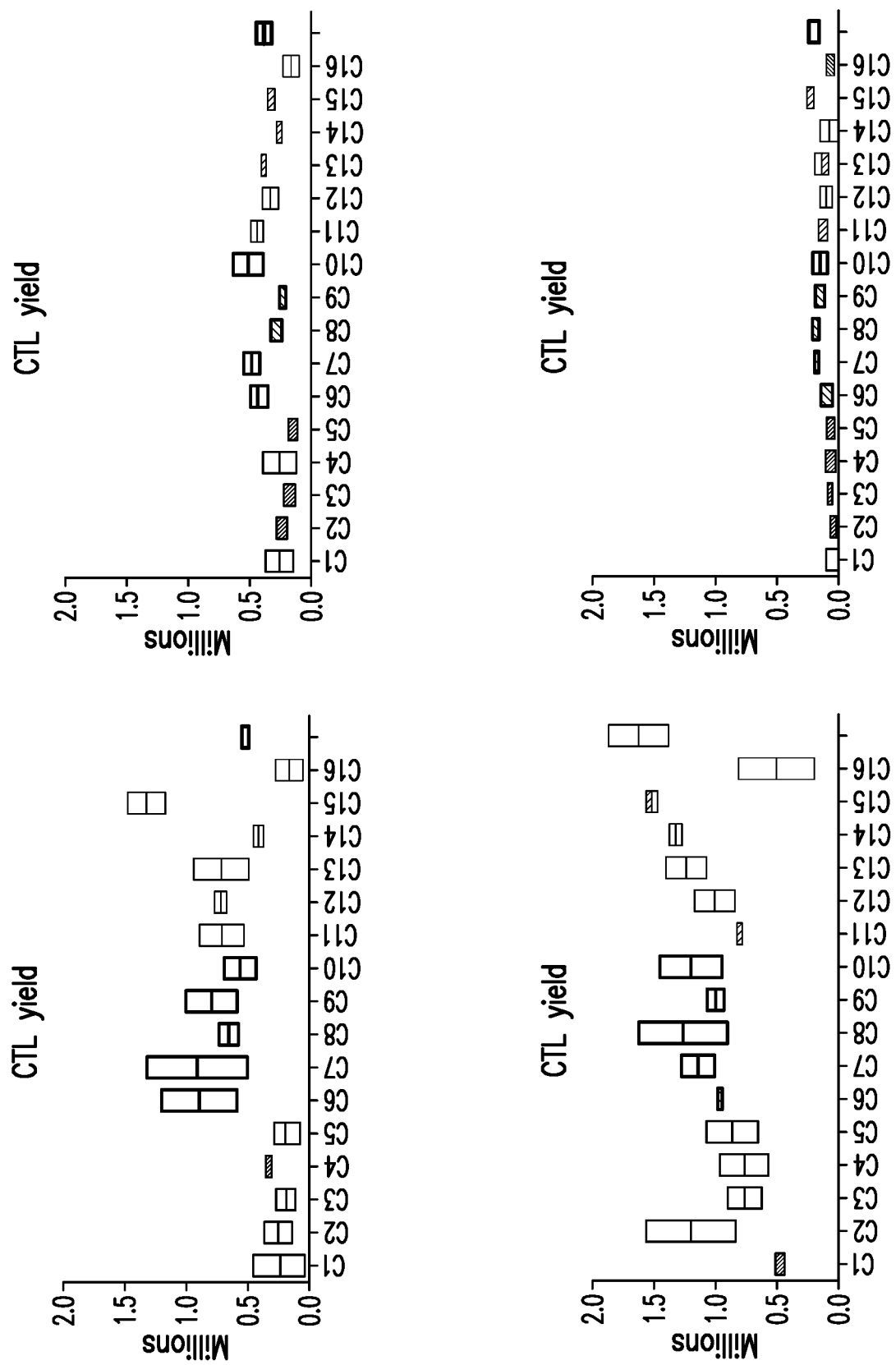

FIG. 6A-B: T cell yields at harvest under various T cell expansion cytokine conditions described in Example 2. (A) Summary plot for all 4 donors. (B) Individual plot for each donor.

Figure 7:
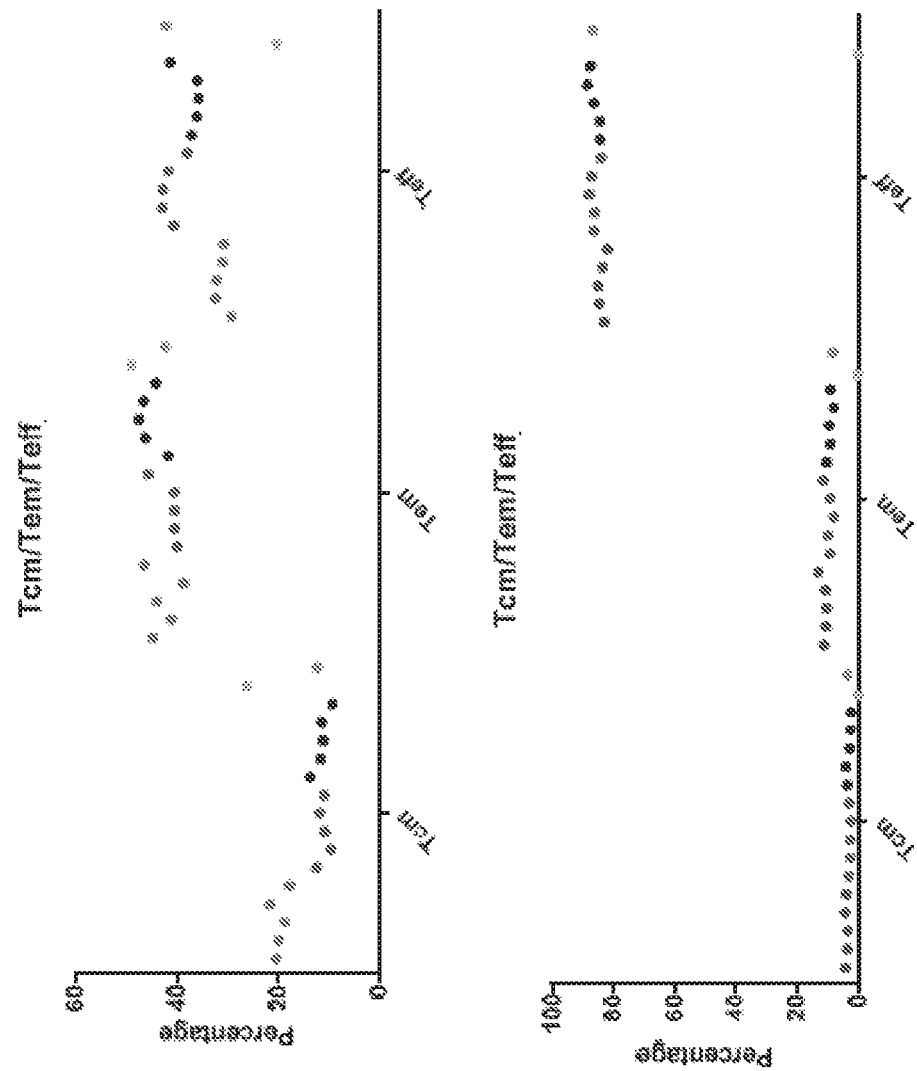

FIG. 7: Tcm, Tem and Teff percentages within CD45RO+ T cell populations under various T cell expansion cytokine conditions described in Example 2 for two different donors. Runs C1-C17 for each population (Tcm, Tem, and Teff) are shown in numerical order from left to right.

Figure 8:
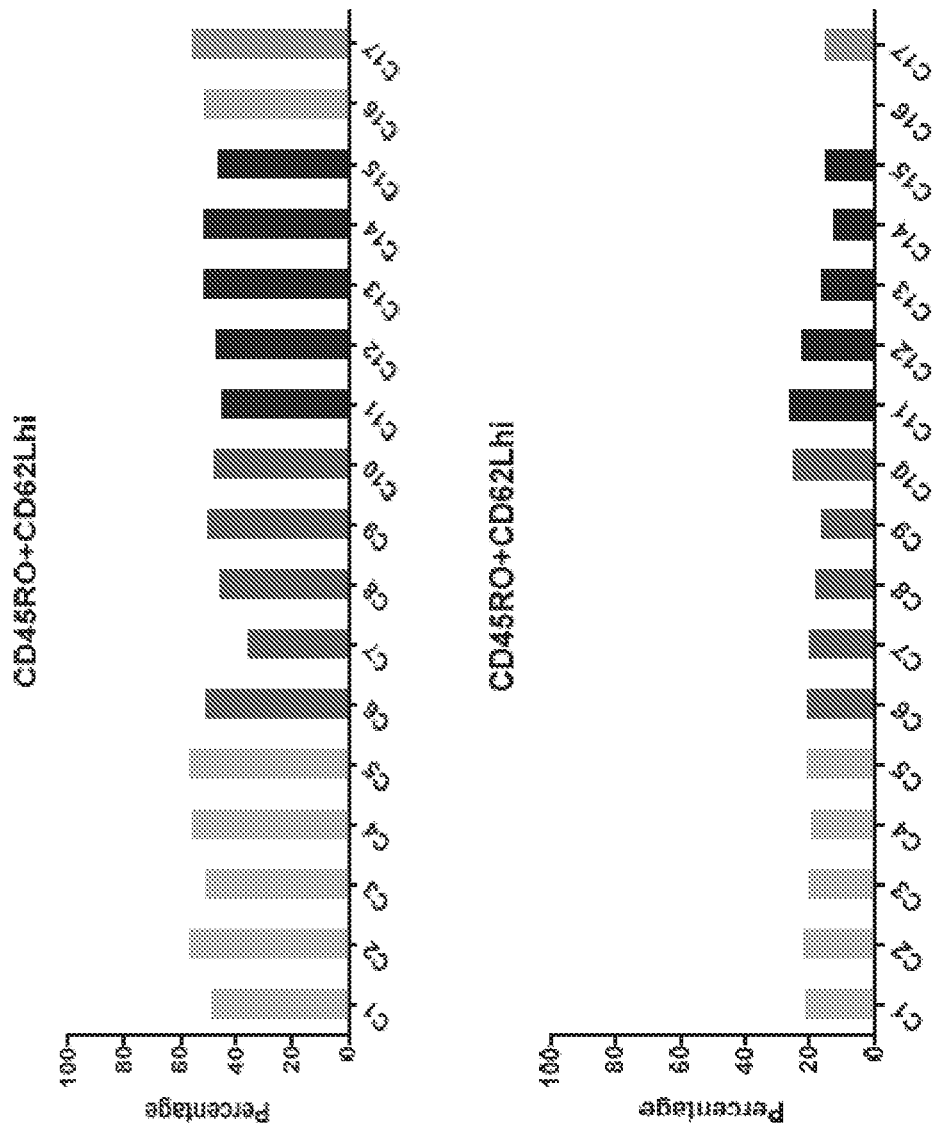

FIG. 8: CD45RO+CD62Lhi T cell populations under various T cell expansion cytokine conditions described in Example 2 for two different donors.

Figure 9:
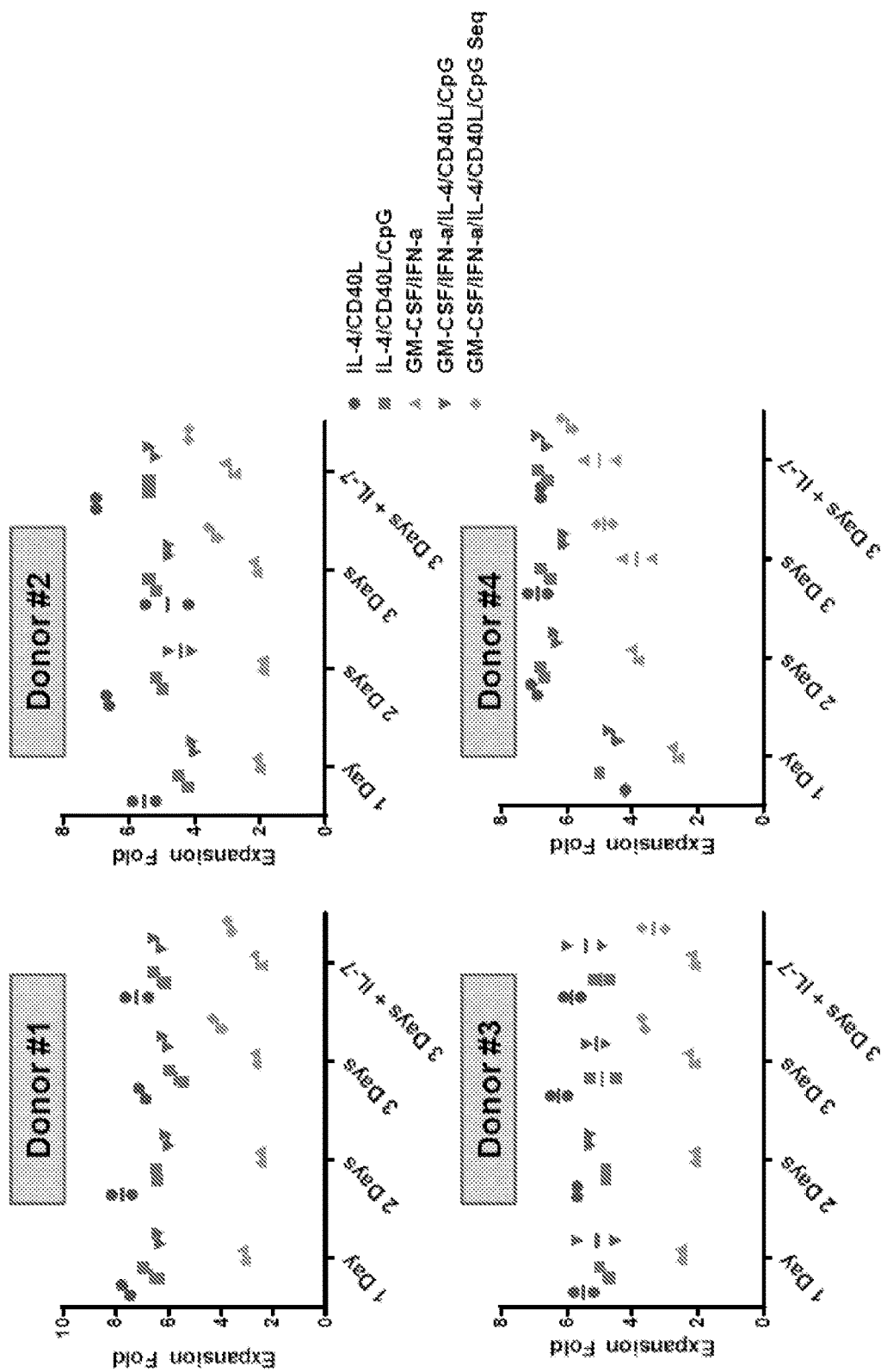

FIG. 9: Expansion Fold change of cells of all donors under various APC induction duration conditions described in Example 3.

Figure 10:
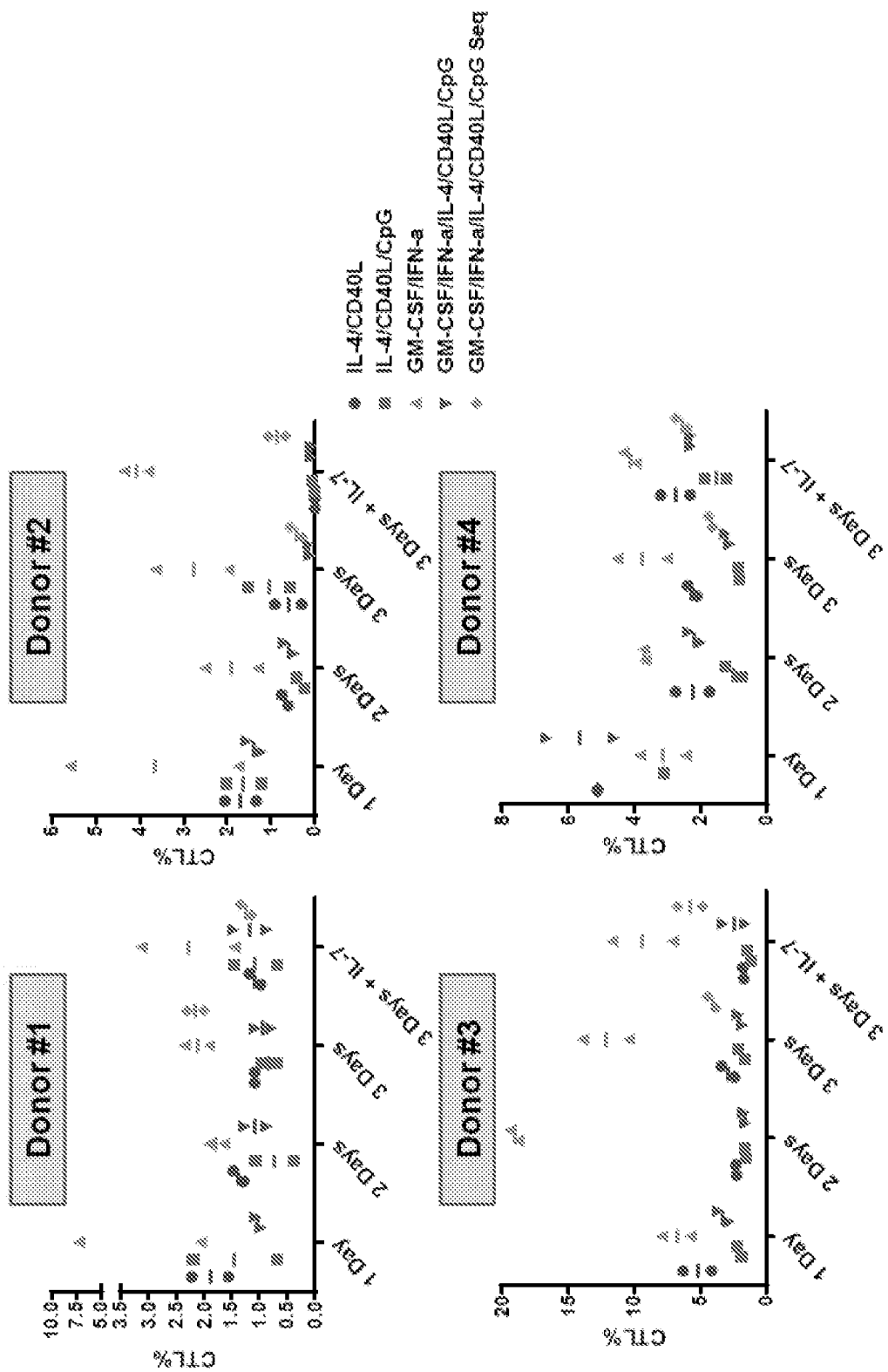

FIG. 10: HPV-T cell frequency of all donors under various APC induction duration conditions described in Example 3.

Figure 11:
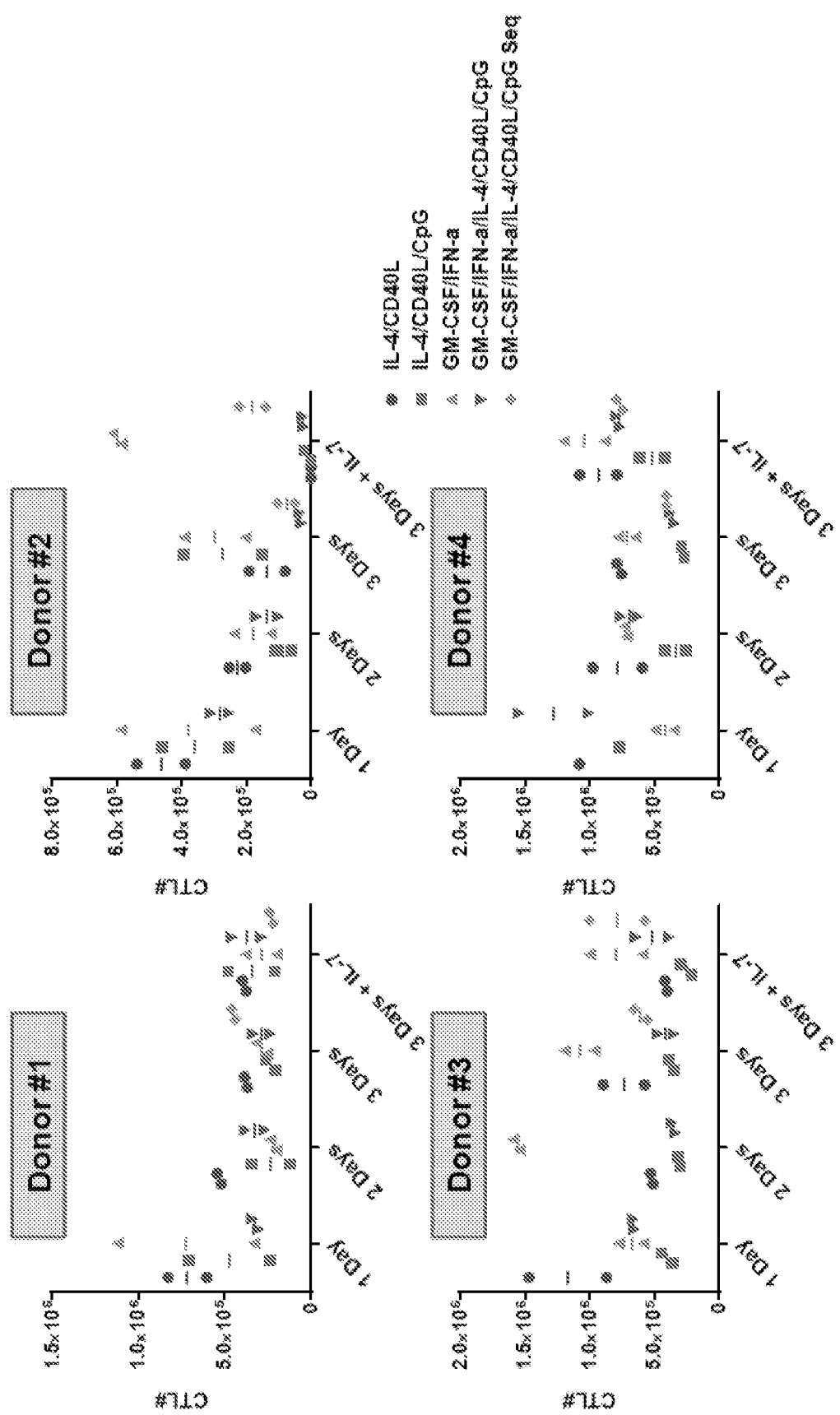

FIG. 11: HPV T cell yield from all donors under various APC induction duration conditions described in Example 3.

Figure 12:
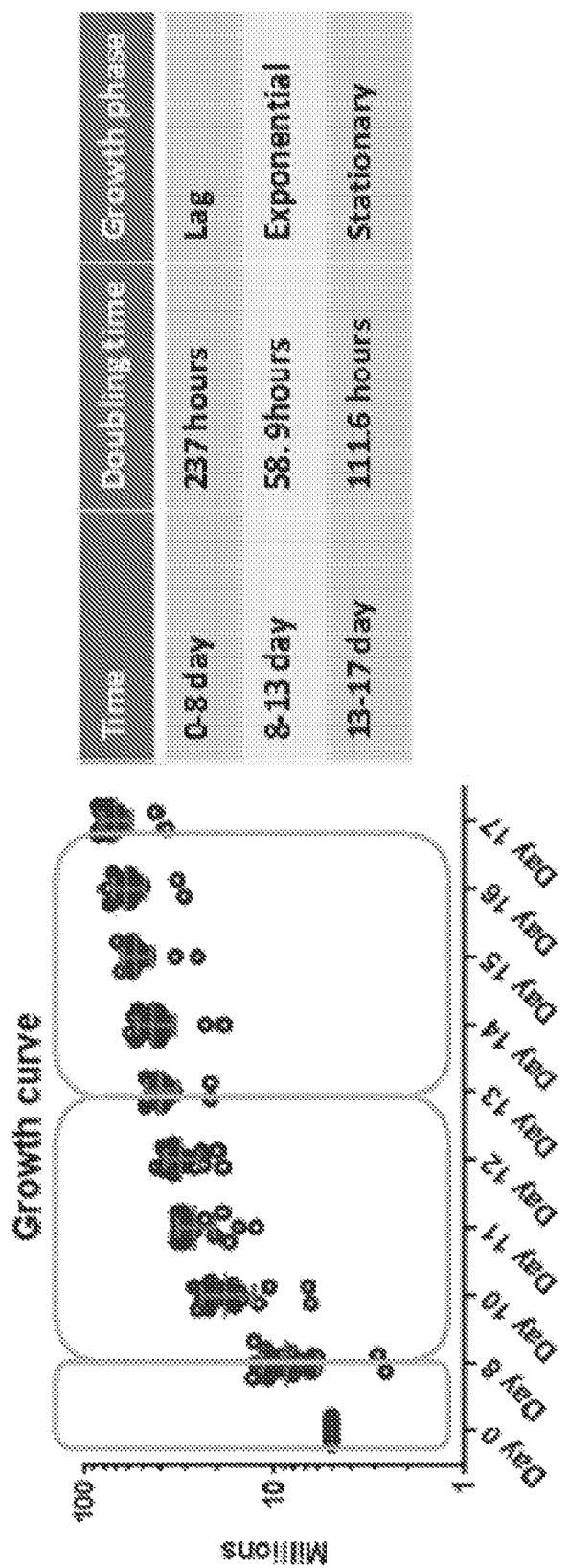

FIG. 12: Cell growth curve and doubling time under the conditions described in Example 4.

FIG. 13A-B: Changes with cell viability (A) and cell size (B) with expansion extension under the conditions described in Example 4.

FIG. 14A-D: Total cell expansion (A), fold change (B), T cell frequency (C) and T cell yield (D) at harvest on day 12, 14 and 16 post antigen stimulation under the conditions described in Example 4.

Figure 15:
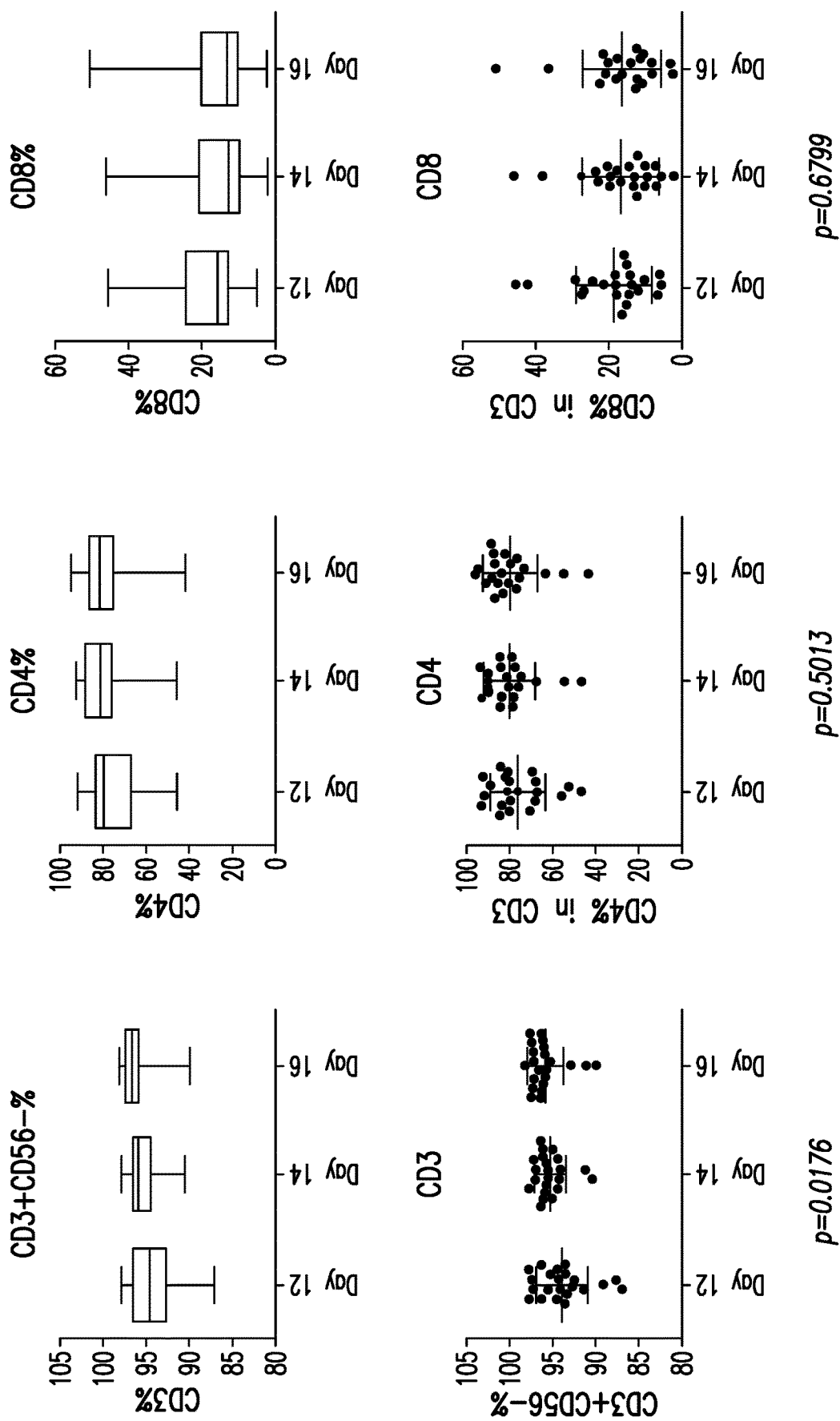

FIG. 15: T cell purity and CD4/CD8 cell percentage at harvest from day 12 to day 16 under the conditions described in Example 4.

Figure 16:
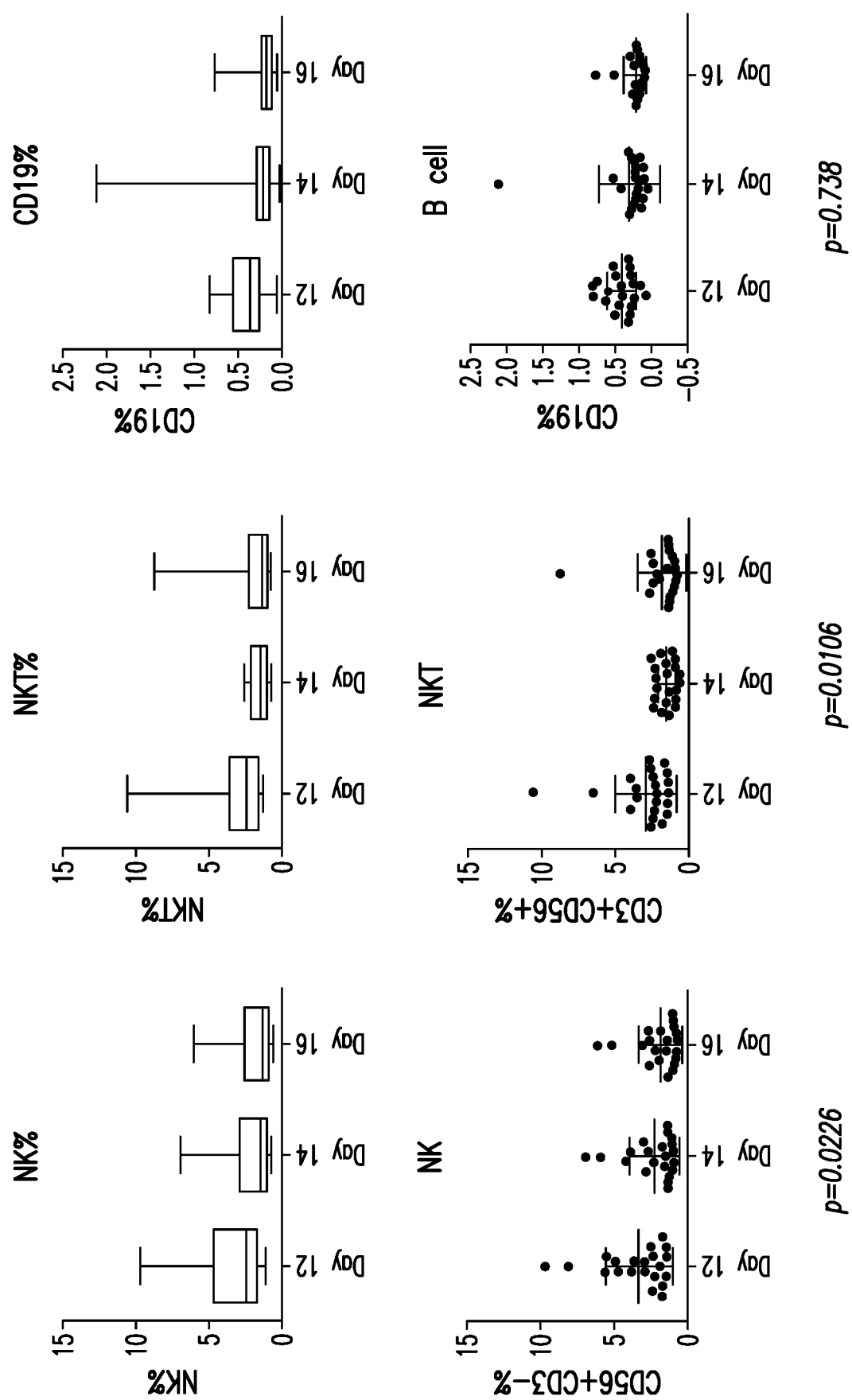

FIG. 16: Non-T cell population at harvest from day 12 to day 16 under the conditions described in Example 4.

Figure 17:
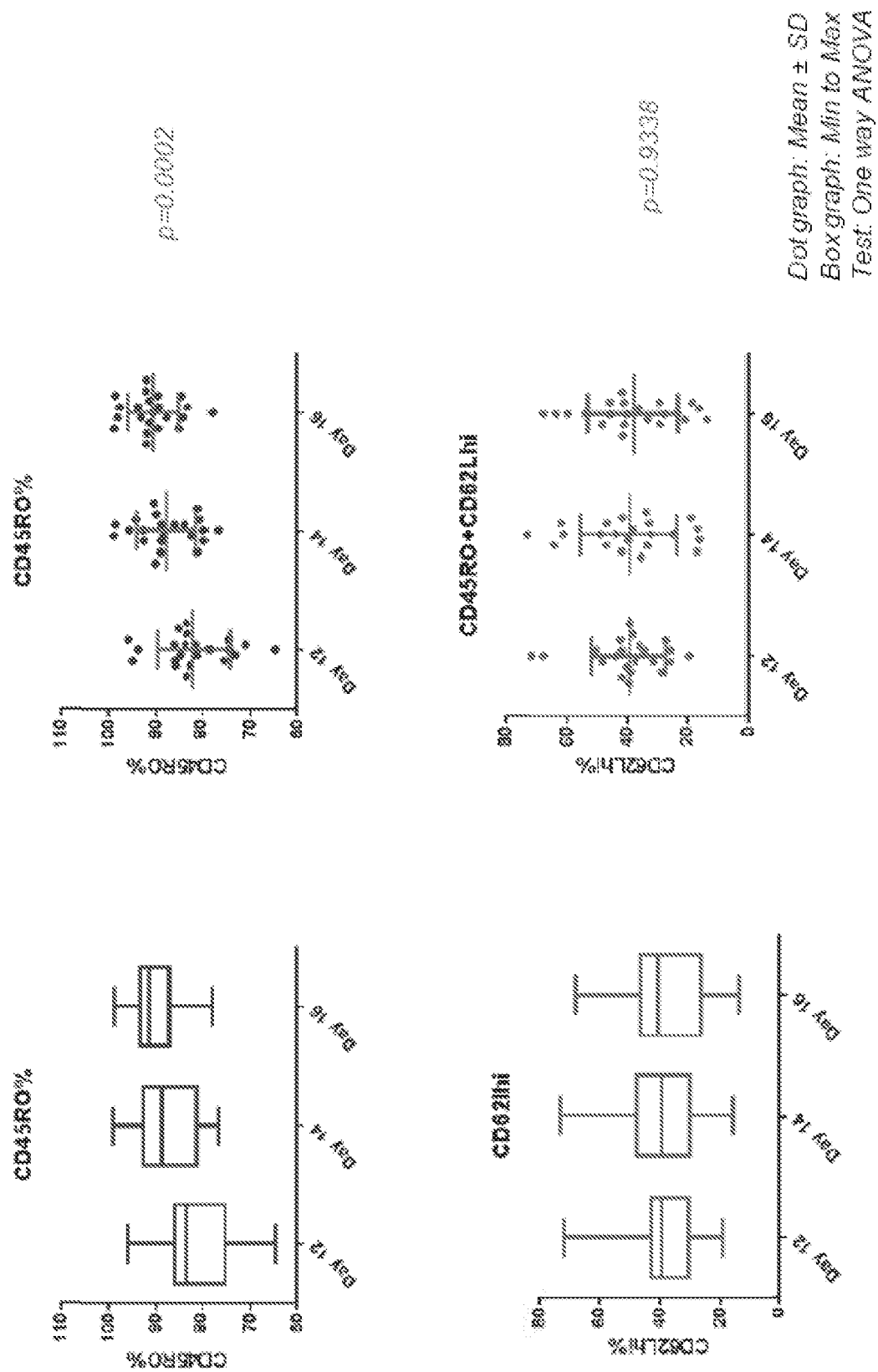

FIG. 17: Changes of Memory T cell and CD45RO+ CD62Lhi percentage with culture extension under the conditions described in Example 4. Statistical significance was determined by one-way ANOVA analysis.

Figure 18:
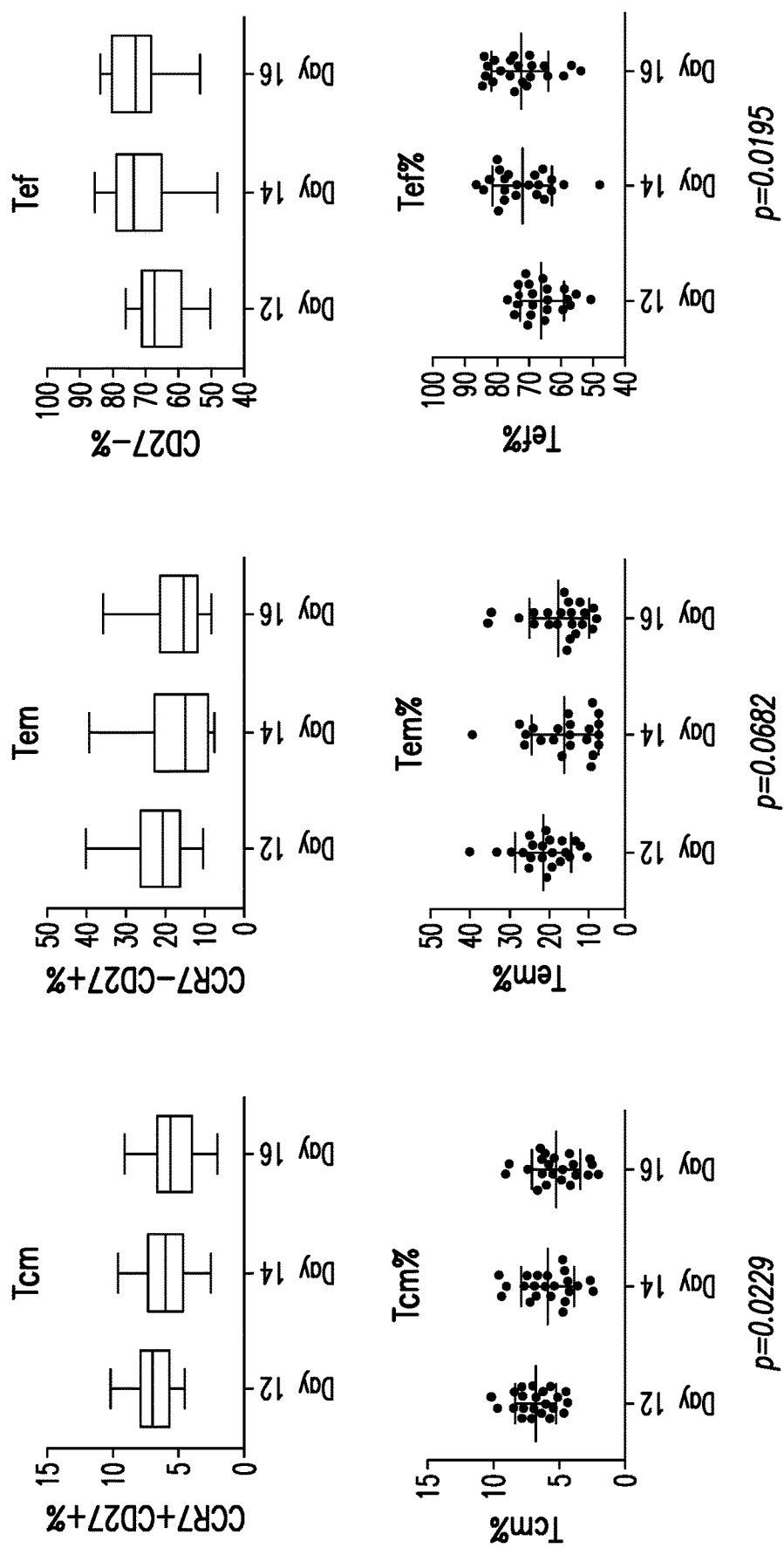

FIG. 18: Changes of percentages of central memory, effect memory and effect T cell populations with culture extension from 12 days to 16 days under the conditions described in Example 4. Within the CD45RO+ population, reduction of central memory T cell population and raise of effect T cell population were seen from day 12 to day 16 cultures. Statistical significance was determined by one-way ANOVA analysis.

Figure 19:
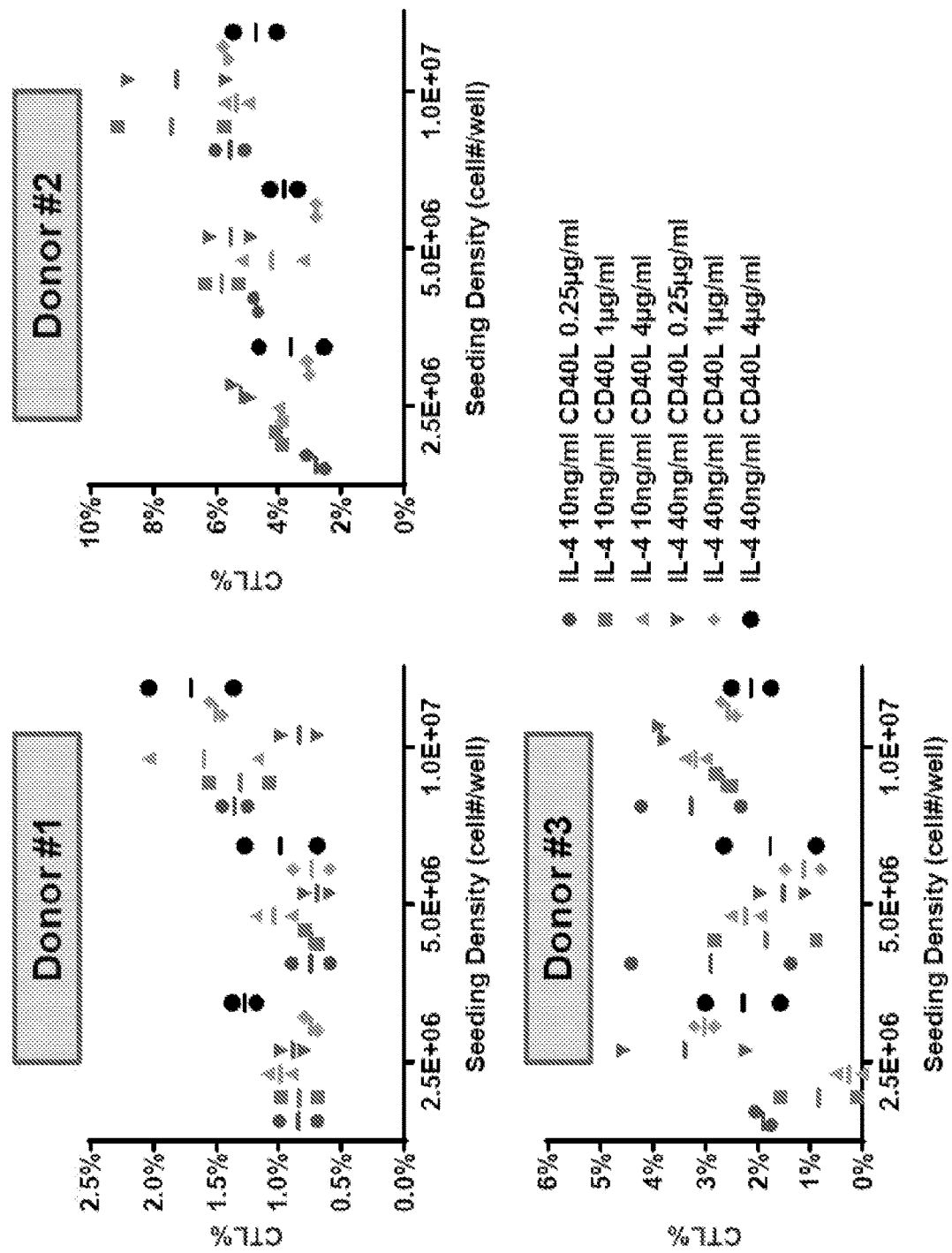

FIG. 19: HPV T cell frequency of all donors under the various seeding density and APC cytokine cocktail concentration conditions described in Example 5.

Figure 20:
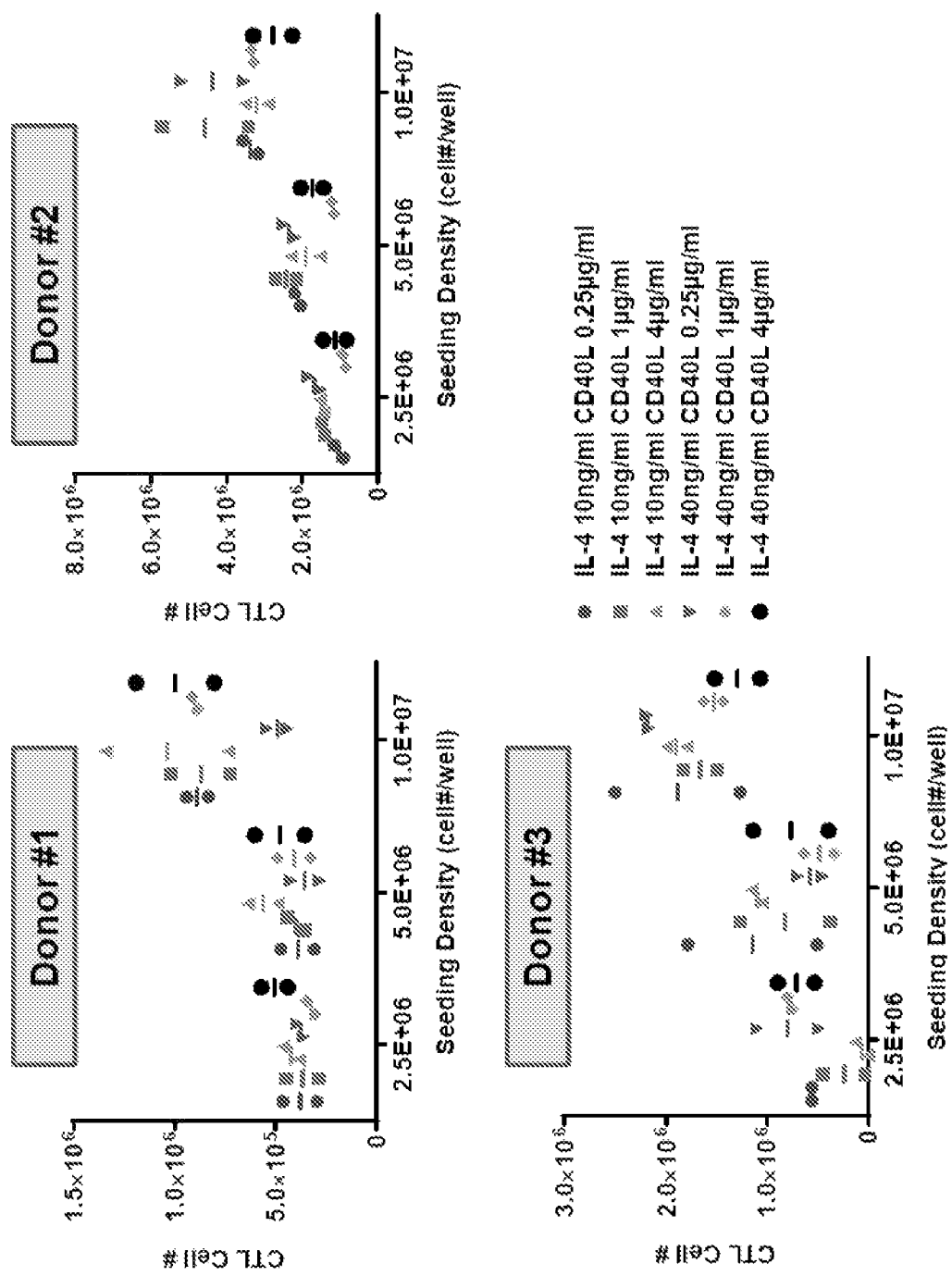

FIG. 20: HPV T cell yield of all donors under the various seeding density and APC cytokine cocktail concentration conditions described in Example 5.

Figure 21:
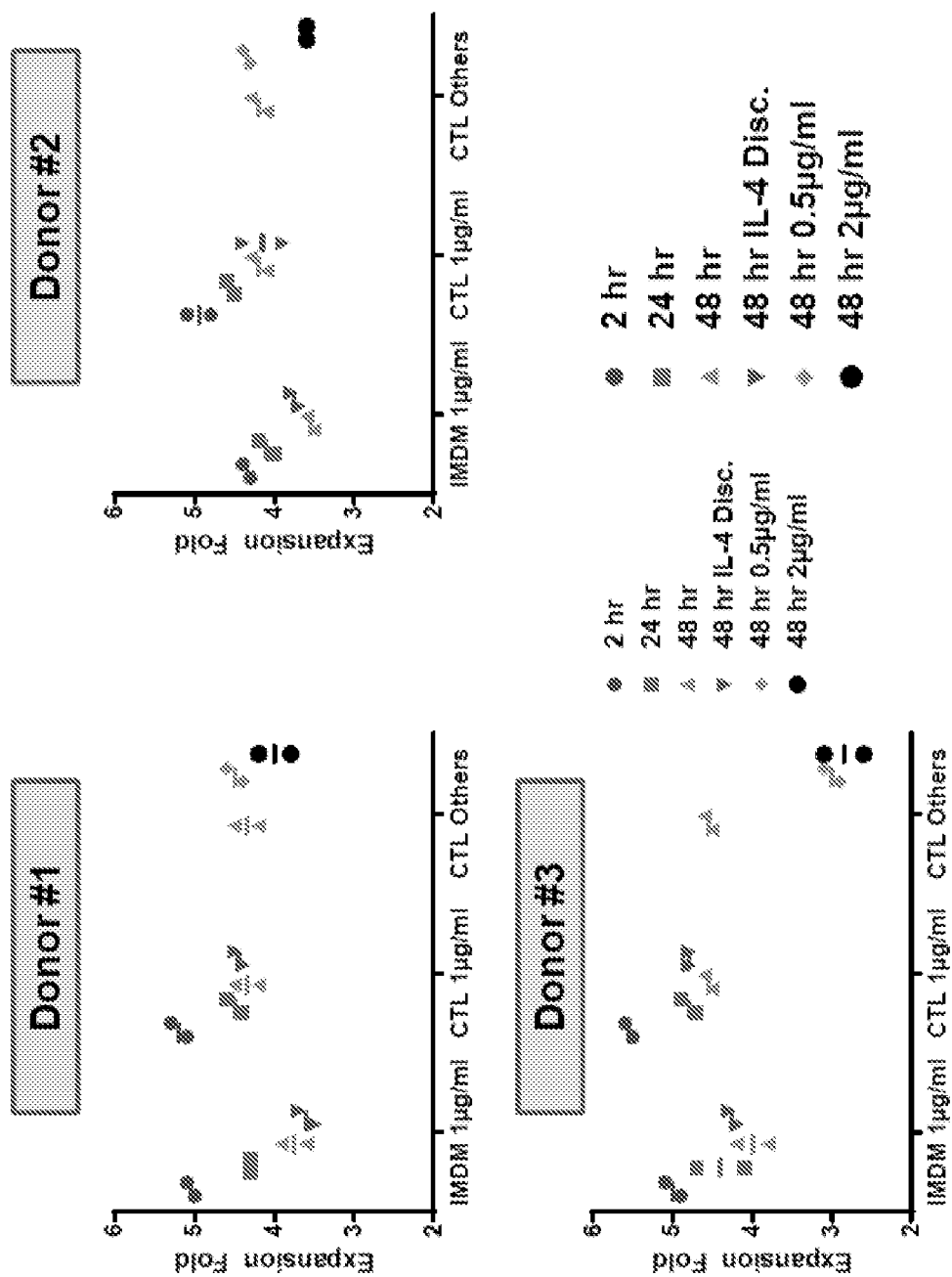

FIG. 21: Cell expansion fold change of all donors under the conditions described in Example 6. The results are grouped with APC induction media type at the x-axis. The legend of the graphs is shown at the bottom right corner. "IL-4 Disc." means IL-4 discontinuation.

Figure 22:
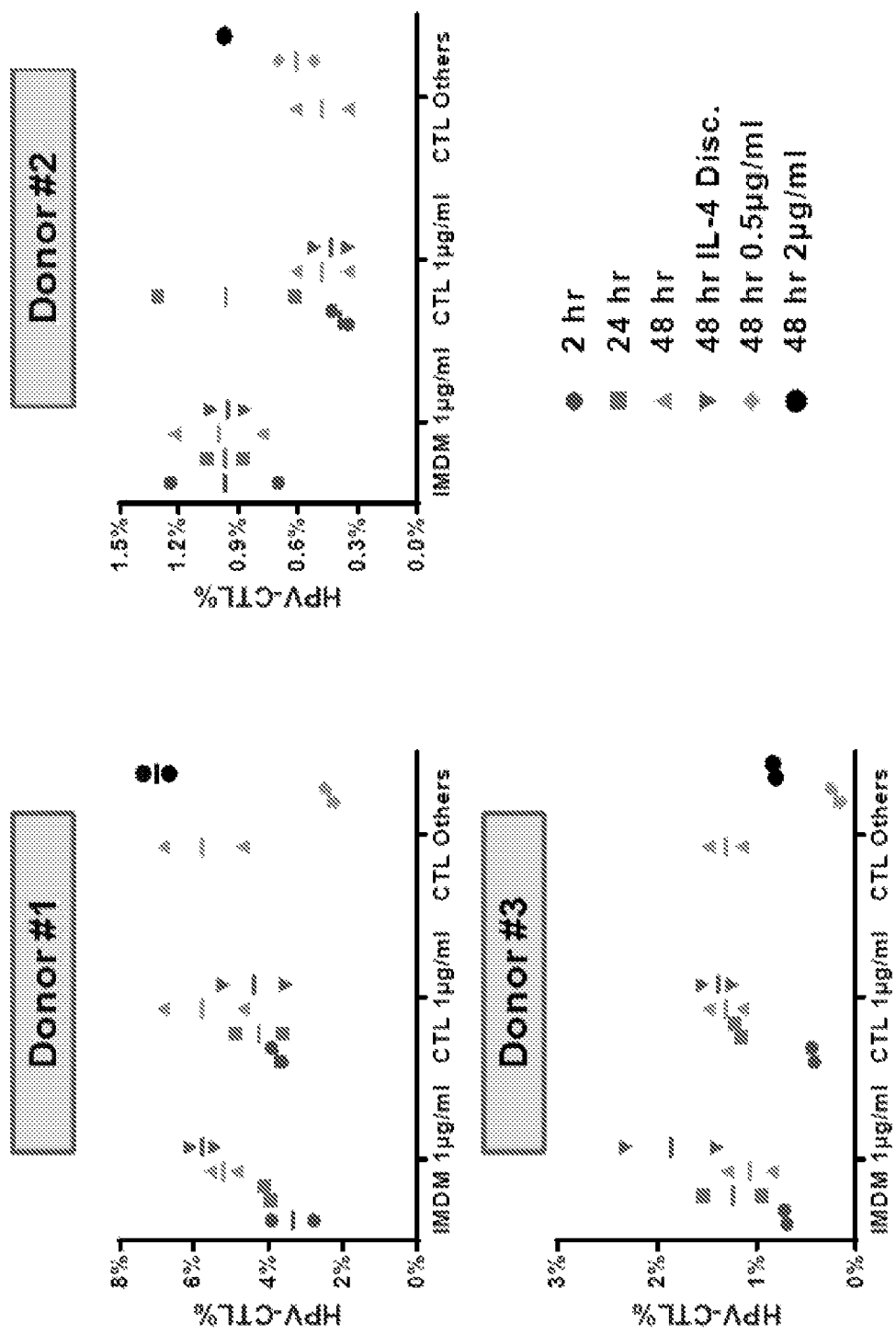

FIG. 22: HPV T cell frequency of all donors under the conditions described in Example 6. The results are grouped with APC induction media type at the x-axis. The legend of the graphs is shown at the bottom right corner. "IL-4 Disc." means IL-4 discontinuation.

Figure 23:
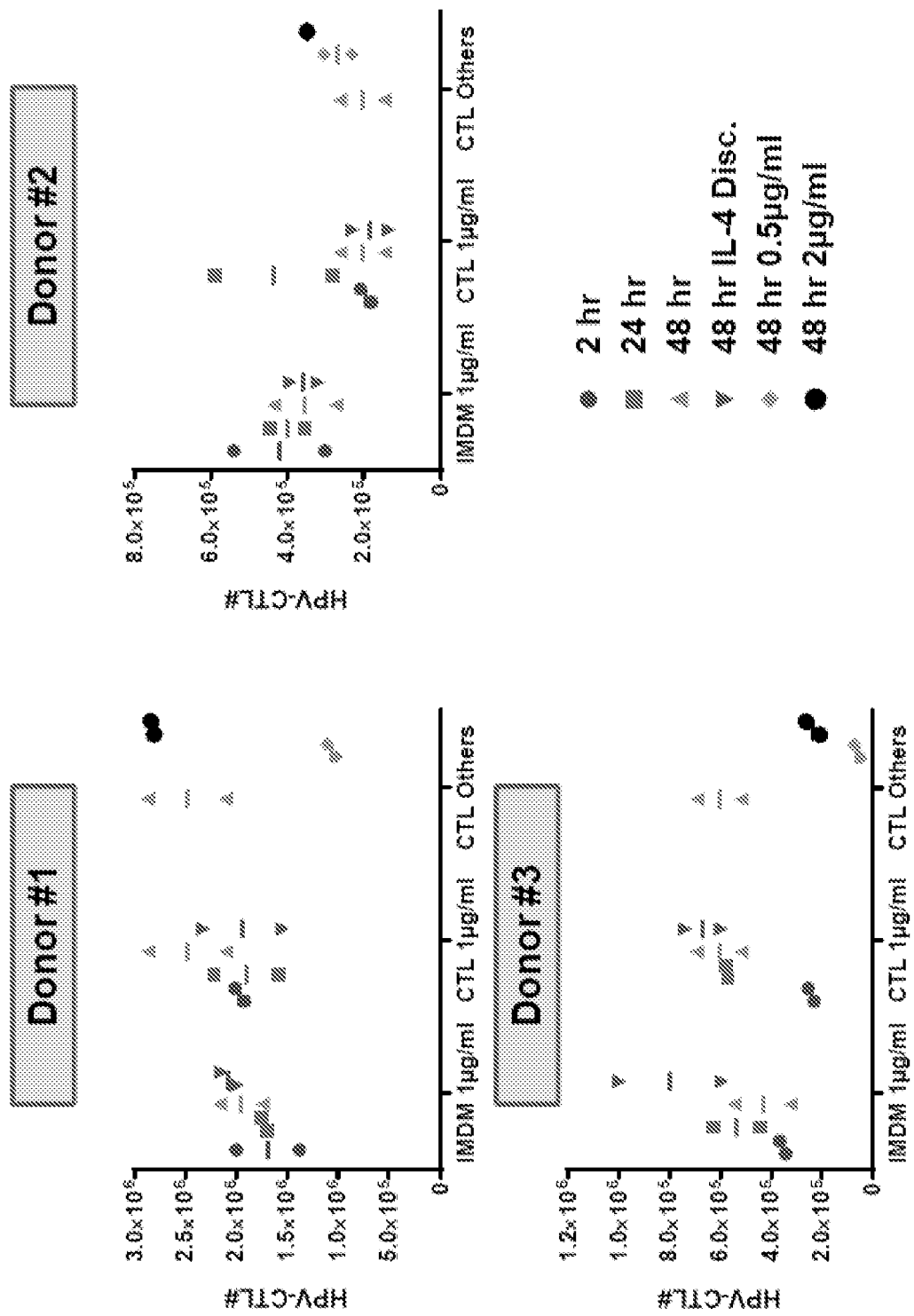

FIG. 23: HPV T cell yield of all donors under the conditions described in Example 6. The results are grouped with APC induction media type at the x-axis. The legend of the graphs is shown at the bottom right corner. "IL-4 Disc." means IL-4 discontinuation.

Figure 24:
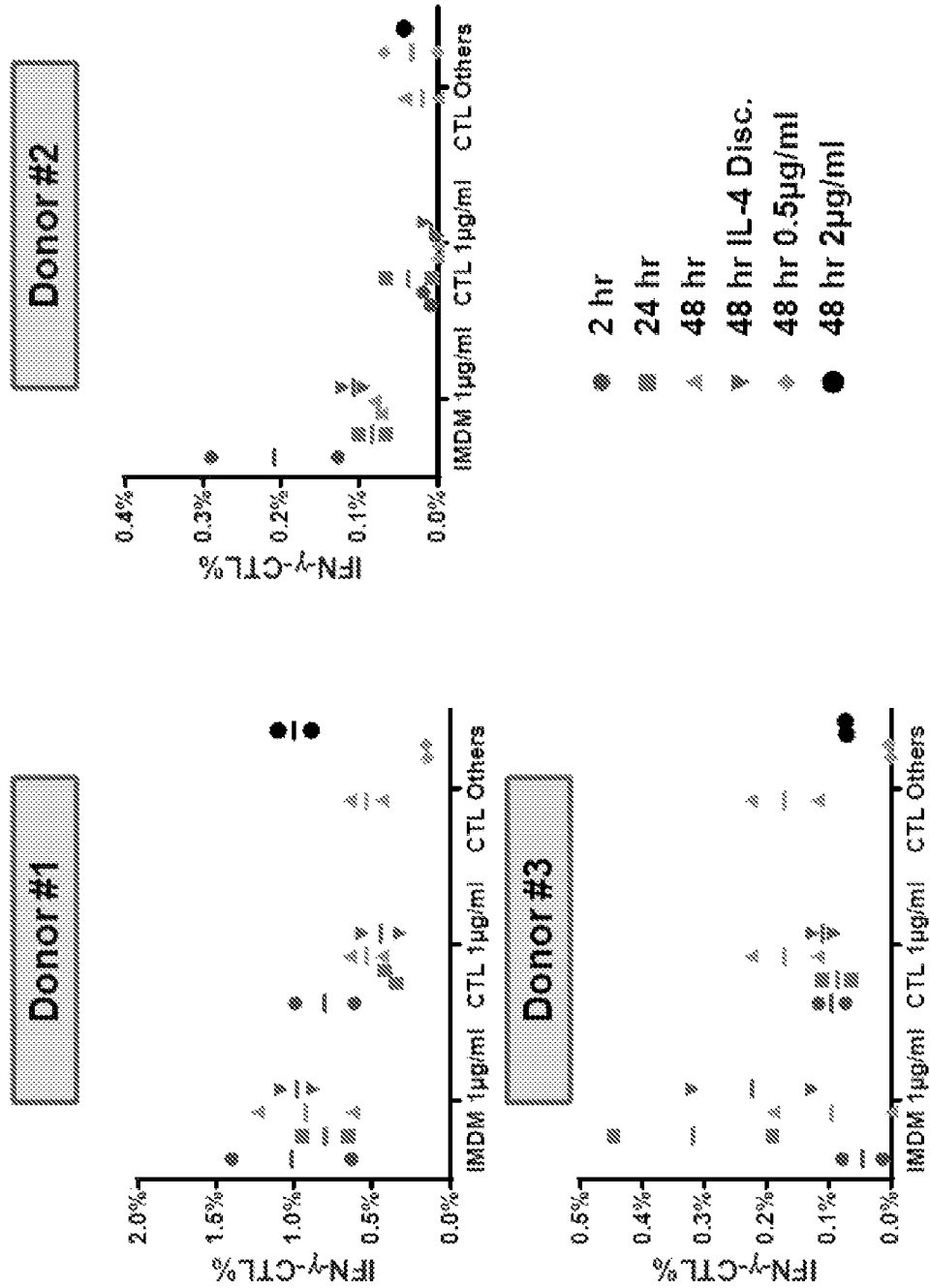

FIG. 24: IFN-γ-HPV T cell frequency of all donors under the conditions described in Example 6. The results are grouped with APC induction media type at the x-axis. The legend of the graphs is shown at the bottom right corner. "IL-4 Disc." means IL-4 discontinuation. The results are obtained from cells that are gated within CD3+ population.

Figure 25:
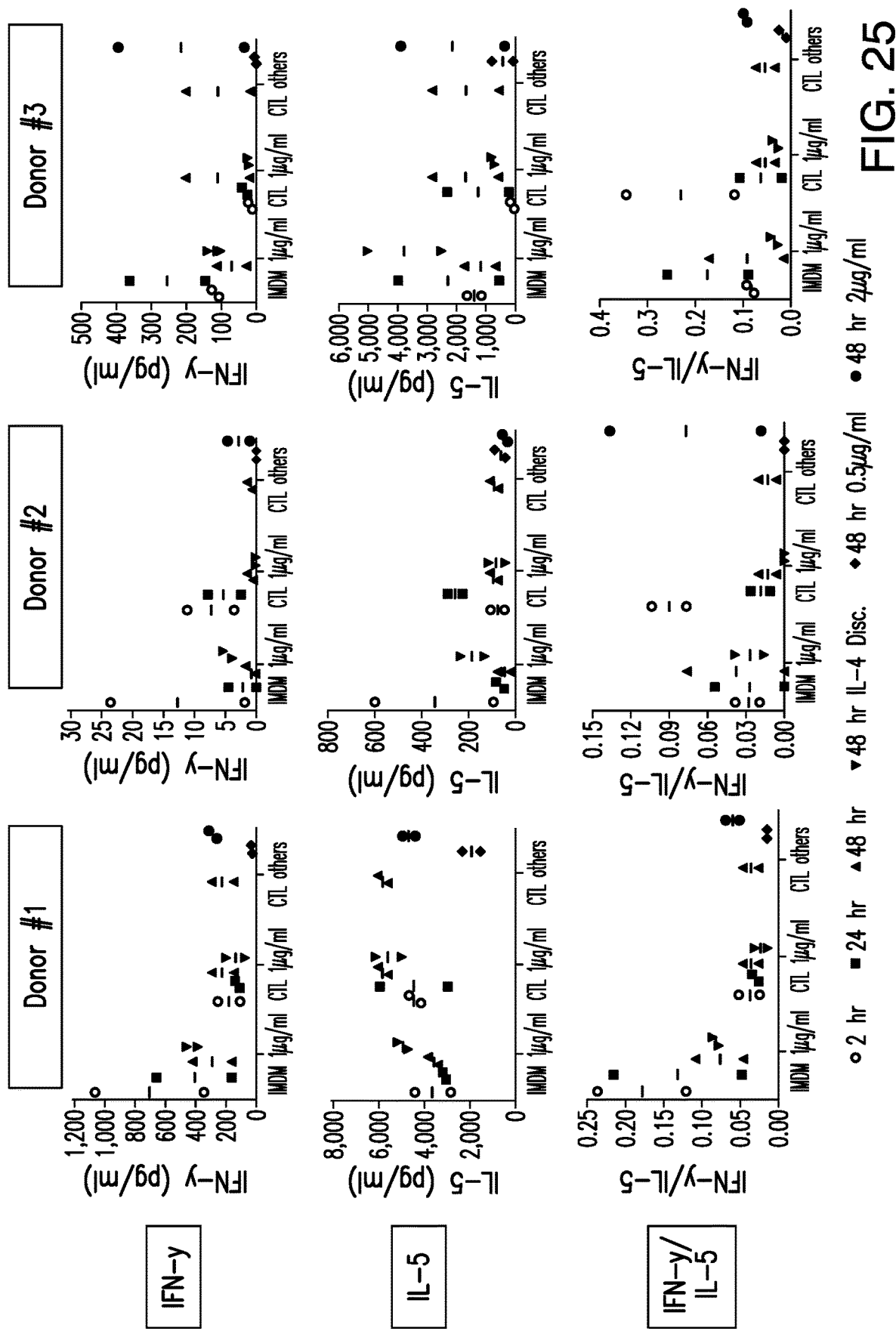

FIG. 25: Th1/Th2 ratio based on cytokine secretion of all donors under the conditions described in Example 6. IFN-γ level, IL-5 level and IFN-γ/IL-5 ratio as the Th1/Th2 ratio are presented. The results are grouped with APC induction media type at the x-axis. The legend of the graphs is shown at the bottom. "IL-4 Disc." means IL-4 discontinuation.

Figure 26:
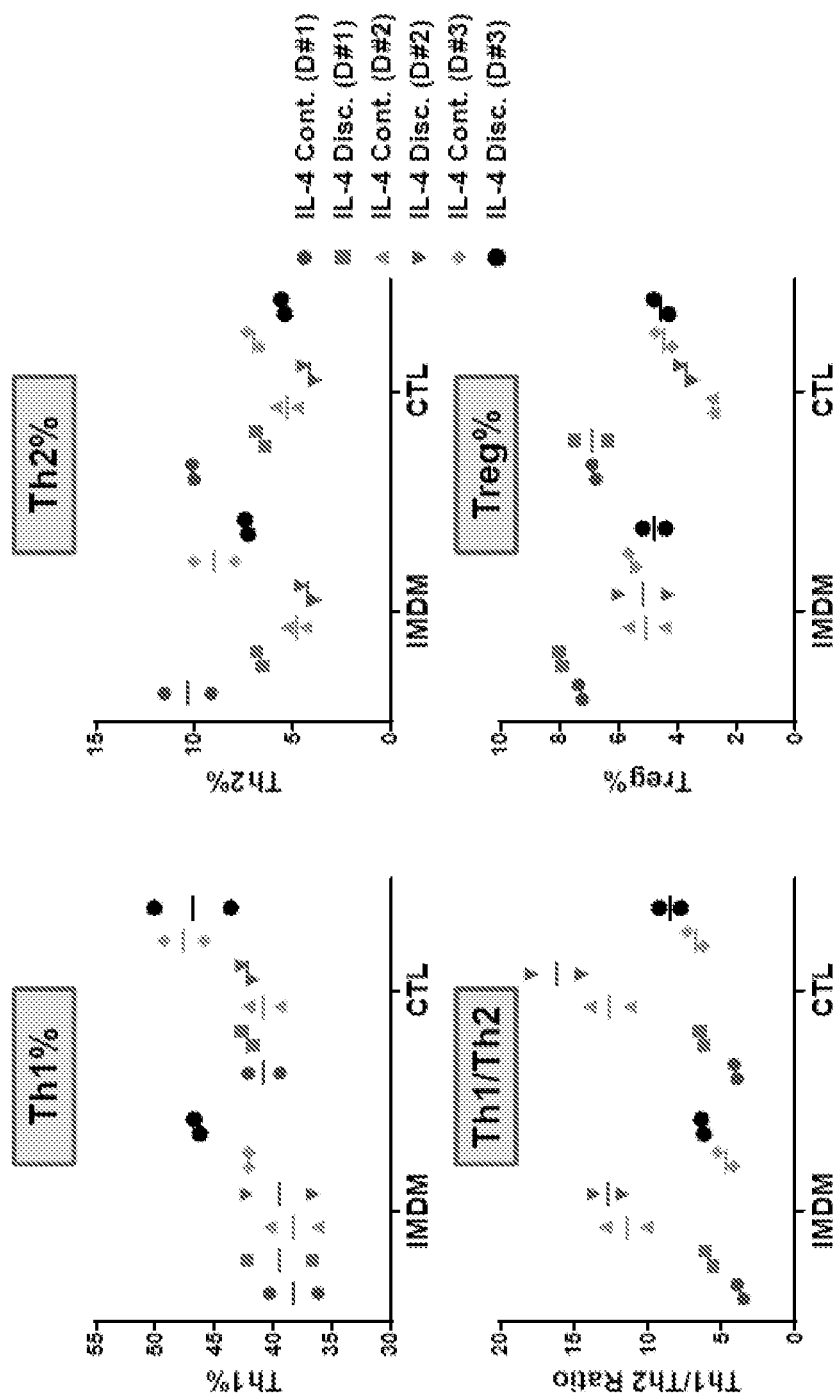

FIG. 26: Th1, Th2, Treg subset analysis based on transcription factor expression of all donors under the conditions described in Example 6. The results are grouped with APC induction media type at the x-axis. The legend of the graphs is shown at right. D #1: Donor #1; D #2: Donor #2; D #3: Donor #3. "IL-4 Conc." means IL-4 continuation; "IL-4 Disc." means IL-4 discontinuation.

Figure 27:
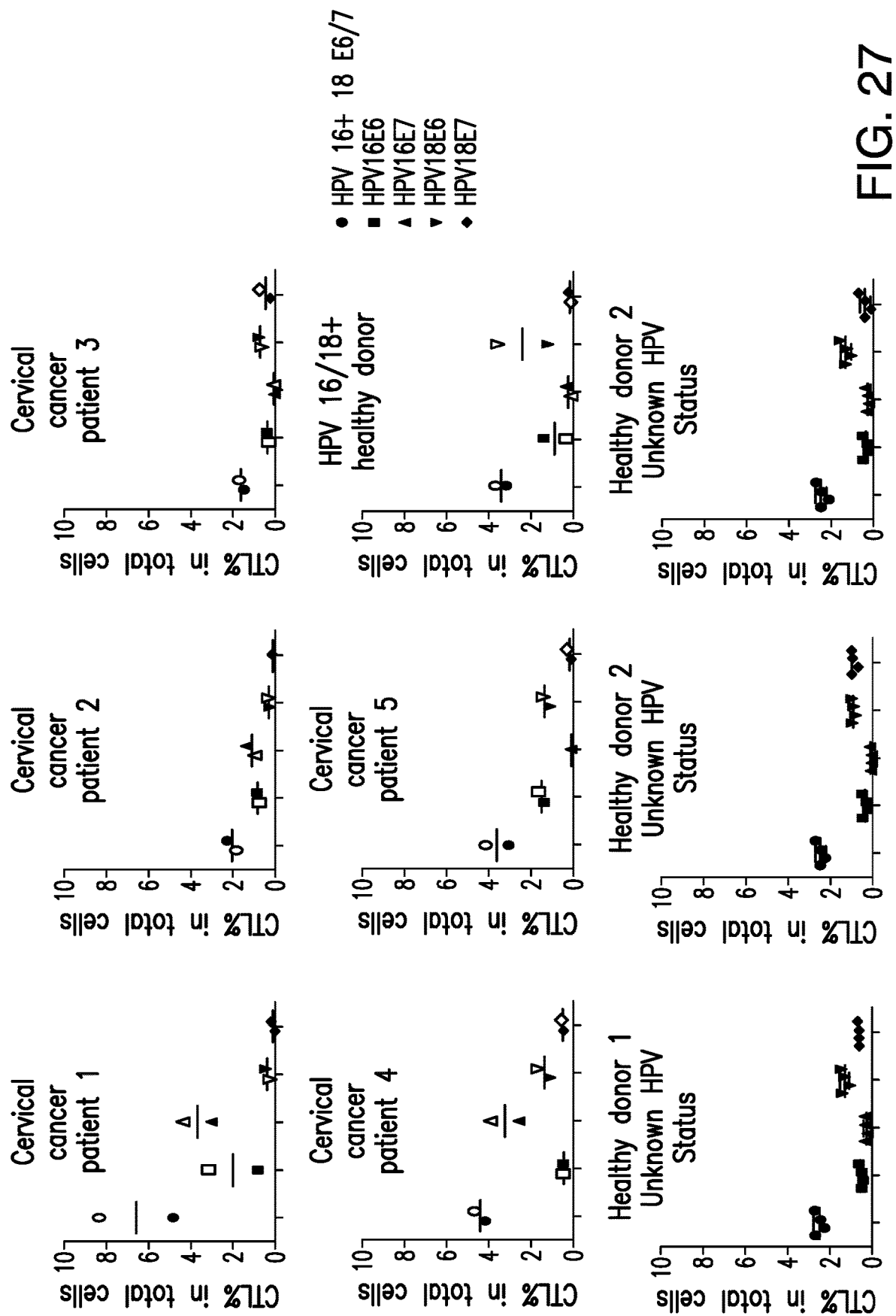

FIG. 27: T cells were generated from five cervical cancer patients, one healthy donor positive for HPV 16 and HPV 18, and three healthy donors of unknown HPV status. The T cells were than activated with HPV 16 or HPV 18 E6 or E7 antigenic peptides, or E6 and E7 antigenic peptides from both HPV 16 and HPV 18, and the percentage of T cells was measured.

FIG. 28A-B: T cells were tested for cytotoxicity against autologous targets or HLA-A2 matched targets in vitro at effector to target ratios of 2.5:1, 5:1, 10:1, 20:1, and 40:1.

Figure 29:
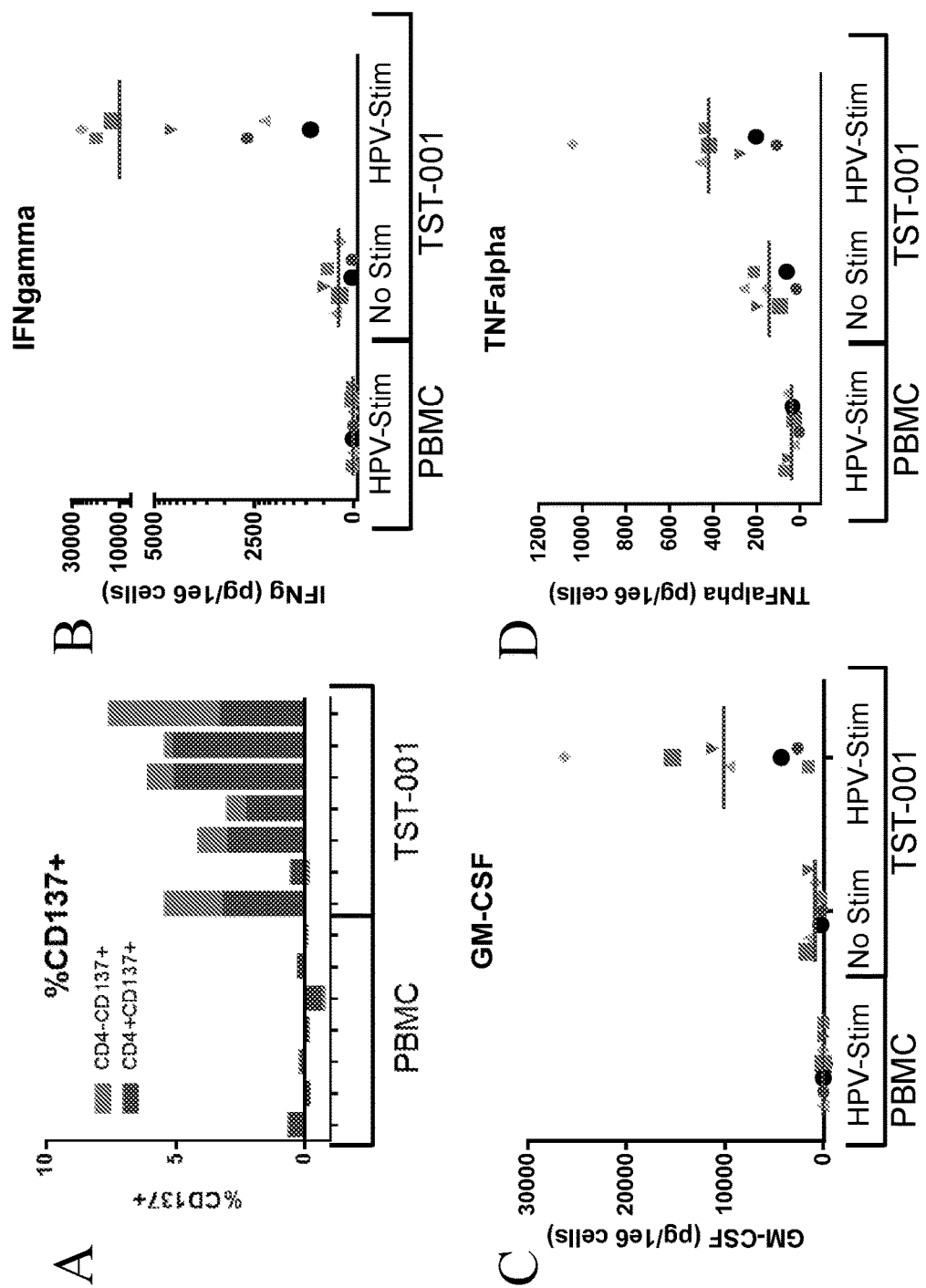

FIG. 29A-D: Cells from seven individual donors were tested before (PBMCs) and after (T cells) generation of T cells. HPV antigen specificity was tested by measuring surface expression of CD137 (FIG. 29A). Effector activity was measured in HPV-stimulated PBMCs and in HPV or non-HPV stimulated T cells by measuring secretion of IFN-γ (FIG. 29B), GM-CSF (FIG. 29C), and TNF-α, (FIG. 29D).

5. DETAILED DESCRIPTION

Provided herein are methods of generating T cells, e.g., cytotoxic T lymphocytes (T cells) starting from blood mononuclear cells, e.g., PBMCs or cord blood mononuclear cells, without a separate step of generating and isolating antigen-presenting cells, such as dendritic cells, macrophages, and B cells, and with a single round of antigen stimulation. As used herein, the term "T cells" means T lymphocytes, and includes cytotoxic T lymphocytes (T cells).

TABLE 1

List of abbreviations for key terms.

| Term | Full name |
| --- | --- |
| AE | adverse event |
| APC | antigen presenting cells |
| CBA | cytometric beads array |
| CTL | cytotoxic T lymphocytes |
| Cy | cyclophosphamide |
| DC | dendritic cells |
| DLT | dose-limiting toxicity |
| DMSO | dimethyl sulfoxide |
| Flu | fludarabine |
| GM-CSF | granulocyte-macrophage |
| HPV | Human papillomavirus |
| ICCS | intracellular cytokine staining |

TABLE 1-continued

List of abbreviations for key terms.

| Term | Full name |
|---|---|
| iDC | immature dendritic cells |
| IFN-α | interferon alpha |
| IFN-γ | interferon gamma |
| IL-10 | interleukin 10 |
| IL-13 | interleukin 13 |
| IL-15 | interleukin 15 |
| IL-1β | interleukin 1 beta |
| IL-2 | interleukin 2 |
| IL-4 | interleukin 4 |
| IL-5 | interleukin 5 |
| IL-6 | interleukin 6 |
| IL-7 | interleukin 7 |
| IM | intramuscular |
| IMDM | Iscove's Modified Dulbecco's |
| IV | intravenous |
| mDC | mature dendritic cells |
| MTD | maximum tolerated dose |
| OS | overall survival |
| PBMC | peripheral blood mononuclear |
| PBS | Phosphate-buffered saline |
| pDC | plasmacytoid DC |
| PHA | phytohemagglutinin |
| PD | progressive disease |
| PFS | progression-free survival |
| PO | orally |
| RPMI | Roswell Park Memorial Institute |
| RT | room temperature |
| SCCHN | squamous cell carcinoma of the head and neck |
| sCD40L | soluble CD40 ligand |
| TNF-α | tumor necrosis factor alpha |

5.1 Production of T Cells and T Cell Populations

In one aspect, provided herein are methods of producing a cell population comprising antigen-specific T cells, e.g., cytotoxic T lymphocytes (CTLs), comprising the steps of: (a) isolating blood mononuclear cells, e.g., PBMCs or cord blood mononuclear cells, from a subject; (b) culturing said blood mononuclear cells, e.g., PBMCs or cord blood mononuclear cells, in an antigen presenting cell (APC) induction medium comprising interleukin 4 (IL-4) and soluble CD40 ligand (sCD40L) and/or comprising granulocyte-macrophage colony-stimulating factor (GM-CSF) and interferon α (IFN-α), to produce a first population of cells; (c) culturing the first population of cells in the presence of one or more antigens, to produce a second population of cells; and (d) culturing the second population of cells in a T cell expansion medium comprising interleukin 7 (IL-7), interleukin 15 (IL-15), and, optionally, IL-4, to produce a third population of cells; wherein the third population of cells comprises T cells that are CD3+ and specific for an antigen added in step (c). In certain aspects, the method further comprises a step of culturing the third population of cells in a second T cell expansion medium comprising IL-7 and IL-15, but not comprising IL-4, to create a fourth population of cells; wherein the fourth population of cells comprises T cells that are CD3+ and specific for an antigen added in step (c). In certain aspects, the method further comprises a step of isolating T cells that are CD3+ from the third population of cells or the fourth population of cells. In certain aspects, step (c) is performed in APC induction medium. In certain aspects, the T cell expansion medium comprises IL-4. In certain aspects, the subject is a human. It certain aspects, the antigen is a human antigen. In certain aspects, the antigen is a full-length protein. In certain aspects, the antigen is a fragment of a protein. In certain aspects, the antigen is a peptide representing a part of a protein. In certain aspects, the APCs produce the antigen from exogenous genetic material. In certain aspects, one or more steps are repeated in order to increase the yield of the target population of cells generated by those one or more steps. In certain aspects, a step is repeated with cells that remain unmodified after said step. In certain aspects, one or more steps are repeated with cells that remain unmodified after said steps. In certain aspects, steps (b) to (d) are repeated one time. In certain aspects, steps (b) to (d) are repeated two times. In certain aspects, steps (b) to (d) are repeated three times. In certain aspects, steps (b) to (d) are repeated four times. In certain aspects, steps (b) to (d) are repeated five times. In certain aspects, steps (b) to (d) are repeated with blood mononuclear cells, e.g., PBMCs or cord blood mononuclear cells, remaining after step (d). In certain aspects, one or more of steps (b), (c), and (d) are repeated one, two, three, four, or five times.

In certain aspects, the third population of cells comprises T cells that are additionally CD4+. In certain aspects, the third population of cells comprises T cells that are additionally CD8+. In certain aspects, the third population of cells comprises T cells that are additionally CD4+ and CD8+.

In certain aspects, the fourth population of cells comprises T cells that are additionally CD4+. In certain aspects, the fourth population of cells comprises T cells that are additionally CD8+. In certain aspects, the fourth population of cells comprises T cells that are additionally CD4+ and CD8+.

In certain aspects, the APC induction medium comprises IL-4 and sCD40L. In certain aspects, the APC induction medium comprises 1-50 ng/mL of IL-4 and 0.1-5 μg/mL of sCD40L. In certain aspects, the APC induction medium comprises 8-12 ng/mL of IL-4 and 0.8-1.2 μg/mL of sCD40L. In certain aspects, the APC induction medium comprises 10 ng/mL of IL-4 and 1 μg/mL of sCD40L.

In certain aspects, the APC induction medium further comprises synthetic oligonucleotides with one or more unmethylated CpG dinucleotide motifs. In certain aspects, the APC induction medium further comprises GM-CSF and IFN-α. In certain aspects, the APC induction medium comprises GM-CSF and IFN-α. In certain aspects, the APC induction medium consists essentially of GM-CSF and IFN-α.

In certain aspects, the APC induction medium further comprises IMDM, 2-mercaptoethanol, Pen Strep, and/or human serum. In certain aspects, the APC induction medium further comprises RPMI-1640, Click's media, human serum, L-GLUTAMAX™ (Life Technologies), Pen Strep, and/or 2-mercaptoethanol. In certain aspects, the APC induction medium further comprises RPMI-1640, Click's media, human serum, glutamine, Pen Strep, and/or 2-mercaptoethanol.

In certain aspects, the IL-4 in the APC induction medium is at a concentration of 40 ng/mL. In certain aspects, the IL-4 in the APC induction medium is at a concentration of 10 ng/mL. In certain aspects, the CD40L in the APC induction medium is at a concentration of 1 μg/mL. In certain aspects, the CpG dinucleotide motifs in the APC induction medium are at a concentration of 4 μg/mL. In certain aspects, the GM-CSF in the APC induction medium is at a concentration of 800 U/mL. In certain aspects, the IFN-α in the APC induction medium is at a concentration of 1000 U/mL.

In certain aspects, the one or more antigens are a pool of peptides, e.g., a pool of lyophilized peptides. In certain aspects, the one or more antigens are an HPV peptide mixture, e.g., PEPMIX™. In certain aspects, the one or more antigens are a pool of overlapping 15-mers spanning E6 and E7 proteins from HPV types 16 and 18. In specific aspects, the pool of peptides cover the sequences of one or more of, or all of, human HPV16E6, HPV16E7, HPV18E6, and/or HPV18E7 proteins. In certain aspects, the one or more antigens comprise one or more antigens from a single virus, e.g., only from HPV16 or only from HPV18. In certain aspects, the peptides are at a concentration of 0.5-1 μg/mL. In specific aspects, the peptides are at a concentration of 1 μg/mL. In specific aspects, the peptides are at a concentration of 0.5 μg/mL.

In certain aspects, the T cell expansion medium comprises 10-100 ng/mL of IL-7, 2-20 ng/mL of IL-15, and 10-100 ng/mL of IL-4. In certain aspects, the T cell expansion medium comprises 40-60 ng/mL of IL-7, 7-11 ng/mL of IL-15, and 45-65 ng/mL of IL-4. In specific aspects, the T cell expansion medium comprises 50 ng/mL of IL-7, 9 ng/mL of IL-15, and 55 ng/mL of IL-4. In certain aspects, addition of the cytokines from the T cell expansion medium is performed 2 hours, 24 hours, or 48 hours after addition of the one or more antigens. In specific aspects, addition of the cytokines from the T cell expansion medium is performed 2 hours after addition of the one or more antigens. In specific aspects, addition of the cytokines from the T cell expansion medium is performed 24 hours after addition of the one or more antigens. In specific aspects, addition of the cytokines from the T cell expansion medium is performed 48 hours after addition of the one or more antigens.

In certain aspects, the T cell expansion medium comprises 1 ng/mL IL-15, 15 ng/mL IL-4, and 10 ng/mL IL-7. In certain aspects, the T cell expansion medium comprises 1 ng/mL IL-15, 15 ng/mL IL-4, and 50 ng/mL IL-7. In certain aspects, the T cell expansion medium comprises 1 ng/mL IL-15, 35 ng/mL IL-4, and 30 ng/mL IL-7. In certain aspects, the T cell expansion medium comprises 1 ng/mL IL-15, 55 ng/mL IL-4, and 10 ng/mL IL-7. In certain aspects, the T cell expansion medium comprises 1 ng/mL IL-15, 55 ng/mL IL-4, and 50 ng/mL IL-7. In certain aspects, the T cell expansion medium comprises 5.5 ng/mL IL-15, 15 ng/mL IL-4, and 10 ng/mL IL-7. In certain aspects, the T cell expansion medium comprises 5.5 ng/mL IL-15, 15 ng/mL IL-4, and 50 ng/mL IL-7. In certain aspects, the T cell expansion medium comprises 5.5 ng/mL IL-15, 35 ng/mL IL-4, and 30 ng/mL IL-7. In certain aspects, the T cell expansion medium comprises 5.5 ng/mL IL-15, 55 ng/mL IL-4, and 10 ng/mL IL-7. In certain aspects, the T cell expansion medium comprises 5.5 ng/mL IL-15, 55 ng/mL IL-4, and 50 ng/mL IL-7. In certain aspects, the T cell expansion medium comprises 10 ng/mL IL-15, 15 ng/mL IL-4, and 10 ng/mL IL-7. In certain aspects, the T cell expansion medium comprises 10 ng/mL IL-15, 15 ng/mL IL-4, and 50 ng/mL IL-7. In certain aspects, the T cell expansion medium comprises 10 ng/mL IL-15, 35 ng/mL IL-4, and 30 ng/mL IL-7. In certain aspects, the T cell expansion medium comprises 10 ng/mL IL-15, 55 ng/mL IL-4, and 10 ng/mL IL-7. In certain aspects, the T cell expansion medium comprises 10 ng/mL IL-15, 55 ng/mL IL-4, and 50 ng/mL IL-7. In certain aspects, the T cell expansion medium comprises 55 ng/mL IL-4 and 50 ng/mL IL-7. In certain aspects, the T cell expansion medium comprises 5.5 ng/mL IL-15 and 50 ng/mL IL-7. In certain aspects, the T cell expansion medium consists essentially of 5.5 ng/mL IL-15 and 50 ng/mL IL-7.

In certain aspects, the second T cell expansion medium comprises 10-100 ng/mL of IL-7 and 2-20 ng/mL of IL-15. In certain aspects, the second T cell expansion medium comprises 40-60 ng/mL of IL-7 and 7-11 ng/mL of IL-15. In specific aspects, the second T cell expansion medium comprises 50 ng/mL of IL-7 and 9 ng/mL of IL-15.

In certain aspects, the duration of step (b) is 1-3 days. In specific aspects, the duration of step (b) is 1 day. In certain aspects, the duration of step (d) is 8-16 days. In specific aspects, the duration of step (d) is 12 days. In certain aspects, IL-4 is removed from the T cell expansion medium prior to the end of T cell expansion. In certain aspects, IL-4 is not removed from the T cell expansion medium prior to the end of T cell expansion.

In certain aspects, the blood mononuclear cells, e.g., PBMCs, are isolated from whole blood, buffy coat, or an enriched leukapheresis product. In certain aspects, the blood mononuclear cells, e.g., PBMCs or cord blood mononuclear cells, are seeded into the APC induction medium at a density of $4\text{-}6 \times 10^6/\text{cm}^2$. In specific aspects, the blood mononuclear cells, e.g., PBMCs or cord blood mononuclear cells, are seeded at a density of $5 \times 10^6/\text{cm}^2$. In specific aspects, the blood mononuclear cells, e.g., PBMCs or cord blood mononuclear cells, are seeded at a density greater than $5 \times 10^6/\text{cm}^2$.

In certain aspects, the antigen-specific CD3+ cells are identified by intracellular cytokine staining (ICCS). In certain aspects, the culturing steps are performed in a gas-permeable container, e.g., plastic bag or a G-REX® device. In certain aspects, one or more culturing steps are performed in T-flasks. In certain aspects, one or more culturing steps are performed in bags. In specific aspects, the bags are static bags. In certain aspects, the bags are gas-permeable. In certain aspects, one or more culturing steps are performed in a WAVE™ bioreactor. In certain aspects, one or more culturing steps are performed in a spinner flasks.

5.2 Isolation and Characterization of T Cells

Methods of isolating T cells are known in the art and can be used to isolate (e.g., purify) the T cells produced using the methods described herein. For example, T cells can be isolated or enriched by staining cells, in one embodiment, with antibodies to CD3, and selecting for CD3+ cells. T cells may also be isolated with antibodies to CD4 and/or CD8, and selecting for CD4+ and/or CD8+ cells. T cells, for example, T cells produced by the methods described herein can also be isolated or enriched by removal of cells other than T cells in a population of cells that comprise the T cells, e.g., T cells produced by the methods described herein. For example, T cells, e.g., cells produced using the methods described herein, may be isolated or enriched by depletion of cells displaying non-T cell markers. Cells isolated by these methods may be additionally sorted.

Antigen-specific T cells, e.g., antigen-specific CTLs, e.g. HPV-specific T cells and CTLs, may, for example, be identified using an ICCS assay, a flow cytometry based assay which detects the production and accumulation of cytokines within the endoplasmic reticulum after cell stimulation. ICCS can be used in combination with other flow cytometry protocols for immunophenotyping using cell surface markers to detect antigen reactivity of T cells. In specific embodiments, a ICCS assay is used to measure antigen-specific T cell, e.g., HPV-T cell, frequency at various time points of the culture process of the T cells. ICCS works via the following principles: 1) antigen specific T cells can be activated by the same specific antigen re-stimulation, 2) in response to the antigen specific re-stimulation, T cell can produce cytokines (such as IFN-γ, TNF-α, IL-2, et al) and express activation markers (such as CD154, CD137, et al), 3) an inhibitor of protein transport (e.g. brefeldin A) is added during the re-stimulation to retain the cytokines within the cell, 4) the cells are then fixed in paraformaldehyde and permeabilized, and 5) the anti-cytokine antibody is added and the cells can be analyzed by flow cytometer.

As T cells will activate in response to a wide variety of stimulatory signals in addition to the antigen specific stimulation, positive staining (especially low intensity staining) does not unequivocally demonstrate true antigen specificity when using ICCS. Thus, in one embodiment, a non-antigen stimulation control is set up along with the specific antigen stimulation conditions. The antigen-specific, e.g., HPV, T cell number is counted by measuring the T cells that have at least one of the cytokine production or up-regulated activation markers, and subtracting the number from the non-antigen stimulation control. In certain embodiments, the panel used for flow cytometry is a 6 marker panel, including CD3, CD4, CD8, CD154 (CD40L), IFN-γ and TNF-α. CD3, CD4 and CD8 are T cell lineage markers that can define a total T cell population, optionally including natural killer T (NKT) cells, and CD4/CD8 T cell ratio. IFN-γ and TNF-α are cytokines that T cells produce after overnight re-activation. CD154 is a T cell activation marker that is up-regulated in newly antigen-activated T cells.

Determination and/or isolation of T cells may be performed, for example, using a T cell purity panel comprising antibodies against CD19, CD56, CD3, CD11a, CD4, and CD8. Determination and/or isolation of T cells at a certain stage of differentiation may be performed using a T cell differentiation panel comprising antibodies against CD3, CD62L, CD4, CD27, CCR7, and CD45RO. To determine whether cells comprise T cells, secreted cytokines can also be measured, for example, by an 8-plex cytometrix beads array (CBA). The panel may include one or more sets of cytokines selected from the group consisting of Th1 cytokines (e.g., IL-2, IFN-γ and TNF-α), Th2 cytokines (e.g., IL-5, IL-13), Treg cytokines (e.g., IL-10), and T cell effector function related cytokines (e.g., Granzyme B and GM-CSF). To determine whether cells comprise T cells, transcription factors may be measured, for example, one or more of T-bet, GATA-3, and FoxP3.

Cell separation, e.g., separating T cells produced by the methods described herein from non-T cells, can be accomplished by, e.g., flow cytometry, fluorescence-activated cell sorting (FACS), or, in one embodiment, magnetic cell sorting using microbeads conjugated with specific antibodies. The cells may be isolated, e.g., using a magnetic activated cell sorting (MACS) technique, a method for separating particles based on their ability to bind magnetic beads (e.g., about 0.5-100 μm diameter) that comprise one or more specific antibodies, e.g., anti-CD3 antibodies. Magnetic cell separation can be performed and automated using, e.g., an AUTOMACS™ Separator (Miltenyi) or a CLINIMACS® System (Miltenyi). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then be isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

5.3 T Cells and Populations of T Cells

In one aspect, provided herein are populations of antigen-specific T cells that are specific for a specific antigen or a set of related antigens, e.g., specific to antigens from the same protein. In one aspect, provided herein are populations of antigen-specific T cells that are specific for a set of unrelated antigens, e.g., specific to antigens from different proteins. In certain embodiments, the T cells are produced by the method comprising the steps of: (a) isolating blood mononuclear cells, e.g., PBMCs or cord blood mononuclear cells, from a subject; (b) culturing said blood mononuclear cells, e.g., PBMCs or cord blood mononuclear cells, in an antigen presenting cell (APC) induction medium comprising interleukin 4 (IL-4) and soluble CD40 ligand (sCD40L) and/or comprising granulocyte-macrophage colony-stimulating factor (GM-CSF) and interferon α (IFN-α), to produce a first population of cells; (c) culturing the first population of cells in the presence of one or more antigens, to produce a second population of cells; and (d) culturing the second population of cells in a T cell expansion medium comprising interleukin 7 (IL-7), interleukin 15 (IL-15), and IL-4, to produce a third population of cells; wherein the third population of cells comprises T cells that are CD3+ and specific for an antigen added in step (c). In certain aspects, the populations of cells are produced by a method which further comprises a step of culturing the third population of cells in a second T cell expansion medium comprising IL-7 and IL-15, but not comprising IL-4, to create a fourth population of cells; wherein the fourth population of cells comprises T cells that are CD3+ and specific for an antigen added in step (c). In certain aspects, the populations of cells are produced by a method which further comprises a step of isolating T cells that are CD3+ from the third population of cells or the fourth population of cells. In certain aspects, the populations of cells are produced by a method wherein step (c) is performed in APC induction medium.

In certain aspects, the third population of cells comprises T cells that are additionally CD4+. In certain aspects, the third population of cells comprises T cells that are additionally CD8+. In certain aspects, the third population of cells comprises T cells that are additional CD4+ and CD8+.

In certain aspects, the fourth population of cells comprises T cells that are additionally CD4+. In certain aspects, the fourth population of cells comprises T cells that are additionally CD8+. In certain aspects, the fourth population of cells comprises T cells that are additionally CD4+ and CD8+.

In certain aspects, the APC induction medium comprises IL-4 and sCD40L. In certain aspects, the APC induction medium comprises 8-12 ng/mL of IL-4 and 0.8-1.2 μg/mL of sCD40L. In certain aspects, the APC induction medium comprises 10 ng/mL of IL-4 and 1 μg/mL of sCD40L.

In certain aspects, the one or more antigens are, or are comprised within, a pool of peptides, e.g., lyophilized peptides. Preferably, the peptides are each derived from, e.g., represent a portion of, a sequence of a protein against which the T cells are to be activated. In certain embodiments, the peptides are 10-mers, 11-mers, 12-mers, 13-mers, 14-mers, 15-mers, 16-mers, 17-mers, 18-mers, 19-mers or 20-mers. In certain embodiments, the pool of peptides are non-overlapping across a specific protein sequence from which they are derived. In certain other embodiments, the pool of peptides are overlapping across a specific protein sequence from which they are derived. In specific embodiments, such peptides may successively overlap by 1, 2, 3, 4, 5, 6, 7, 8, 9, 10, 11, 12, 13, 14, 15, 16, 17, 18, 19, 20, 21, 22, 23, 24, or 25 amino acids. In certain embodiments, the protein is a Tumor-Associated Antigen (TAA). In other embodiments, the protein is a Tumor-Specific Antigen (TSA). In specific aspects, the peptides cover the sequences of human HPV16E6, HPV16E7, HPV18E6, and/or HPV18E7 proteins. In certain aspects, such peptides comprise every amino acid residue present in human HPV16E6, HPV16E7, HPV18E6, and/or HPV18E7 proteins. In certain aspects, such peptides comprise a portion of the amino acid residues present in human HPV16E6, HPV16E7, HPV18E6, and/or HPV18E7 proteins. In a specific embodiment, the peptides cover the sequences of human HPV16E6, HPV16E7, HPV18E6, and HPV18E7 proteins. In a specific embodiment, the peptides cover the sequences of human HPV16E6 and/or HPV16E7 proteins and do not cover HPV18E6, and/or HPV18E7 proteins. In another specific embodiment, the peptides cover the sequences of human HPV18E6 and/or HPV18E7 proteins and do not cover HPV16E6, and/or HPV16E7 proteins. In specific aspects, the peptides are at a concentration of 1 µg/mL. In certain aspects, the one or more antigens are produced from exogenous genetic material by the APCs.

In certain embodiments, the antigen is selected from the group consisting of B-cell maturation antigen (BCMA), IL13Rα2, Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD19, CD34, CD45, CD99, CD117, chromogranin, cytokeratin, desmin, glial fibrillary acidic protein (GFAP), gross cystic disease fluid protein (GCDFP-15), HMB-45 antigen, high molecular weight melanoma-associated antigen (HMW-MAA), protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, an abnormal p53 protein, fuc-GM1, GM2 (oncofetal antigen-immunogenic-1; OFA-I-1); GD2 (OFA-I-2), GM3, GD3, alpha-actinin-4, Bage-1, BCR-ABL, Bcr-Abl fusion protein, beta-catenin, CA 15-3 (CA 27.29\BCAA), CA 195, CA 242, CA-50, CAM43, Casp-8, cdc27, cdk4, cdkn2a, coa-1, dek-can fusion protein, EBNA, EF2, Epstein Barr virus antigens, ETV6-AML1 fusion protein, HLA-A2, HLA-A11, hsp70-2, KIAA0205, Mart2, Mum-1, 2, and 3, neo-PAP, myosin class I, OS-9, pml-RARα fusion protein, PTPRK, triosephosphate isomerase, Gage 3,4,5,6,7, GnTV, Herv-K-mel, Lage-1, NA-88, NY-Eso-1/Lage-2, SP17, SSX-2, TRP2-Int2, gp100 (Pmel 17), tyrosinase, TRP-1, TRP-2, MAGE-1, MAGE-3, RAGE, GAGE-1, GAGE-2, p15(58), RAGE, SCP-1, Horn/Niel-40, PRAME, HER-2/neu, E2A-PRL, H4-RET, IGH-IGK, MYL-RAR, human papillomavirus (HPV) antigens E6 and E7, TSP-180, p185erbB2, p180erbB-3, c-met, nm-23H1, PSA, TAG-72-4, CA 19-9, CA 72-4, CAM 17.1, NuMa, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90, TAAL6, TAG72, TLP, TPS, CD19, CD22, CD27, CD30, CD70, EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), integrin αvβ3 (CD61), galactin, and Ral-B.

In certain embodiments, the antigen is a tumor-associated antigen or a tumor-specific antigen. In various specific embodiments, without limitation, the tumor-associated antigen or tumor-specific antigen is Her2, prostate stem cell antigen (PSCA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD19, CD34, CD45, CD99, CD117, chromogranin, cytokeratin, desmin, glial fibrillary acidic protein (GFAP), gross cystic disease fluid protein (GCDFP-15), HMB-45 antigen, high molecular weight melanoma-associated antigen (HMW-MAA), protein melan-A (melanoma antigen recognized by T lymphocytes; MART-1), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein.

In certain embodiments, the TAA or TSA is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXB1, SPA17, SSX, SYCP1, or TPTE.

In certain other embodiments, the TAA or TSA is a carbohydrate or ganglioside, e.g., fuc-GM1, GM2 (oncofetal antigen-immunogenic-1; OFA-I-1); GD2 (OFA-I-2), GM3, GD3, and the like.

In certain other embodiments, the TAA or TSA is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-A11, hsp70-2, KIAA0205, Mart2, Mum-1, 2, and 3, neo-PAP, myosin class I, OS-9, pml-RARα fusion protein, PTPRK, K-ras, N-ras, triosephosphate isomerase, Gage 3,4, 5,6,7, GnTV, Herv-K-mel, Lage-1, NA-88, NY-Eso-1/Lage-2, SP17, SSX-2, TRP2-Int2, gp100 (Pmel 17), tyrosinase, TRP-1, TRP-2, MAGE-1, MAGE-3, RAGE, GAGE-1, GAGE-2, p15(58), RAGE, SCP-1, Hom/Mel-40, PRAME, p53, H-Ras, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90, TAAL6, TAG72, TLP, TPS, CD19, CD22, CD27, CD30, CD70, GD2 (ganglioside G2), EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein. In another specific embodiment, said tumor-associated antigen or tumor-specific antigen is integrin αvβ3 (CD61), galactin, K-Ras (V-Ki-ras2 Kirsten rat sarcoma viral oncogene), or Ral-B. Other tumor-associated and tumor-specific antigens are known to those in the art.

In certain specific embodiments, the antigen is an antigen not considered to be a TSA or a TAA, but is nevertheless associated with tumor cells, or damage caused by a tumor. In certain specific embodiments, the antigen is a neoantigen. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1α, HIF-1β, HIF-2α, HIF-2β, HIF-3α, or HIF-3β. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

In certain embodiments, the antigen is virus-associated, e.g., HPV associated. In specific embodiments, the antigen is HPV associated. In specific embodiments, the antigen is EBV associated.

In certain aspects, the T cell expansion medium comprises 40-60 ng/mL of IL-7, 7-11 ng/mL of IL-15, and 45-65 ng/mL of IL-4. In specific aspects, the T cell expansion medium comprises 50 ng/mL of IL-7, 9 ng/mL of IL-15, and 55 ng/mL of IL-4.

In certain aspects, the second T cell expansion medium comprises 40-60 ng/mL of IL-7 and 7-11 ng/mL of IL-15. In specific aspects, the second T cell expansion medium comprises 50 ng/mL of IL-7 and 9 ng/mL of IL-15.

In certain aspects, the duration of step (b) is 1-3 days. In specific aspects, the duration of step (b) is 1 day. In certain aspects, the duration of step (d) is 8-16 days. In specific aspects, the duration of step (d) is 12 days.

In certain aspects, the blood mononuclear cells, e.g., PBMCs, are isolated from whole blood, buffy coat, or an enriched leukapheresis product. In certain aspects, the blood mononuclear cells, e.g., PBMCs or cord blood mononuclear cells, are seeded in the APC induction medium at a density of 4-6×10$^6$/cm$^2$. In specific aspects, the blood mononuclear cells, e.g., PBMCs or cord blood mononuclear cells, are seeded at a density of 5×10$^6$/cm$^2$. In specific aspects, the blood mononuclear cells, e.g., PBMCs or cord blood mononuclear cells, are seeded at a density greater than 5×10$^6$/cm$^2$.

In certain aspects, the antigen-specific CD3+ cells are identified by intracellular cytokine staining (ICCS). In certain aspects, the culturing steps are performed in a G-REX® device. In certain aspects, one or more culturing steps are performed in T-flasks. In certain aspects, one or more culturing steps are performed in bags. In specific aspects, the bags are static bags. In certain aspects, the bags are gas-permeable. In certain aspects, one or more culturing steps are performed in a WAVE™ bioreactor. In certain aspects, one or more culturing steps are performed in a spinner flasks.

In certain aspects, the APC induction medium further comprises synthetic oligonucleotides with unmethylated CpG dinucleotide motifs. In certain aspects, the APC induction medium further comprises GM-CSF and IFN-α. In certain aspects, the APC induction medium comprises GM-CSF and IFN-α.

In a specific embodiment, said T cell population comprises about 70% or more, in some embodiments, 75%, 80%, 85%, 90%, 95%, 98%, or 99% CD3+ cells. In another specific embodiment, said T cell population comprises no less than 80%, 85%, 90%, 95%, 98%, or 99% CD3+ cells. In another specific embodiment, said T cell population comprises between 70%-75%, 75%-80%, 80%-85%, 85%-90%, 90%-95%, or 95%-99% CD3+ cells.

In certain embodiments, said CD3+ cells in said T cell population comprise CD3+ cells that are additionally CD4+. In certain embodiments, said CD3+ cells in said T cell population comprise CD3+ cells that are additionally CD8+. In certain embodiments, said CD3+ cells in said T cell population comprise CD3+ cells that are additionally CD4+ and CD8+. In certain embodiments, said T cell population comprises CD137+ cells. In certain embodiments, said T cell population comprises CD154+ cells. In certain embodiments, said T cell population comprises cells that express Th1 cytokines. In certain embodiments, said T cell population comprises cells that express IFN-γ. In certain embodiments, said T cell population comprises cells that express TNF-α. In certain embodiments, said T cell population comprises cells that express GM-CSF. In certain embodiments, said T cell population comprises cells that express granzyme B. In certain embodiments, said T cell population comprises CD3+, CD137+, and CD154+ cells. In certain embodiments, said T cell population comprises CD3+, CD4+, CD137+, and CD154+ cells. In certain embodiments, said T cell population comprises CD3+, CD8+, CD137+, and CD154+ cells. In certain embodiments, said T cell population comprises CD3+, CD4+, CD8+, CD137+, and CD154+ cells. In certain embodiments, said T cell population comprises CD3+, CD137+, CD154+ cells, and cells that express one or more Th1 cytokines. In certain embodiments, said T cell population comprises CD3+, CD4+, CD137+, CD154+ cells, and cells that express one or more Th1 cytokines. In certain embodiments, said T cell population comprises CD3+, CD8+, CD137+, CD154+ cells, and cells that express one or more Th1 cytokines. In certain embodiments, said T cell population comprises CD3+, CD4+, CD8+, CD137+, CD154+ cells, and cells that express one or more Th1 cytokines.

In certain embodiments, T cells, e.g., the T cells produced by any of the methods disclosed herein, e.g., T cells that are HPV-specific, show increased expression of one or more genes as compared to PBMCs, e.g., matched PBMCs, from which they are produced, wherein said one or more genes are one or more of ACSL5, ACSL6, ACTA2, AHRR, ALDH18A1, ALDH6A1, ANAPC11, AP2B1, BAX, BCL6, BRCA1, C5, CCL13, CCL17, CCL18, CCL20, CCL22, CCL4, CCNA1, CCNA2, CCNB1, CCNB2, CCND3, CCNE2, CD40LG, CD80, CD86, CDC20, CDC25A, CDC25A, CDC25C, CDC45, CDC6, CDK1, CDK1, CDK2, CDK2, CDK4, CDK5, CDK6, CDT1, CHEK2, CKLF, COPG2, CXADR, CXCL16, CXCL2, CXCL8, CXCR5, CXCR5, CYB5A, CYP1A1, CYP1B1, DHFR, E2F1, ESPL1, FADS1, FADS2, FAS, FBX05, FGFR1, FGFR1, FLOT1, FN1, FOS, FYN, FYN, GADD45B, GALK1, GALK2, GMDS, GMPPA, GSTA4, GSTM4, HLA-DMB, HLA-DQA1, HLA-DQB1, HLA-DRA, IFNGR1, IL12RB1, IL12RB2, IL13, IL1B, IL1B, IL21R, IL2RA, IL2RG, IL4, IL5, IL6ST, IRS2, IRS2, ITGA1, ITGA4, ITGA5, ITGA6, ITGAL, ITGAX, ITGB1, ITGB7, JAM3, JUN, KIF11, KIF23, MAP3K2, MCM2, MCM3, MCM4, MCM5, MGST2, MGST3, MMP25, MYL6B, NQ01, NQ02, NRIP1, PCNA, PHGDH, PIK3C2A, PIK3CA, PLK2, PLK3, PLK4, POLA1, PPM1L, PPP2R3B, PRC1, PRIM1, PRKD3, PSAT1, PSPH, PTTG1, RAC2, RAC3, RAD50, RAD51, RARA, RBBP8, RRAS, SDC4, SELPLG, SHMT1, SHMT2, SLC27A2, SMC2, STAT1, TFDP1, TGFB1, TGFBR2, TGM2, TOP2A, TSTA3, UGDH, XCL1, XCL2, ZEB1, and/or ZNF420. In certain embodiments, the increased expression is 5-fold, 10-fold, 15-fold, 20-fold, 25-fold, 30-fold, 40-fold, 50-fold, 60-fold, 70-fold, 80-fold, 90-fold, 100-fold or more. In certain other embodiments, T cells, e.g., the T cells produced by any of the methods disclosed herein, e.g., T cells that are HPV-specific, show increased expression of one or more genes as compared to upulsed cells that have otherwise been produced by the methods described herein (that is, T cells not exposed to a PepMix), wherein said one or more genes are one or more of CCL18 (chemokine (C-C motif) Ligand 18); CH13L1 (Chitinase-3-like protein); FN1 (Fibronectin 1); LYZ (Lysozyme); RCHY1 (Ring finger and CHY zinc finger 1); and PALLD (Palladin, cytoskeletal associated protein). Such T cells may be used in, e.g., any of the methods of treatment described herein.

5.4 Compositions Comprising T Cells

In some embodiments, provided herein is a composition, e.g., a pharmaceutical composition, comprising a T cell population produced using the methods described herein. In a specific embodiment, said T cell population comprises at least 50% of cells in the composition. In another specific embodiment, said T cell population, e.g., CD3+ cells, comprises at least 80%, 85%, 90%. 95%, 98% or 99% of cells in the composition. In certain embodiments, no more than 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, or 45% of the cells in said T cell population are CD3+ cells. In certain embodiments, said CD3+ cells are CD4+ and/or CD8+. In certain embodiments, said CD3+ cells are CD137+. In certain embodiments, said CD3+ cells are CD154+. In certain embodiments, said CD3+ cells express Th1 cytokines. In certain embodiments, said CD3+ cells express IFN-γ. In certain embodiments, CD3+ cells express TNF-α. In certain embodiments, CD3+ cells express GM-CSF. In certain embodiments, CD3+ cells express granzyme B. In certain embodiments, said CD3+ cells are CD137+ and CD154+. In certain embodiments, said CD3+ cells are CD4+, CD137+, and CD154+. In certain embodiments, said CD3+ cells are CD8+, CD137+, and CD154+. In certain embodiments, said CD3+ cells are CD4+, CD8+, CD137+, and CD154+. In certain embodiments, said CD3+ cells are CD137+, CD154+, and express one or more Th1 cytokines. In certain embodiments, said CD3+ cells are CD4+, CD137+, CD154+, and express one or more Th1 cytokines. In certain embodiments, said CD3+ cells are CD8+, CD137+, CD154+, and express one or more Th1 cytokines. In certain embodiments, said CD3+ cells are CD4+, CD8+, CD137+, CD154+, and express one or more Th1 cytokines.

In a specific embodiment, said T cells in said composition are from the same individual as the individual for whom reintroduction of, e.g., treatment with, the T cells is intended (i.e., the T cells are autologous to the intended recipient). In another specific embodiment, said T cells in said composition are from a different individual than the individual for whom reintroduction of, e.g., treatment with, the T cells is intended (i.e., the T cells are not autologous to the intended recipient). In another specific embodiment, said composition additionally comprises an immunomodulatory compound or thalidomide. In certain embodiments, the immunomodulatory compound is a compound described below. See, e.g., U.S. Pat. No. 7,498,171, the disclosure of which is hereby incorporated by reference in its entirety. In certain embodiments, the immunomodulatory compound is an aminosubstituted isoindoline. In one embodiment, the immunomodulatory compound is 3-(4-amino-1-oxo-1,3-dihydroisoindol-2-yl)-piperidine-2,6-dione; 3-(4'aminoisolindoline-1'-one)-1-piperidine-2,6-dione; 4-(amino)-2-(2,6-dioxo(3-piperidyl))-isoindoline-1,3-dione; or 4-Amino-2-(2,6-dioxopiperidin-3-yl)isoindole-1,3-dione. In another embodiment, the immunomodulatory compound is pomalidomide, or lenalidomide. In another embodiment, said immunomodulatory compound is a compound having the structure

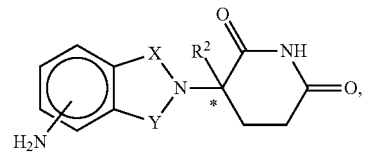

wherein one of X and Y is C=O the other of X and Y is C=O or $CH_2$, and $R^2$ is hydrogen or lower alkyl, or a pharmaceutically acceptable salt, hydrate, solvate, clathrate, enantiomer, diastereomer, racemate, or mixture of stereoisomers thereof. In another embodiment, said immunomodulatory compound is a compound having the structure

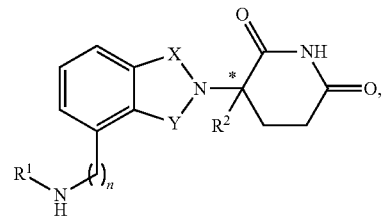

wherein one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, C(O)$R^3$, C(S)$R^3$, C(O)O$R^4$, $(C_1-C_8)$alkyl-N$(R^6)_2$, $(C_1-C_8)$alkyl-O$R^5$, $(C_1-C_8)$alkyl-C(O)O$R^5$, C(O)NH$R^3$, C(S)NH$R^3$, C(O)N$R^3R^{3'}$, C(S)N$R^3R^{3'}$ or $(C_1-C_8)$alkyl-O(CO)$R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-N$(R^6)_2$, $(C_1-C_8)$alkyl-O$R^5$, $(C_1-C_8)$alkyl-C(O)O$R^5$, $(C_1-C_8)$alkyl-O(CO)$R^5$, or C(O)O$R^5$;

$R^4$ is $(C_1-C_8)$alkyl, $(C_2-C_8)$alkenyl, $(C_2-C_8)$alkynyl, $(C_1-C_4)$alkyl-O$R^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)O—$R^5$ or the $R^6$ groups can join to form a heterocycloalkyl group;

n is 0 or 1; and

\* represents a chiral-carbon center;

or a pharmaceutically acceptable salt, hydrate, solvate, clathrate, enantiomer, diastereomer, racemate, or mixture of stereoisomers thereof. In another embodiment, said immunomodulatory compound is a compound having the structure

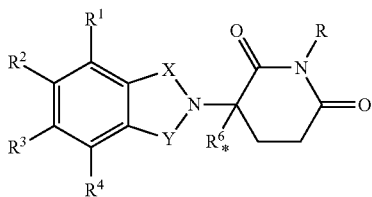

wherein:
one of X and Y is C=O and the other is CH$_2$ or C=O;
R is H or CH$_2$OCOR';
(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, or R$^4$ is nitro or —NHR$^5$ and the remaining of R$^1$, R$^2$, R$^3$, or R$^4$ are hydrogen;
R$^5$ is hydrogen or alkyl of 1 to 8 carbons
R$^6$ hydrogen, alkyl of 1 to 8 carbon atoms, benzo, chloro, or fluoro;
R' is R7-CHR$^{10}$—N(R$^8$R$^9$);
R$^7$ is m-phenylene or p-phenylene or —(C$_n$H$_{2n}$)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$_1$CH$_2$CH$_2$— in which X$_1$ is —O—, —S—, or —NH—;
R$^{10}$ is hydrogen, alkyl of to 8 carbon atoms, or phenyl; and
* represents a chiral-carbon center;
or a pharmaceutically acceptable salt, hydrate, solvate, clathrate, enantiomer, diastereomer, racemate, or mixture of stereoisomers thereof.

In another specific embodiment, the composition additionally comprises one or more anticancer compounds, e.g., one or more of the anticancer compounds described below. In another specific embodiment, the composition additionally comprises an immunomodulatory drug or an epigenetic modifier. In another specific embodiment, the composition comprises an immune checkpoint inhibitor. In more specific embodiments, the immune checkpoint inhibitor is selected from the group consisting of an anti-CTLA-4 antibody, an anti-PD1 antibody, and an anti-PD-L1 antibody.

In certain embodiments, the antigen-specific T cells are formulated in a pharmaceutically-acceptable solution. In preferred embodiments, the pharmaceutically-acceptable solution is suitable for the delivery of living cells. In specific embodiments, the pharmaceutically-acceptable solution is, for example, saline solution (such as Ringer's solution), gelatins, carbohydrates (e.g., lactose, amylose, starch, or the like), fatty acid esters, hydroxymethylcellulose, or polyvinyl pyrolidine. In more specific embodiments, the pharmaceutically-acceptable solution is sterilized prior to addition of the cells. In other more specific embodiments, the pharmaceutically-acceptable solution may be mixed with auxiliary agents such as lubricants, preservatives, stabilizers, emulsifiers, salts for influencing osmotic pressure, buffers, and coloring. Pharmaceutical carriers suitable for use in formulating the cells are known in the art and are described, for example, in WO 96/05309. In specific embodiments, the pharmaceutically-acceptable solution comprises one or more of dextran-40, human serum albumin, Plasma Lyte A, sodium chloride, and dimethyl sulfoxide. In certain embodiments, the antigen-specific T cells are formulated in a solution with a cryoprotectant. In specific embodiments, the cryoprotectant is dimethyl sulfoxide (DMSO).

In certain embodiments, the antigen-specific T cells produced by the methods described herein are provided in one or more infusion bags.

5.5 Uses of Antigen-Specific T Cells

In certain embodiments, provided herein are methods of treating a cancer or a viral infection comprising administering to a patient in need thereof a population of antigen-specific T cells produced by the methods described herein, e.g., from isolated blood mononuclear cells, e.g., PBMCs or cord blood mononuclear cells. In certain embodiments, the isolated blood mononuclear cells, e.g., PBMCs or cord blood mononuclear cells, are autologous to the patient. In certain embodiments, the isolated blood mononuclear cells, e.g., PBMCs or cord blood mononuclear cells, are not autologous to the patient.

The antigen-specific T cells produced using the methods described herein can be used in methods of treating individuals having cancer, e.g., individuals having solid tumor cells and/or blood cancer cells, or persons having a viral infection. The antigen-specific T cells produced using the methods described herein can also be used in methods of treating individuals at risk of developing, or to prevent the development of, cancer.

5.5.1 Treatment of Individuals Having Cancer

In one embodiment, provided herein is a method of treating an individual having a cancer, for example, a blood cancer or a solid tumor, comprising administering to said individual a therapeutically effective amount of antigen-specific T cells produced using the methods described herein. In one embodiment, provided herein is a method of treating an individual at risk of developing cancer, for example, a blood cancer or a solid tumor, comprising administering to said individual a therapeutically effective amount of antigen-specific T cells produced using the methods described herein. In specific embodiments, the T cells are specific to an antigen expressed by the cancer. In more specific embodiments, the T cells are specific to one or more of the tumor-associated antigens or tumor-specific antigens disclosed in Section 5.3, above. In certain embodiments, the T cells are antigen-specific T cells produced by any of the methods described herein. In certain embodiments, the individual has a deficiency of T cells, e.g., a deficiency of T cells active against the individual's cancer. In certain embodiments, the individual has too few T cells. In certain embodiments, the individual has T cells with suppressed activity. As used herein, an "effective amount" is an amount that, e.g., results in a detectable improvement of, lessening of the progression of, or elimination of, one or more symptoms of a cancer from which the individual suffers.

In specific aspects, the individual has primary ductal carcinoma, leukemia, acute T cell leukemia, chronic myeloid lymphoma, acute myelogenous leukemia, multiple myeloma, chronic myelogenous leukemia, lung carcinoma, colon adenocarcinoma, histiocytic lymphoma, multiple myeloma, retinoblastoma, or colorectal carcinoma.

In certain embodiments, provided herein are methods of treating an individual having an HPV positive (HPV+) cancer. In specific embodiments, the HPV+ cancer is head and neck cancer. In more specific embodiments, the HPV+ cancer is squamous cell carcinoma of the head and neck (SCCHN). In specific embodiments, the HPV+ cancer is oropharyngeal cancer. In certain aspects, the HPV+ cancer is penile cancer. In certain aspects, the HPV+ cancer is cervical cancer. In certain aspects, the HPV+ cancer is anal cancer. In certain aspects, the HPV+ cancer is vulval cancer. In certain aspects, the HPV+ cancer is vaginal cancer. In certain aspects, the HPV+ cancer is lung cancer. In specific embodiments, the HPV+ cancer is HPV-16+. In specific embodiments, the HPV+ cancer is HPV-18+. In specific embodiments, the HPV+ cancer is HPV-16+ and HPV-18+. In certain embodiments, the HPV+ cancer is metastatic. In certain embodiments, the HPV+ cancer is recurrent. In certain embodiments, the HPV+ cancer is metastatic and recurrent. In certain embodiments, provided herein are methods of treating an individual who has an HPV+ cancer, as determined by immunohistochemistry. In certain embodiments, provided herein are methods of treating an individual who has an HPV+ cancer, as determined by polymerase chain reaction. In certain embodiments, provided herein are methods of treating an individual who has an HPV+ cancer, as determined by RNA fluorescence in situ hybridization. In certain embodiments, provided herein are methods of treating an individual with an HPV+ cancer who has been previously treated with cetuximab. In certain embodiments, provided herein are methods of treating an individual with an HPV+ cancer who has been previously treated with a platinum-based doublet. In certain embodiments, provided herein are methods of treating an individual with an HPV+ cancer who has been previously treated with cetuximab and a platinum-based doublet. In certain embodiments, the platinum based doublet is cisplatin/5-FU. In certain embodiments, the platinum based doublet is carboplatin/5-FU. In certain embodiments, provided herein are methods of treating an individual with an HPV+ cancer who has been previously treated with a PD-1 inhibitor. In certain embodiments, the PD-1 inhibitor is pembrolizumab (KEYTRUDA®; Merck). In certain embodiments, the PD-1 inhibitor is nivolumab (OPDIVO®; Bristol-Myers Squibb). In certain embodiments, provided herein are methods of treating an individual with an HPV+ cancer who has been previously treated with a PD-L1 inhibitor. In certain embodiments, the PD-L1 inhibitor is durvalumab (MedImmune).

In certain aspects, the method further comprises administering to any of the above said individuals an immunomodulatory drug or an epigenetic modifier. In specific aspects, the method further comprises administering to said individual an immune checkpoint inhibitor. In more specific aspects, the immune checkpoint inhibitor is selected from the group consisting of an anti-CTLA-4 antibody, an anti-PD1 antibody, and an anti-PD-L1 antibody. In certain embodiments, the PD-1 inhibitor is pembrolizumab (KEYTRUDA®; Merck). In certain embodiments, the PD-1 inhibitor is nivolumab (OPDIVO®; Bristol-Myers Squibb). In certain other embodiments, the PD-L1 inhibitor is durvalumab (MedImmune). In another specific embodiment, the anti-CTLA4 antibody is ipilimumab (YERVOY®; Bristol-Meyers Squibb).

In specific embodiments, administration of an isolated population of T cells or a pharmaceutical composition thereof to a subject is by injection, infusion, intravenous (IV) administration, intrafemoral administration, or intratumor administration. In specific embodiments, administration of an isolated population of T cells or a pharmaceutical composition thereof to a subject is performed with a devise, a matrix, or a scaffold.

5.5.2 Treatment of Cancers Using T Cells and Other Anticancer Agents

Treatment of an individual having cancer using the antigen-specific T cells produced using the methods described herein can be part of an anticancer therapy regimen that includes one or more other anticancer agents. In addition or alternatively, treatment of an individual having cancer using the T cells produced using the methods described herein can be used to supplement an anticancer therapy that includes one or more other anticancer agents. Such anticancer agents are well-known in the art and include anti-inflammatory agents, immumodulatory agents, cytotoxic agents, cancer vaccines, chemotherapeutics, MAC inhibitors, and siRNAs. Specific anticancer agents that may be administered to an individual having cancer, e.g., an individual having tumor cells, in addition to the antigen-specific T cells produced using the methods described herein include, but are not limited to: acivicin; aclarubicin; acodazole hydrochloride; acronine; adozelesin; adriamycin; adrucil; aldesleukin; altretamine; ambomycin; ametantrone acetate; amsacrine; anastrozole; anthramycin; asparaginase (e.g., from *Erwinia chrysan*; Erwinaze); asperlin; avastin (bevacizumab); azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); Cerubidine; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; Elspar; enloplatin; enpromate; epipropidine; epirubicin hydrochloride; erbulozole; esorubicin hydrochloride; estramustine; estramustine phosphate sodium; etanidazole; etoposide; etoposide phosphate; Etopophos; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; Idamycin; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; Proleukin; Purinethol; puromycin; puromycin hydrochloride; pyrazofurin; Rheumatrex; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; Tabloid; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; Toposar; toremifene citrate; trestolone acetate; Trexall; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate;

vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-azacytidine; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptosar (also called Campto; irinotecan) camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; CC-122; CC-486; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine (e.g., Fludara); fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; anti-EGFR antibody (e.g., Erbitux (cetuximab)); anti-CD19 antibody; anti-CD20 antibody (e.g., rituximab); anti-disialoganglioside (GD2) antibody (e.g., monoclonal antibody 3F8 or ch14>18); anti-ErbB2 antibody (e.g., herceptin); human chorionic gonadotrophin; monophosphoryl lipid A+ myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); O6-benzylguanine; octreotide; okicenone; oligonucleotides; onapristone; ondansetron; ondansetron; oracin; oral cytokine inducer; ormaplatin; osaterone; oxaliplatin (e.g., Floxatin); oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; Vectibix (panitumumab)velaresol; veramine; verdins; verteporfin; vinorelbine; vinxaltine; vitaxin; vorozole; Welcovorin (leucovorin); Xeloda (capecitabine); zanoterone; zeniplatin; zilascorb; and zinostatin stimalamer.

5.5.3 Treatment of Viral Infection

In another embodiment, provided herein is a method of treating an individual having a viral infection, e.g., and active viral infection or a dormant viral infection, comprising administering to said individual a therapeutically effective amount of antigen-specific T cells produced using the methods described herein. In certain embodiments, the individual has a deficiency of T cells, e.g., a deficiency of T cells active against the individual's viral infection. In certain embodiments, the individual has too few T cells. In certain embodiments, the individual has T cells with suppressed activity. In certain other specific embodiments, said administering comprises administering an immunomodulatory compound, e.g., an immunomodulatory compound described above, or thalidomide, to said individual in addition to said antigen-specific T cells produced using the methods described herein, wherein said amount is an amount that, e.g., results in a detectable improvement of, lessening of the progression of, or elimination of, one or more symptoms of said viral infection. In specific embodiments, the viral infection is an infection by a virus of the human papillomavirus (HPV) family. In specific embodiments, the viral infection is HPV. In specific embodiments, the viral infection is a member of the herpes family. In specific embodiments, the viral infection is EBV. In specific embodiments, the viral infection is a member of the hepatitis C virus (HCV) family. In specific embodiments, the viral infection is HCV.

In other embodiments, the antigen-specific T cells produced using the methods described herein are administered to an individual having a viral infection as part of an antiviral therapy regimen that includes one or more other antiviral agents. In other embodiments, the antigen-specific T cells produced using the methods described herein are administered to an individual at risk of developing a viral infection as part of an antiviral therapy regimen that includes one or more other antiviral agents. Specific antiviral agents that may be administered to an individual having a viral infection include, but are not limited to: imiquimod, podofilox, podophyllin, interferon alpha (IFNα), reticolos, nonoxynol-9, acyclovir, famciclovir, valaciclovir, ganciclovir, cidofovir; amantadine, rimantadine; ribavirin; zanamavir and oseltaumavir; protease inhibitors such as indinavir, nelfinavir, ritonavir, or saquinavir; nucleoside reverse transcriptase inhibitors such as didanosine, lamivudine, stavudine, zalcitabine, or zidovudine; and non-nucleoside reverse transcriptase inhibitors such as nevirapine, or efavirenz.

5.5.4 Administration

In certain embodiments, T cells, e.g., antigen-specific T cells, produced using the methods described herein are used, e.g., administered to an individual, in any amount or number that results in a detectable therapeutic benefit to the individual, e.g., an effective amount, wherein the individual has a viral infection, cancer, or tumor cells, for example, an individual having tumor cells, a solid tumor or a blood cancer, e.g., a cancer patient. Such cells can be administered to such an individual by absolute numbers of cells, e.g., said individual can be administered at about, at least about, or at most about, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, or $1\times10^{11}$ T cells produced using the methods described herein. In other embodiments, antigen-specific T cells produced using the methods described herein can be administered to such an individual by relative numbers of cells, e.g., said individual can be administered at about, at least about, or at most about, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, $5\times10^{10}$, or $1\times10^{11}$ T cells produced using the methods described herein per kilogram of the individual. In other embodiments, antigen-specific T cells produced using the methods described herein can be administered to such an individual by relative numbers of cells, e.g., said individual can be administered at about, at least about, or at most about, $1\times10^5$, $5\times10^5$, $1\times10^6$, $5\times10^6$, $1\times10^7$, $5\times10^7$, $1\times10^8$, or $5\times10^8$ T cells produced using the methods described herein per kilogram of the individual.

In certain embodiments, antigen-specific T cells produced using the methods described herein are administered to a subject according to the subject's body surface area. In certain embodiments, antigen-specific T cells produced using the methods described herein are administered to a subject at a dose of $1\times10^7$ to $1\times10^{10}$ cells/m². In certain embodiments, antigen-specific T cells produced using the methods described herein are administered to a subject at a dose of $5\times10^7$, $1.5\times10^8$, $4.5\times10^8$, $1.3\times10^9$, or $2\times10^9$ cells/m². In a specific embodiment, antigen-specific T cells produced using the methods described herein are administered to a subject at a dose of $5\times10^7$ cells/m². In a specific embodiment, antigen-specific T cells produced using the methods described herein are administered to a subject at a dose of $1.5\times10^8$ cells/m². In a specific embodiment, antigen-specific T cells produced using the methods described herein are administered to a subject at a dose of $4.5\times10^8$ cells/m². In a specific embodiment, antigen-specific T cells produced using the methods described herein are administered to a subject at a dose of $1.3\times10^9$ cells/m². In a specific embodiment, antigen-specific T cells produced using the methods described herein are administered to a subject at a dose of $2\times10^9$ cells/m². In other embodiments, the antigen-specific T cells produced using the methods described herein are administered to a subject at a dose of $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, or $1\times10^{10}$ cells per kilogram.

In certain embodiments, the subject undergoes leukapheresis prior to administration of antigen-specific T cells produced using the methods described herein. In certain embodiments, the subject receives a first therapy prior to administration of antigen-specific T cells produced using the methods described herein. In specific embodiments, the first therapy is chemotherapy. In specific embodiments, the first therapy is 1, 2, 3, 4, 5, or 6 rounds of chemotherapy. In more specific embodiments, the subject receives one round of chemotherapy prior to administration of antigen-specific T cells produced using the methods described herein. In more specific embodiments, the subject receives two rounds of chemotherapy prior to administration of antigen-specific T cells produced using the methods described herein. In more specific embodiments, the subject receives three rounds of chemotherapy prior to administration of antigen-specific T cells produced using the methods described herein. In more specific embodiments, the subject receives four rounds of chemotherapy prior to administration of antigen-specific T cells produced using the methods described herein. In more specific embodiments, the subject receives five rounds of chemotherapy prior to administration of antigen-specific T cells produced using the methods described herein. In more specific embodiments, the subject receives six rounds of chemotherapy prior to administration of antigen-specific T cells produced using the methods described herein.

In certain embodiments, after leukapheresis, T cells to be administered to the subject are manufactured, tested, and released for use over the course of 28 days. In certain embodiments, the subject undergoes a lymphodepletion regiment prior to administration of antigen-specific T cells produced using the methods described herein. In certain embodiments, the lymphodepletion regimen is 1, 2, 3, 4, 5, or 6 days. In specific embodiments, the lymphodepletion regimen is 3 days. In certain embodiments, the lymphodepletion regimen is a single agent lymphodepletion regiment. In certain embodiments, the lymphodepletion regimen is a two agent lymphodepletion regiment. In certain embodiments, the single agent is cyclophosphamide. In certain embodiments, the two agents are cyclophosphamide and fludarabine. In certain embodiments, the cyclophosphamide is administered at 300 mg/m$^2$/day. In specific embodiments, the cyclophosphamide is administered at 300 mg/m$^2$/day for three days. In certain embodiments, the cyclophosphamide is administered at 900 mg/m$^2$/day. In specific embodiments, the cyclophosphamide is administered at 900 mg/m$^2$/day for three days. In certain embodiments, the cyclophosphamide is administered at 300 mg/m$^2$/day and the fludarabine is administered at 30 mg/kg/day. In specific embodiments, the cyclophosphamide is administered at 300 mg/m$^2$/day for three days and the fludarabine is administered at 30 mg/kg/day for two days. In certain embodiments, administration of antigen-specific T cells produced using the methods described herein begins 1, 2, 3, 4, or 5 days after the last day of the lymphodepletion regimen. In specific embodiments, administration of antigen-specific T cells produced using the methods described herein begins two days after the last day of the lymphodepletion regimen.

In certain embodiments, acetaminophen is administered to the subject prior to administration of antigen-specific T cells produced using the methods described herein. In certain embodiments, diphenhydramine is administered to the subject prior to administration of antigen-specific T cells produced using the methods described herein. In certain embodiments, acetaminophen and diphenhydramine are administered to the subject prior to administration of antigen-specific T cells produced using the methods described herein. In certain embodiments, acetaminophen is administered to the subject after administration of antigen-specific T cells produced using the methods described herein. In specific embodiments, acetaminophen is administered four hours after administration of antigen-specific T cells produced using the methods described herein. In certain embodiments, diphenhydramine is administered to the subject after administration of antigen-specific T cells produced using the methods described herein. In specific embodiments, diphenhydramine is administered four hours after administration of antigen-specific T cells produced using the methods described herein. In certain embodiments, acetaminophen and diphenhydramine are administered to the subject after administration of antigen-specific T cells produced using the methods described herein. In specific embodiments, acetaminophen and diphenhydramine are administered four hours after administration of antigen-specific T cells produced using the methods described herein. In certain embodiments, acetaminophen is administered to the subject prior to and after administration of antigen-specific T cells produced using the methods described herein. In certain embodiments, diphenhydramine is administered to the subject prior to and after administration of antigen-specific T cells produced using the methods described herein. In certain embodiments, acetaminophen and diphenhydramine are administered to the subject prior to and after administration of antigen-specific T cells produced using the methods described herein. In certain embodiments, acetaminophen is administered orally. In certain embodiments, diphenhydramine is administered orally. In certain embodiments, diphenhydramine is administered intravenously. In certain embodiments, diphenhydramine is administered intramuscularly. In certain embodiments, acetaminophen is administered at a dose of 300-1000 mg. In specific embodiments, acetaminophen is administered at a dose of 650 mg. In certain embodiments, diphenhydramine is administered at a dose of 10-40 mg. In specific embodiments, diphenhydramine is administered at a dose of 25 mg. In a specific embodiment, acetaminophen is administered orally at 650 mg and diphenhydramine is administered orally at 25 mg both before and after administration of antigen-specific T cells produced using the methods described herein.

The antigen-specific T cells produced using the methods described herein can be administered once to an individual having a viral infection, an individual having cancer, or an individual having tumor cells (whether detectable or undetectable), during a course of anticancer therapy; or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10, 24, 36 or more weeks during therapy. In specific embodiments, T cells produced using the methods described herein are administered once to an individual having a viral infection, an individual having cancer, or an individual having tumor cells, during a course of anticancer therapy. In specific embodiments, T cells produced using the methods described herein are administered once to an individual at risk of developing a viral infection, an individual at risk of developing cancer, or an individual at risk of developing tumor cells, during a course of anticancer therapy. In specific embodiments, T cells produced using the methods described herein are administered once to an individual to prevent recurrence of a viral infection, cancer, or tumor cells, during a course of anticancer therapy. In specific embodiments, antigen-specific T cells produced using the methods described herein can be administered once to an individual having a viral infection every 1, 2, 3, 4, 5, 6, 7, 8, 9, 10, 11, 12, 13, 14, 15, 16, 17, 18, 19, 20, 21, 22 or 23 hours. In specific embodiments, antigen-specific T cells produced using the methods described herein can be administered once to an individual having a viral infection every 1, 2, 3, 4, 5, 6 or 7 days. In specific embodiments, antigen-specific T cells produced using the methods described herein can be administered once to an individual having a viral infection every 1, 2, 3, 4, 5, 6, 7, 8, 9, 10, 24, 36 or more weeks. In specific embodiments, antigen-specific T cells produced using the methods described herein can be administered once to an individual having cancer every 1, 2, 3, 4, 5, 6, 7, 8, 9, 10, 11, 12, 13, 14, 15, 16, 17, 18, 19, 20, 21, 22 or 23 hours. In specific embodiments, antigen-specific T cells produced using the methods described herein can be administered once to an individual having cancer every 1, 2, 3, 4, 5, 6 or 7 days. In specific embodiments, antigen-specific T cells produced using the methods described herein can be administered once to an individual having cancer every 1, 2, 3, 4, 5, 6, 7, 8, 9, 10, 24, 36 or more weeks. In embodiments in which cells and an antiviral compound or anticancer compound are used, the antiviral compound or anticancer compound, and cells, can be administered to the individual together, e.g., in the same formulation; separately, e.g., in separate formulations, at approximately the same time; or can be administered separately, e.g., on different dosing schedules or at different times of the day. The antigen-specific T cells produced using the methods described herein can be administered without regard to whether T cells produced using the methods described herein have been administered to the individual in the past.

In one embodiment, the T cells are administered to the individual before a second agent. In another embodiment, a second agent is administered before the T cells. In another embodiment, the T cells and the second agent are administered simultaneously.

5.6 Kits

Provided herein is a pharmaceutical pack or kit comprising one or more containers comprising one or more of the compositions described herein, e.g., a composition comprising antigen-specific T cells produced by a method described herein. The kit may be usable standalone or may be used with automated cell production machinery in order of produce the T cells described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein, e.g., methods of treating cancer and/or methods of treating viral infection. In one embodiment, a kit comprises antigen-specific T cells produced by a method described herein or a composition thereof, in one or more containers. In a specific embodiment, provided herein is a kit comprising a T cell population produced by a method described herein, or a composition thereof. In another embodiment, provided herein is a kit comprising the components, e.g., the media or the components thereof, necessary for producing the antigen-specific T cells by the methods described herein.

In one embodiment, a kit comprises (i) T cells produced by a method described herein or a composition thereof, in one or more containers, and (ii) acetaminophen in one or more containers, and/or (iii) diphenhydramine in one or more containers. In one embodiment, a kit comprises (i) T cells produced by a method described herein or a composition thereof, in one or more containers, and (ii) cyclophosphamide in one or more containers, and/or (iii) fludarabine in one or more containers. In one embodiment, a kit comprises (i) T cells produced by a method described herein or a composition thereof, in one or more containers, and (ii) acetaminophen in one or more containers, and/or (iii) diphenhydramine in one or more containers, and (iv) cyclophosphamide in one or more containers, and/or (v) fludarabine in one or more containers.

6. EXAMPLES

Provided herein are data on varied processes described herein that can be used to establish a wide range of possible conditions described herein. Specific examples provided do not preclude the possibility of other working examples.

6.1 Example 1: APC Induction Cocktails

Combinations of APC induction cocktails were evaluated in HPV T cell generation (Table 2).

TABLE 2

Combinations of APC induction cocktails

| Condition# | Cytokine Cocktail Description |
|---|---|
| C1 | IL-4/CD40L |
| C2 | IL-4/CD40L/CpG |
| C3 | GM-CSF/IFN-α |
| C4 | GM-CSF/IL-4 + TNF-α/IL-1β/IL-6 |
| C5 | GM-CSF/IL-4/CD40L |
| C6 | GM-CSF/IL-4/CD40L/CpG |
| C7 | GM-CSF/IFN-α/IL-4/CD40L |
| C8 | GM-CSF/IFN-α/IL-4/CD40L/CpG |
| C9 | GM-CSF/IL-4/CD40L + TNF-α/IL-1β/IL-6 |
| C10 | GM-CSF/IL-4/CD40L/CpG + TNF-α/IL-1β/IL-6 |

PBMCs were cultured in G-REX®-24 from the initial seeding till the final T cell harvest. $PGE_2$ was eliminated from the process. PBMC were incubated with APC induction cytokine for 3 days prior to HPV PEPMIX™ stimulation. The other process elements in this experiment are listed in Table 3.

TABLE 3

Other parameters for the APC induction cocktail experiment.

| Parameters | Condition |
|---|---|
| PBMC | Fresh |
| Induction Cytokine | Various |
| IL-4 | 40 ng/ml |
| CD40L | 1 µg/ml |
| CpG | 4 µg/ml |
| GM-CSF | 800 U/ml |
| IFN-α-2b | 1000 U/ml |
| TNF-α | 10 ng/ml |
| IL-1β | 10 ng/ml |
| IL-6 | 10 ng/ml |
| Induction Medium | IMDM |
| Seeding density | 5 × 10e6/well |
| Reproducibility | Replicate/condition |
| Induction Duration | 3 days |
| PEPMIX™ | 1 µg/ml |
| Cytokine Feeding Delay | 48 hours |
| T cell Expansion Cytokine | |
| IL-4 | 55 ng/ml |
| IL-7 | 10 ng/ml |
| IL-15 | 1 ng/ml |
| Expansion Duration | 13 days |

The cell number was counted using ViCELL XR after harvest at day 13 post antigen loading. As shown in FIG. 1, cells expanded to a different extent under the same APC induction conditions in different donors, ranging from about 2 fold to 6 fold expansion. HPV T cell frequency and the yield are shown in FIGS. 2 and 3, respectively. HPV T cell yield takes both total cell yield and HPV T cell frequency into consideration, making it a reasonable factor for culturing condition evaluation. Accordingly, the mean HPV T cell yield is obtained by averaging the T cell yield of the replicates for the same condition.

6.2 Example 2: Expansion Cytokines

The experimental design of definition of expansion cytokines used the following concentration ranges for each cytokine: IL-4, 15 ng/ml to 55 ng/ml; IL-7, 10 ng/ml to 50 ng/ml; IL-15, 1 ng/ml to 10 ng/ml. No IL-4 (IL-7+IL-15 only) and no IL-15 (IL-4+IL-7 only) were also included. The detailed conditions are listed as Table 4. The process used 1 day APC induction with CpG, sCD40L and IL-4 as shown in Table 5. The dose of PEPMIX™ used was 1 µg/ml.

TABLE 4

Expansion cytokine combinations.

| Runs | APC induction | Seeding density | IL-15 | IL-4 | IL-7 | Expansion days |
|---|---|---|---|---|---|---|
| C1 | IL-4 10 ng/ml, | 1.75M/CM² | 1 ng/ml | 15 ng/ml | 10 ng/ml | 12 days |
| C2 | CD40L 1 μg/ml, | | 1 ng/ml | 15 ng/ml | 50 ng/ml | |
| C3 | CpG 4 μg/ml | | 1 ng/ml | 35 ng/ml | 30 ng/ml | |
| C4 | | | 1 ng/ml | 55 ng/ml | 10 ng/ml | |
| C5 | | | 1 ng/ml | 55 ng/ml | 50 ng/ml | |
| C6 | | | 5.5 ng/ml | 15 ng/ml | 10 ng/ml | |
| C7 | | | 5.5 ng/ml | 15 ng/ml | 50 ng/ml | |
| C8 | | | 5.5 ng/ml | 35 ng/ml | 30 ng/ml | |
| C9 | | | 5.5 ng/ml | 55 ng/ml | 10 ng/ml | |
| C10 | | | 5.5 ng/ml | 55 ng/ml | 50 ng/ml | |
| C11 | | | 10 ng/ml | 15 ng/ml | 10 ng/ml | |
| C12 | | | 10 ng/ml | 15 ng/ml | 50 ng/ml | |
| C13 | | | 10 ng/ml | 35 ng/ml | 30 ng/ml | |
| C14 | | | 10 ng/ml | 55 ng/ml | 10 ng/ml | |
| C15 | | | 10 ng/ml | 55 ng/ml | 50 ng/ml | |
| C16 | | | 0 | 55 ng/ml | 10 ng/ml | |
| C17 | | | 5.5 ng/ml | 0 | 30 ng/ml | |

TABLE 5

APC induction conditions for the expansion cytokine combination experiment.

| Reagent | Stock Conc. | Final Conc. | 2xcytokine cocktail | Volume/1 ml |
|---|---|---|---|---|
| IL-4 | 100 μg/ml | 20 ng/ml | 40 ng/ml | 0.4 μl |
| CD40L | 500 μg/ml | 1 μg/ml | 2 μg/ml | 4 μl |
| CpG | 4 mg/ml | 5 ug/ml | 10 μg/ml | 2.5 μl |

Total cell expansion at harvest illustrated in FIG. 4. T cells had significantly lower expansion at lower IL-15 concentration (IL-15=1 ng/ml) than those at higher concentrations (IL-15=5.5 or 10 ng/ml). There was no difference between IL-15 concentration at 5.5 ng/ml and 10 ng/ml. The condition without IL-15 had least expansion, whereas, the one without IL-4 didn't affect the T cell expansion.

T cell frequency was measured by ICCS (FIG. 5). ICCS showed a wide range of variation in T cell frequency cross all the donors in different cytokine expansion conditions. In all donors, the condition without IL-15 successfully generated T cells, but at a lower frequency than in other conditions. The condition with three cytokines in their highest concentrations (IL-4=55 ng/ml, IL-7=50 ng/ml and IL-15=10 ng/ml) had less variation in the duplicates and was on the top list for T cell frequency.

Taken both T cell expansion and T cell frequency into consideration, T cell yield was illustrated in FIG. 6. The conditions without IL-15 or with lower concentration (1 ng/ml) of IL-15 generated lower HPV T cell in all the donors. The condition with three cytokines in their highest concentrations (IL-4=55 ng/ml, IL-7=50 ng/ml and IL-15=10 ng/ml) had highest T cell yield and less variation in the duplicates.

In addition to ICCS assay, secreted cytokines were measured by 8-plex cytometrix beads array (CBA). The panel included Th1 cytokines (IL-2, IFN-γ and TNF-α), Th2 cytokines (IL-5, IL-13), Treg (IL-10) and T cell effector function related cytokines (Granzyme B and GM-CSF). The donor variations were seen in the amount and varieties regarding the secreted cytokines. The condition without IL-4 secreted relatively higher amount of IFN-γ, whereas, the one without IL-15 had the least amount of IFN-γ. The condition with three cytokines in their highest concentrations (IL-4=55 ng/ml, IL-7=50 ng/ml and IL-15=10 ng/ml) was one of the conditions that had higher Th1 cytokines and lower Th2 or Treg cytokines.

T cell differentiation markers were also measured in 2 of the 4 donors by antibody staining and flow cytometer analysis. The Tcm, Tem and Teff percentage within CD45R0 positive T cell population were determined as shown in FIG. 7. CD45RO+CD62Lhi T cell population was also determined (FIG. 8), since it was reported to have positive correlation with clinical efficacy in adoptive T cell therapy. After 12 day expansion, majority of the T cells were effect T cells in one of the donors. It was difficult to see any difference in their differentiation markers under different cytokine conditions since more than 80% of the T cells were effectors. In the other donor, it clearly showed that higher IL-15 concentration have driven more T cell differentiation. The condition without IL-15 had higher Tcm and less Teff. However, there was no significant difference in the CD45RO+CD62Lhi populations.

6.3 Example 3: APC Induction Duration

Frozen PBMC are thawed three days in a row and treated with APC induction cocktail as shown in Table 6 for simultaneous HPV PEPMIX™ stimulation post different APC induction durations. PBMC are stimulated with APC induction cocktail for 3 days in the presence or absence of 2 ng/ml IL-7. The APC induction conditions are shown in Table 6, and general experiment conditions are listed in Table 7.

TABLE 6

APC induction conditions.

| CONDITION# | APC Induction Cocktail | Duration | IL-7 | Day −3 | Day −2 | Day −1 |
|---|---|---|---|---|---|---|
| 1 | IL-4/CD40L | 3 days | − | IL-4/CD40L | | |
| 2 | IL-4/CD40L/CpG | 3 days | − | IL-4/CD40L/CpG | | |
| 3 | GM-CSF/IFN-α | 3 days | − | GM-CSF/IFN-α | | |
| 4 | GM-CSF/IFN-α/ IL-4/CD40L/CpG | 3 days | − | GM-CSF/IFN-α/ IL-4/CD40L/CpG | | |
| 5 | IL-4/CD40L | 3 days | + | IL-4/CD40L + IL-7 | | |
| 6 | IL-4/CD40L/CpG | 3 days | + | IL-4/CD40L/ CpG + IL-7 | | |
| 7 | GM-CSF/IFN-α | 3 days | + | GM-CSF/IFN-α + IL-7 | | |
| 8 | GM-CSF/IFN-α/ IL-4/CD40L/CpG | 3 days | + | GM-CSF/IFN-α/ IL-4/CD40L/ CpG + IL-7 | | |
| 9 | GM-CSF/IFN-α + IL-4/CD40L + CpG | 3 days | − | GM-CSF/IFN-α | IL-4/CD40L | CpG |
| 10 | GM-CSF/IFN-α + IL-4/CD40L + CpG | 3 days | + | GM-CSF/IFN-α/ IL-7 | IL-4/CD40L | CpG |
| 11 | IL-4/CD40L | 2 days | − | | IL-4/CD40L | |
| 12 | IL-4/CD40L/CpG | 2 days | − | | IL-4/CD40L/CpG | |
| 13 | GM-CSF/IFN-α | 2 days | − | | GM-CSF/IFN-α | |
| 14 | GM-CSF/IFN-α/ IL-4/CD40L/CpG | 2 days | − | | GM-CSF/IFN-α/ IL-4/CD40L/CpG | |
| 15 | IL-4/CD40L | 1 day | − | | | IL-4/CD40L |
| 16 | IL-4/CD40L/CpG | 1 day | − | | | IL-4/CD40L/CpG |
| 17 | GM-CSF/IFN-α | 1 day | − | | | GM-CSF/IFN-α |
| 18 | GM-CSF/IFN-α/ IL-4/CD40L/CpG | 1 day | − | | | GM-CSF/IFN-α/ IL-4/CD40L/CpG |

TABLE 7

Other experimental parameters for the APC induction duration experiment.

| Parameters | Condition |
|---|---|
| Donor# | 4 |
| PBMC | Frozen |
| Induction Cytokine | Various |
| IL-4 | 20 ng/ml |
| CD40L | 1 μg/ml |
| CpG | 4 ug/ml |
| GM-CSF | 800 U/ml |
| IFN-α-2b | 1000 U/ml |
| IL-7 | 2 ng/ml |
| Induction Medium | T cell media |
| Seeding density | 5 × 10e6/well |
| Reproducibility | Replicate/condition |
| Induction Duration | 1/2/3 days |
| PEPMIX ™ | 1 μg/ml |
| Cytokine Feeding Delay | 48 hours |
| Expansion Cytokine | |
| IL-4 | 55 ng/ml |
| IL-7 | 50 ng/ml |
| IL-15 | 9 ng/ml |
| Expansion Duration | 12 days |

The cell number was counted using ViCELL XR after harvest at day 12 post antigen loading. As shown in FIG. 9, IL-4 and CD40L-treated cells generate highest yield after HPV PEPMIX™ stimulation, whereas GM-CSF and IFN-α-induced conditions show lowest cell expansion, regardless the duration of the APC induction. There was no significant difference in cell expansion capacity between different APC induction durations for a given induction cocktail, except that cell yield of donor #4 after 1-day induction is remarkably lower than that after 2- or 3-day induction (FIG. 9). Sequential addition of components in cocktail IL-4/CD40L/CpG/GMCSF/IFN-α appears to compromise cell expansion compared to concurrent addition. The presence of IL-7 during APC induction minimally improves cell yield, if at all.

HPV T cells were identified using ICCS. Opposite to the trend of cell expansion, T cells generated from GM-CSF and IFN-α-induced PBMC showed the highest HPV T cell frequency compared with cells from other APC induction cocktail treatment for a given APC induction duration (FIG. 10). Sequential addition of cocktail component of IL-4/CD40L/CpG/GMCSF/IFN-α improves HPV T cell frequency more or less in the presence or absence of IL-7.

HPV T cell yield is shown in FIG. 11. The pattern of T cell yield of different conditions is similar to that of T cell frequency as shown in FIG. 10, although the differences are generally to a less extent.

6.4 Example 4: Growth Curve Definition

The experiment was designed to address the following goals by using PBMC from 11 healthy donors: define the growth curve of current T cell process, define the duration of T cell signals, define T cell purity in T cell harvests on different days, explore dynamics of T cell differentiation markers, and generate product materials for microarray analysis and composition IP in multiple donors.

To determine the growth curve and cell doubling time, the mean of total cell number from 11 donors±SD was plotted as shown in FIG. 12. The Y axis represents the total cell number and X axis represented days post antigen loading.

Cell doubling time was calculated by using online software (http://www.doubling-time.com/compute.php?lang=en).

Figure 13:
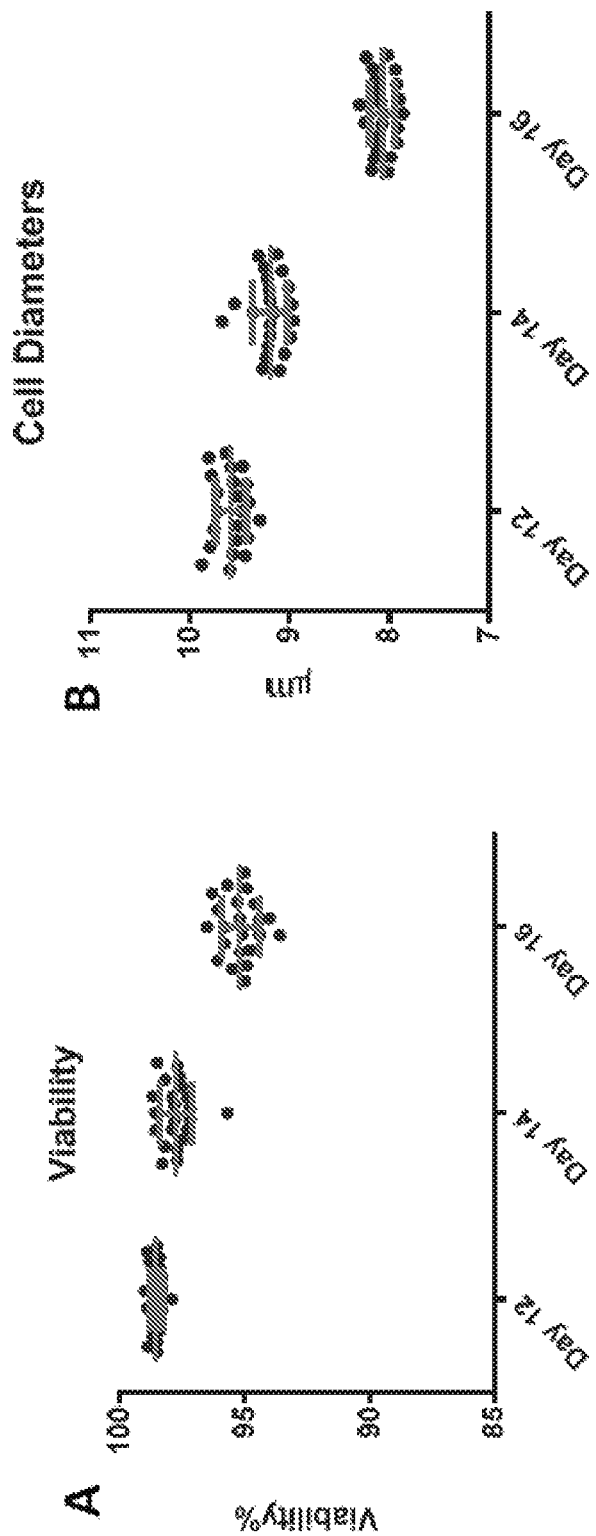

Cell viability and cell size were measured by ViCell, and the results as shown in FIG. 13. Cell viability started to drop after day 12 and it was much lower on day 16. The cell size also decreased with culture extension. The average diameter of the cells on day 12 were about 9 to 10 μm, it dropped to 8 μm by day 16.

Figure 14:
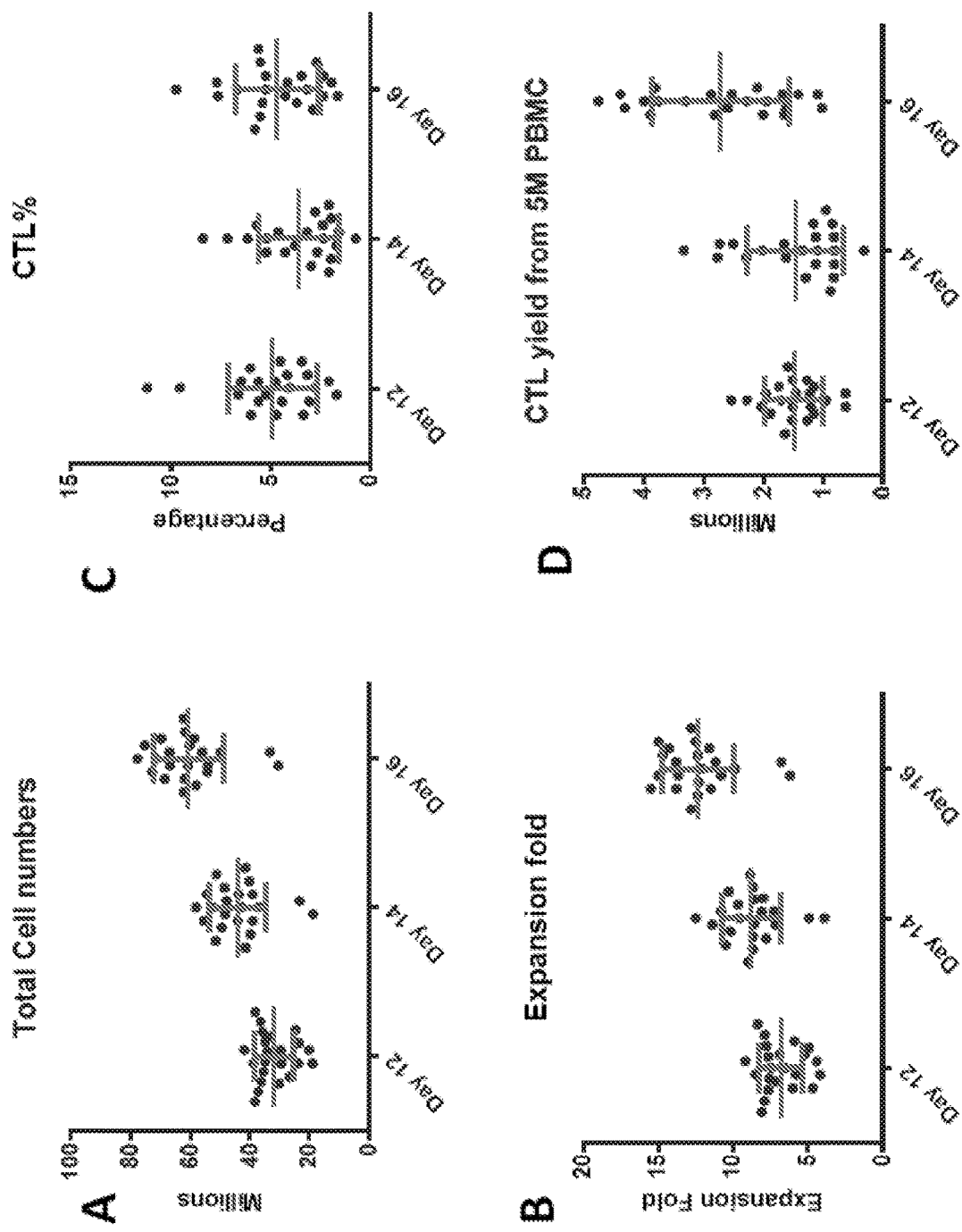

The cell number, expansion fold, T cell frequency and T cell yield were shown in FIG. 14. Total cell number or fold expansion increased with culture extension from 12 days to 16 days. The average fold change was about 7 on day 12 and it reached more than 10 fold on day 16. There were no significant changes about T cell frequency between day 12 and day 16. The total T cell yield was higher on day 16 than day 12 or day 14 since it had greater cell expansion.

T cell purity was defined by antibody staining and flow cytometry analysis, using T cell purity panel of CD19, CD56, CD3, CD11c, CD4, and CD8. The results demonstrated that T cell purity was greater than 85% from all the donors by day 12 and it slightly increased with culture extension. The small percentage of non-T cells are mainly NK and NKT cells. B cells were less than 1% from all the donors. Majority of the T cells generated from this process were CD4 T cells, it accounted about 80%. The CD4/CD8 T cell ratio decreased with culture extension. See FIG. 15 and FIG. 16.

The T cell differentiation status was also checked by antibody staining and flow cytometry analysis using T cell differentiation panel of CD3, CD62L, CD4, CD27, CCR7, and CD45RO. From day 12 to day 16, CD45RO+ memory T cell population increased. There was no significant difference in CD45RO+CD62Lhi population between day 12, day 14 and day 16 (FIG. 17). Within the CD45RO+ population, percentage of central memory T cell percentage decreased, while effect T cell population increased (FIG. 18).

HPV antigen specific T cells were generated from all 11 donors. The growth curve was determined; the log phase was between 8 to 13 days. The T cell purity increases with culture extension. 10/11 donors purity were more than 85% by day 12. They were more than 90% for all the donors after day 14. The non-T cell populations were mainly NK and NK T cells, less than 1% of B cells. There was significant increase in T cell expansion and T cell yield from day 12 to day 16, however accompanied with the decrease of cell viability and cell size, as well as a more differentiated phenotype.

6.5 Example 5: Seeding Density and Cytokine Cocktail Concentrations

The purpose of this experiment was to determine the optimal PBMC seeding density and working concentrations of APC induction cytokine cocktail for HPV T cell priming and proliferation. Fresh PBMC are seeded at different density in the wells of G-REX®-24 as shown in Table 8.

TABLE 8

PBMC seeding density conditions.

| CONDITION# | DENSITY (CELL#/WELL) | IL-4 (ng/ml) | CD40L (μg/ml) |
|---|---|---|---|
| 1 | 2.50E+06 | 10 | 0.25 |
| 2 | 2.50E+06 | 10 | 1 |
| 3 | 2.50E+06 | 10 | 4 |
| 4 | 2.50E+06 | 40 | 0.25 |
| 5 | 2.50E+06 | 40 | 1 |
| 6 | 2.50E+06 | 40 | 4 |
| 7 | 5.00E+06 | 10 | 0.25 |
| 8 | 5.00E+06 | 10 | 1 |
| 9 | 5.00E+06 | 10 | 4 |
| 10 | 5.00E+06 | 40 | 0.25 |
| 11 | 5.00E+06 | 40 | 1 |
| 12 | 5.00E+06 | 40 | 4 |
| 13 | 1.00E+07 | 10 | 0.25 |
| 14 | 1.00E+07 | 10 | 1 |
| 15 | 1.00E+07 | 10 | 4 |
| 16 | 1.00E+07 | 40 | 0.25 |
| 17 | 1.00E+07 | 40 | 1 |
| 18 | 1.00E+07 | 40 | 4 |

Since the area of the bottom surface of a G-REX®-24 well is 2 cm$^2$, the seeding density of 1×10$^7$/well, 5×10$^6$/well, and 2.5×10$^6$/well equals to 5×10$^6$/cm$^2$, 2.5×10$^6$/cm$^2$, and 1.25×10$^6$/cm$^2$, respectively. The cells are treated with APC induction cocktail IL-4 and CD40L at various concentrations for 24 hour prior to HPV PEPMIX™ stimulation. The general experiment conditions are listed in Table 9.

TABLE 9

Other parameters for PBMC seeding density experiment.

| Parameters | Condition |
|---|---|
| Donor# | 3 |
| PBMC | Fresh |
| Induction Cytokine | |
| IL-4 | 10 and 40 ng/ml |
| CD40L | 0.25, 1, and 4 μg/ml |
| Induction Medium | T cell media |
| Seeding density | 2.5, 5, 10 × 10e6/well |
| Reproducibility | Replicate/condition |
| Induction Duration | 1 day |
| PEPMIX ™ | 1 μg/ml |
| Cytokine Feeding Delay | 48 hours |
| T cell Expansion Cytokine | |
| IL-4 | 55 ng/ml |
| IL-7 | 50 ng/ml |
| IL-15 | 9 ng/ml |
| T cell Expansion Duration | 14 days |

All three donors show the same trend that total cell yield is positively proportional to the seeding density, whereas the expansion fold is inversely proportional to the seeding density. No significant impact of different IL-4 and CD40L concentrations on expansion fold change is observed.

HPV T cell frequency is also analyzed (FIG. 19). Generally, highest HPV T cell frequency is generated from the condition where the PBMC are seeded at highest density (1×10$^7$/well). The HPV T cell frequency is positively proportional to the seeding density. There is no clear pattern regarding the influence of different concentration of IL-4 or CD40L on the HPV T cell frequency across all three donors.

HPV T cell yield is shown in FIG. 20. The pattern of HPV T cell yield is comparable to HPV T cell frequency. The impact from different seeding density is more pronounced in T cell yield than T cell frequency, attributed to the added effect from both cell yield and T cell frequency. All conditions with seeding density at 1×10$^7$/well are superior to other conditions with lower seeding densities in all donors except for one condition from donor #1. Statistical analysis conducted between 6 APC induction conditions with the seeding density at 1×10⁷/well shows no significant difference (P>0.05).

The results presented herein show that the seeding density at 5×10⁶/cm² (1×10⁷/well) generates highest HPV T cell yield, and the working concentration of IL-4 and sCD40L is 10-40 ng/ml and 0.25-4 µg/ml, respectively.

6.6 Example 6: Process Characterization

Certain process elements were investigated herein. IMDM and T cell media are used during APC induction for comparison. HPV PEPMIX™ has been used at 1 µg/ml for each of the 4 HPV PEPMIX™ types in previous definition experiments. In this experiment, HPV PEPMIX™ are dosed at 0.5, 1, and 2 µg/ml for optimal dose determination. Timing for initial T cell expansion cytokine supplementation is also defined by delaying the IL-4/IL-7/IL-15 addition until 2 hours, 24 hours, and 48 hours post HPV PEPMIX™ loading. IL-4 presence throughout the T cell expansion, or discontinued after initial feeding is also evaluated when T cell expansion cytokine is added after 48-hour delay. The experiment design is summarized in Table 10. The general experiment conditions are shown in Table 11.

TABLE 10

Experimental conditions for overall process.

| CONDITION# | APC Induction Medium | PEPMIX ™ Dose | Cytokine Addition Delay | IL-4 Feeding |
|---|---|---|---|---|
| C1 | IMDM | 1 µg/ml | 2 hours | All |
| C2 | IMDM | 1 µg/ml | 24 hours | All |
| C3 | IMDM | 1 µg/ml | 48 hours | All |
| C4 | IMDM | 1 µg/ml | 48 hours | 1st feeding |
| C5 | T cell | 1 µg/ml | 2 hours | All |
| C6 | T cell | 1 µg/ml | 24 hours | All |
| C7 | T cell | 1 µg/ml | 48 hours | All |
| C8 | T cell | 1 µg/ml | 48 hours | 1st feeding |
| C9 | T cell | 0.5 µg/ml | 48 hours | All |
| C10 | T cell | 2 µg/ml | 48 hours | All |

TABLE 11

Other parameters for overall process experiment.

| Parameters | Condition |
|---|---|
| Donor# | 3 |
| PBMC | Fresh |
| Induction Cytokine | |
| IL-4 | 10 ng/ml |
| CD40L | 1 µg/ml |
| Induction Medium | IMDM/T cell media |
| Seeding density | 1 × 10e7/well |
| Reproducibility | Replicate/condition |
| APC Induction Duration | 1 day |
| PEPMIX ™ | 0.5, 1, and 2 µg/ml |
| 1st Cytokine Feeding Delay | 2, 24, and 48 hours |
| T cell Expansion Cytokine | |
| IL-4 | 55 ng/ml |
| IL-7 | 50 ng/ml |
| IL-15 | 9 ng/ml |
| T cell Expansion Duration | 12 days |

For the APC induction cocktail, IL-4 and CD40L are used at 10 ng/ml and 1 µs/ml, respectively. Furthermore, PBMC are seeded at 1×10⁷/well. HPV T cells are expanded for 12 days.

In addition to ICCS, cytokine profile is also measured in the T cells upon antigen re-stimulation using cytometric beads array. The measured cytokines are listed in Table 12.

TABLE 12

Cytokines measured in the cytokine profile upon antigen-stimulation.

| Type | Cytokines |
|---|---|
| Th1 | IL-2, TNF-α, IFN-γ |
| Th2 | IL-5, IL-13 |
| Pro-inflammatory | GM-CSF |
| Immune regulatory | IL-10 |
| Cytotoxic | Granzyme B |

Transcription factor for Th1 (T-bet), Th2 (GATA-3), and Treg (FoxP3) are also analyzed in harvested T cell after the completion of process.

T cell are harvested at day 12 post HPV PEPMIX™ stimulation. The viable cells are counted using ViCell as described in experiment procedure. The results of cell expansion fold are shown in FIG. 21.

The results show that higher cell expansion fold is obtained under the condition where T cell media is used as APC induction media across all donors. In addition, cell expansion fold is inversely proportional to the cytokine delay length. Furthermore, IL-4 discontinuation slightly improves cell expansion. In donor #1 and #2, the HPV PEPMIX™ dosed at 0.5 and 1 µg/ml does not show evident effect on cell expansion capacity, whereas 2 µg/ml HPV PEPMIX™ appears to compromise cell yield. The first feeding of T cell expansion cytokine and media to the cells receiving 0.5 and 2 µg/ml PEPMIX™, is skipped in donor #3, therefore the comparison with 1 mg/ml is not conducted in the whole experiment for this donor.

The HPV T cell frequency is analyzed and shown in FIG. 22. Higher HPV T cell frequency is obtained under many conditions where IMDM media is used as APC induction media across all donors, especially in the case where the HPV T cell frequency is generally low for a given donor, such as Donor #2. In addition, HPV T cell frequency is positively proportional to the cytokine delay length at donor #1. For donor #2 and #3, the differences of HPV T cell frequency between different cytokine delays are not evident except that 24-hr and 48-hr delay generates slightly higher HPV T cell than 2-hr delay in donor #3. IL-4 discontinuation slightly improves HPV T cell frequency where IMDM is used for APC induction, but this improvement is not exhibited under the condition where T cell media is used for APC induction. HPV PEPMIX™ at 2 µg/ml stimulates highest HPV T cell frequency in donor #1 and #2. Stimulation with HPV PEPMIX™ at 0.5 µg/ml generates lowest HPV T cell frequency among all tested conditions in donor #1.

HPV T cell yield is shown in FIG. 23. The T cell yield shows a similar pattern to HPV T cell frequency. Slightly higher HPV T cell yield is obtained under many conditions where IMDM media is used as APC induction media across all donors, especially in the case where the HPV T cell frequency is generally low for a given donor, such as Donor #2. In addition, HPV T cell yield is positively proportional to the cytokine delay length at donor #1. For donor #2 and #3, the differences of HPV T cell frequency between different cytokine delays are not evident except that 24-hr and 48-hr delay generates slightly higher HPV T cell than 2-hr delay in donor #3. IL-4 discontinuation slightly improves HPV T cell yield where IMDM is used for APC induction, but this improvement is not exhibited under the condition where T cell media is used for APC induction. HPV PEP-MIX™ at 2 μg/ml stimulates slightly higher HPV T cell yield than 1 μg/ml counterpart in donor #1 and #2. Stimulation with HPV PEPMIX™ at 0.5 μg/ml generates lowest HPV T cell frequency among all tested conditions in donor #1.

Several conditions in this experiment are specifically designed to assess Th1 cytokine IFN-γ production by primed HPV T cell; therefore, in addition to total HPV T cell analysis, we also performed IFN-γ-producing HPV T cell analysis. The results of IFN-γ-producing HPV T cell frequency is shown in FIG. 24. Different than the trend in total HPV T cell frequency in FIG. 22, most of cells cultured with IMDM for APC induction generate higher IFN-γ-producing T cell frequency than their counterpart culture with T cell media during APC induction. IFN-γ-producing T cell is almost undetectable in cells from donor #2. Within IMDM induction conditions, 24-hr cytokine addition delay shows comparable influence on IFN-γ-producing cell frequency to 48-hr cytokine addition delay, if not any higher. IL-4 withdrawal during T cell expansion in IMDM induction conditions slightly improves IFN-γ-producing HPV T cell frequency in all tested donors.

Cytokines secreted by HPV T cell upon antigen re-stimulation are also measured. To discover which T helper cell subset, Th1 or Th2 helper cells, is dominant in HPV T cell product under different culturing conditions, Th1/Th2 ratio is acquired by dividing representative Th1 cytokine IFN-γ level with representative Th2 cytokine IL-5 level (FIG. 25). The higher the ratio of Th1/Th2, the more dominant Th1 response in the microenvironment. Generally, cells cultured with IMDM for APC induction show higher Th1/Th2 than those cultured with T cell media. Cells with expansion cytokine addition delayed till 24 hours later show higher Th1/Th2 ratio than those with 48-hr delay.

To further assess the effect of APC induction media and the IL-4 continuous present during T cell expansion on T cell subset differentiation, transcription factors for Th1 (T-bet), Th2 (GATA-3), and Treg (FoxP3) are examined in conditions where T cell expansion cytokine cocktail are not provided until 48 hours post HPV PEPMIX™ stimulation (FIG. 26). Cells cultured with T cell media during APC induction show slightly higher frequency of CD4+T-bet+ Th1 cells than those cultured with IMDM. There is no clear pattern as to the impact of APC induction media on frequency of CD4+GATA-3+Th2 cells, therefore the pattern of Th1/Th2 ratio is also compatible with the Th1 frequency. In addition, slightly higher percentage of Treg is obtained in cultured with IMDM as the APC induction media. The effect of IL-4 withdrawal during T cell expansion shows clear improvement of Th1 frequency and reduction of Th2 frequency, resulting in the elevated Th1/Th2 ratio compared with the counterpart condition where IL-4 is present throughout the T cell expansion phase. This suggests that IL-4 removal skews T cell response toward Th1.

6.7 Example 7: Example T Cell Production Protocols

This Example describes several protocols for producing antigen-specific T cells.

Protocol 1: A leukapheresis unit is obtained from an individual. PBMCs are isolated from the unit and frozen in a formulation comprising 40% v/v HSA and 5% DMSO in Plasma-Lyte™. On Day 0, the PBMCs are thawed, and cultured and APC induction is initiated in 6-well plates in IMDM medium comprising IL-4 (10 ng/mL) and CD40L (1 μg/mL). On Day 1, T cells within the PBMCs are activated using T cell medium comprising a PepMix derived from at least one viral or tumor antigen at 1 μg/mL. On Day 2, the T cells are expanded in T cell medium comprising 55 ng/mL IL-4, 50 ng/mL IL-7, and 9 ng/mL IL-15. On Days 5, 8, and 11, the medium is replaced with T cell medium comprising 50 ng/mL IL-7 and 9 ng/mL IL-15. On Day 13, the T cells are collected, concentrated in a centrifuge and washed at least once in Plasma-Lyte™ comprising 10% v/v HSA. The cells are then resuspended in Plasma-Lyte™ comprising 10% v/v HSA and 6% w/v Dextran-40, and diluted to a final cell concentration of 1-20×10$^6$ cells/mL in a solution comprising RPMI medium (32% v/v), 12.5% w/v HSA, and 5% v/v DMSO. The cells are then frozen for shipping to the point of delivery.

Protocol 2: A leukapheresis unit is obtained from an individual. PBMCs are isolated from the unit and frozen in a formulation comprising 40% v/v HSA and 5% w/v DMSO in Plasma-Lyte™. On Day 0, the PBMCs are thawed, and cultured and APC induction is initiated in a G-REX 100 mL culture flask in IMDM medium comprising IL-4 (10 ng/mL) and CD40L (1 μg/mL). On Day 1, T cells within the PBMCs are activated using T cell medium comprising a PepMix derived from at least one viral or tumor antigen at 1 μg/mL. On Day 2, the medium is removed and the T cells are expanded in replacement T cell medium comprising 55 ng/mL IL-4, 50 ng/mL IL-7, and 9 ng/mL IL-15. On Day 5, the medium is replaced with T cell medium comprising 50 ng/mL IL-7 and 9 ng/mL IL-15, and the cells are cultured for an additional seven days. On Day 13, the T cells are collected, concentrated in a centrifuge and washed at least once in Plasma-Lyte™ comprising 10% v/v HSA. The cells are then resuspended in Plasma-Lyte™ comprising 10% v/v HSA and 6% w/v Dextran-40, and diluted to an intermediate cell concentration of 8-35×10$^6$ cells/mL in the same solution. After passage of the cells through a 60 μm in-line strainer, the cells are brought to a final cell concentration of 1-20×10$^6$ cells/mL in a solution comprising Plasma-Lyte™ (32% v/v), 0.17% w/v NaCl, 5.5% w/v Dextran-40, 10% w/v HSA, and 5% v/v DMSO. The cells are then frozen for shipping to the point of delivery.

Protocol 3: A leukapheresis unit is obtained from an individual. PBMCs are isolated from the unit and washed and frozen in a formulation comprising 40% v/v HSA and 5% w/v DMSO in Plasma-Lyte™. On Day 0, the PBMCs are thawed, and cultured and APC induction is initiated in a WAVE 100 mL bioreactor in IMDM medium comprising IL-4 (10 ng/mL) and CD40L (1 μg/mL). On Day 1, T cells within the PBMCs are activated using T cell medium comprising a PepMix derived from at least one viral or tumor antigen at 1 μg/mL. On Day 2, the medium is removed and the T cells are expanded in replacement T cell medium comprising 55 ng/mL IL-4, 50 ng/mL IL-7, and 9 ng/mL IL-15. On Day 5, the medium is replaced with T cell medium comprising 50 ng/mL IL-7 and 9 ng/mL IL-15, and the cells are cultured for an additional seven days. On Day 13, the T cells are collected, concentrated in a washed at least once in Plasma-Lyte™ comprising 10% v/v HSA using a Lovo Cell Processing System (Fresenius Kabi). The cells are then resuspended in Plasma-Lyte™ comprising 10% v/v HSA and 6% w/v Dextran-40, and diluted to an intermediate cell concentration of 8-35×10$^6$ cells/mL in the same solution. After passage of the cells through a 60 μm in-line strainer, the cells are brought to a final cell concentration of 1-20×10$^6$ cells/mL in a solution comprising Plasma-Lyte™ (32% v/v), 0.17% w/v NaCl, 5.5% w/v Dextran-40, 10% w/v HSA, and 5% v/v DMSO. The cells are then frozen for shipping to the point of delivery.

Protocol 4: A leukapheresis unit is obtained from an individual. PBMCs are isolated from the unit and washed, using a Cell Saver 5 Centrifuge and frozen in a formulation comprising 10% w/v HSA and 5% v/v DMSO in Plasma-Lyte™ (32% v/v). On Day 0, the PBMCs are thawed, and cultured and APC induction is initiated in a Grex 100 mL culture device in IMDM medium comprising IL-4 (10 ng/mL) and CD40L (1 μg/mL). On Day 1, T cells within the PBMCs are activated in the Grex device using T cell medium comprising a PepMix derived from at least one viral or tumor antigen at 1 μg/mL, e.g., HPV16 and HPV18 E6 and E8 protein PepMixes at 1 μg/mL each. On Day 2, T cells are expanded in replacement T cell medium (added to existing medium) comprising 55 ng/mL IL-4, 50 ng/mL IL-7, and 9 ng/mL IL-15. On Days 5, 8, and 11, the medium is supplemented in the same Grex device with T cell medium comprising 50 ng/mL IL-7 and 9 ng/mL IL-15. On Day 13, the T cells are collected, and washed at least once in Plasma-Lyte™ comprising 10% v/v HSA using a Lovo Cell Processing System (Fresenius Kabi). The cells are then resuspended in Plasma-Lyte™ comprising 10% w/v HSA and 6% w/v Dextran-40, and diluted to an intermediate cell concentration of 8-35×10$^6$ cells/mL in the same solution. The resulting cell suspension is then filtered through a 60 μm in-line strainer, and diluted to ~20×10$^6$ cells/mL in a solution comprising Plasma-Lyte™ 32% v/v, Dextran-40 5.5% w/v, HAS 10% w/v, NaCl 0.17% w/v, and DMSO 5% v/v. The cell suspension is then transferred to cell a storage bag and frozen for later use. For the foregoing steps, the Grex device may be substituted with a WAVE™ Bioreactor, static bag, or the like.

6.8 Example 8: Functional Characterization of T Cells

T cells generated as in Example 7 were tested for their functional properties.

HPV16/18 in Normal and Cancer Patients.

T cells were generated as described in Example 7 from five cervical cancer patients, one healthy donor positive for HPV 16 and HPV 18, and three healthy donors of unknown HPV status. The T cells were than activated with HPV 16 or HPV 18 E6 or E7 antigenic peptides, or E6 and E7 antigenic peptides from both HPV 16 and HPV 18 (FIG. 27). The T cells from the cervical cancer patients responded to both HPV 16 and HPV 18 antigens, but particularly HPV 16 antigens. The T cells from healthy donors responded to both HPV 16 and HPV 18 antigens, but particularly HPV 16 antigens.

In Vitro Tumor Killing.

Figure 28:
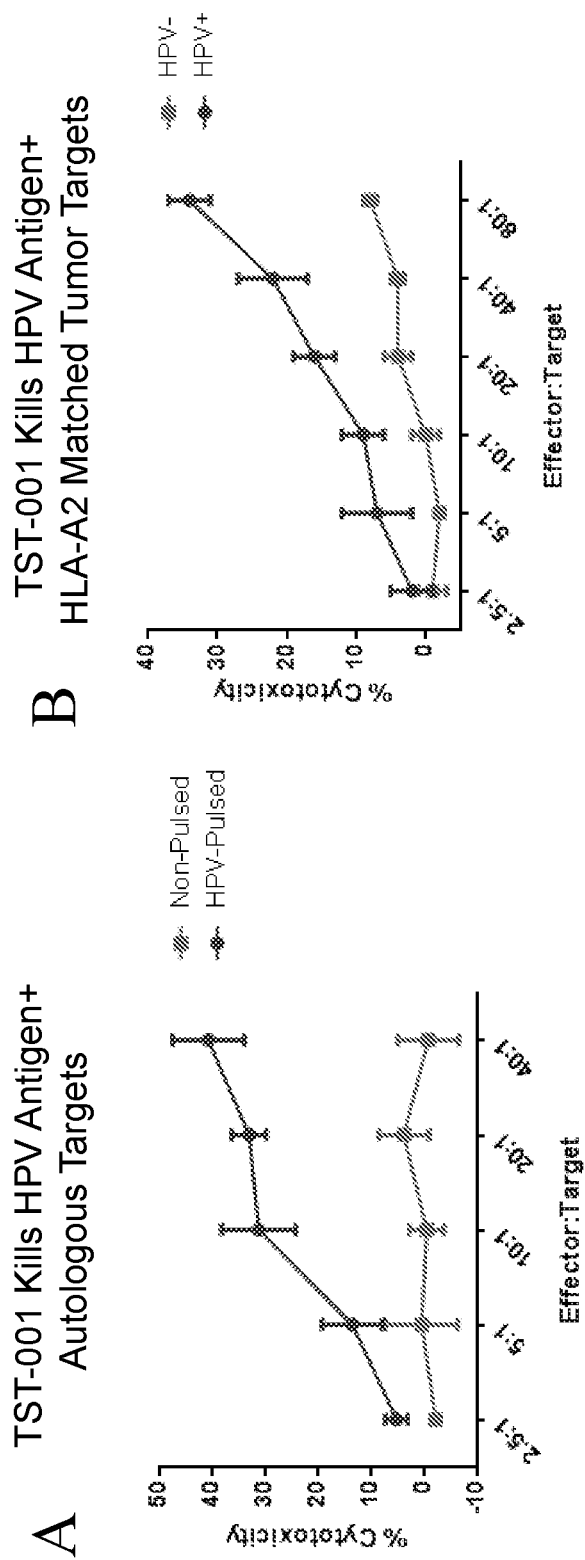

T cells generated as described in Example 7 and then tested against autologous targets or HLA-A2 matched targets in vitro at effector to target ratios of 2.5:1, 5:1, 10:1, 20:1, and 40:1 (FIG. 28). When autologous or HLA-A2 matched targets were pulsed with HPV, T cells killed autologous targets (FIG. 28A) and HLA-A2 matched targets (FIG. 28B). However, when the target cells were not pulsed with HPV, little to no killing was observed.

HPV Antigen Specificity and Effector Activity.

Cells from seven donors were tested before (PBMCs) and after (T cells) generation of T cells via the protocols described in Example 7. The HPV antigen specificity was tested by measuring surface expression of CD137 (FIG. 29A). Effector activity was measured in HPV-stimulated PBMCs and in HPV or non-HPV stimulated T cells by measuring secretion of IFN-γ (FIG. 29B), GM-CSF (FIG. 29C), and TNF-α (FIG. 29D). Only the T cells, and not the PBMCs from which they were derived, secreted pro-inflammatory Th1 cytokines.

6.9 Example 9: Gene Expression by T Cells

This Example details gene expression differences between PBMCs obtained from patients and the HPV-specific T cells produced by the method of Example 7, above, using a PepMix comprising HPV16 and HPV18 E6 and E7 protein-derived peptides.

RNA was isolated from patient PBMCs and from T cells made from PBMCs from the same patient. The data was generated from gene expression array analysis using an Affymetrix U133A Plus 2.0 GeneChip® Array. Briefly, gene expression profiles of 20 lines of T cells (10 from HPV T cell and 10 from their matched PBMC) were generated. The fold changes of gene expression were obtained by normalization with housekeeping genes (beta-2-microglobulin (B2M), hypoxanthine phosphoribosylotransferase (HPRT), and Large Ribosomal Protein (RPLPO)) followed by comparison of expression levels between samples. Pairwise comparison of gene expression between T cells from HPV T cell and that from matched PBMC were performed. Genes that were differentially expressed between the two groups were identified by statistical analysis. Within these identified genes, those that demonstrated more than 5 fold (used as a cut-off to eliminate some genes to meet the software limit for analysis) difference were input into IPA (Ingenuity Pathway Analysis-Biostatistic), which classifies the genes into different pathways based on their knowledge database.

Genes overexpressed in the T cells vs. PBMCs are listed in Table 13 below, and are identified by standard gene symbol, Entrez gene name, Affymetrix ID number, and Entrez gene ID. The "Exp Fold Change" column identifies the fold-change in expression of the indicated gene in T cells over PBMCs. Additionally, the genes are grouped according to the particular pathway of which the genes are a part.

TABLE 13

| Symbol | Entrez Gene Name | Affymetrix | Exp Fold Change | Location | Type(s) | Entrez Gene ID for Human |
|---|---|---|---|---|---|---|
| Genes overexpressed in the T cells vs. PBMCs | | | | | | |
| CELL CYCLE CONTROL | | | | | | |
| CDC6 | cell division cycle 6 | 203967_at | 12.37 | Nucleus | other | 990 |
| CDC45 | cell division cycle 45 | 204126_s_at | 66.74 | Nucleus | other | 8318 |

TABLE 13-continued

Genes overexpressed in the T cells vs. PBMCs

| Symbol | Entrez Gene Name | Affymetrix | Exp Fold Change | Location | Type(s) | Entrez Gene ID for Human |
|---|---|---|---|---|---|---|
| CDK2 | cyclin dependent kinase 2 | 211804_s_at | 6.86 | Nucleus | kinase | 1017 |
| CDK4 | cyclin dependent kinase 4 | 202246_s_at | 5.09 | Nucleus | kinase | 1019 |
| CDK5 | cyclin dependent kinase 5 | 204247_s_at | 46.05 | Nucleus | kinase | 1020 |
| CDK6 | cyclin dependent kinase 6 | 235287_at | 11.25 | Nucleus | kinase | 1021 |
| CDT1 | chromatin licensing and DNA replication factor 1 | 209832_s_at | 21.78 | Nucleus | other | 81620 |
| CHEK2 | checkpoint kinase 2 | 210416_s_at | 14.75 | Nucleus | kinase | 11200 |
| MCM2 | minichromosome maintenance complex component 2 | 202107_s_at | 7.11 | Nucleus | enzyme | 4171 |
| MCM3 | minichromosome maintenance complex component 3 | 201555_at | 5.64 | Nucleus | enzyme | 4172 |
| MCM4 | minichromosome maintenance complex component 4 | 222037_at | 22.71 | Nucleus | enzyme | 4173 |
| MCM5 | minichromosome maintenance complex component 5 | 201755_at | 6.12 | Nucleus | enzyme | 4174 |
| PCNA | proliferating cell nuclear antigen | 201202_at | 5.56 | Nucleus | enzyme | 5111 |
| POLA1 | DNA polymerase alpha 1, catalytic subunit | 204835_at | 10.84 | Nucleus | enzyme | 5422 |
| PRIM1 | primase (DNA) subunit 1 | 205053_at | 8.49 | Nucleus | enzyme | 5557 |
| TOP2A | topoisomerase (DNA) II alpha | 201291_s_at | 76.5 | Nucleus | enzyme | 7153 |
| T HELPER CELL DIFFERENTIATION | | | | | | |
| BCL6 | B-cell CLL/lymphoma 6 | 203140_at | 5.7 | Nucleus | transcription regulator | 604 |
| CD80 | CD80 molecule | 1555689_at | 18.46 | Plasma Membrane | transmembrane receptor | 941 |
| CD86 | CD86 molecule | 210895_s_at | 8.98 | Plasma Membrane | transmembrane receptor | 942 |
| CD40LG | CD40 ligand | 207892_at | 7.76 | Extracellular Space | cytokine | 959 |
| CXCR5 | C-X-C motif chemokine receptor 5 | 206126_at | 7.45 | Plasma Membrane | G-protein coupled receptor | 643 |
| HLA-DMB | major histocompatibility complex, class II, DM beta | 203932_at | 6.2 | Plasma Membrane | transmembrane receptor | 3109 |
| HLA-DQA1 | major histocompatibility complex, class II, DQ alpha 1 | 212671_s_at | 8.8 | Plasma Membrane | transmembrane receptor | 3117 |
| HLA-DQB1 | major histocompatibility complex, class II, DQ beta 1 | 212998_x_at | 6.55 | Plasma Membrane | other | 3119 |
| HLA-DRA | major histocompatibility complex, class II, DR alpha | 208894_at | 6.01 | Plasma Membrane | transmembrane receptor | 3122 |
| IFNGR1 | interferon gamma receptor 1 | 242903_at | 6.43 | Plasma Membrane | transmembrane receptor | 3459 |
| IL4 | interleukin 4 | 207539_s_at | 50.34 | Extracellular Space | cytokine | 3565 |
| IL5 | interleukin 5 | 207952_at | 153.37 | Extracellular Space | cytokine | 3567 |
| IL13 | interleukin 13 | 207844_at | 10.3 | Extracellular Space | cytokine | 3596 |
| IL12RB1 | interleukin 12 receptor subunit beta 1 | 206890_at | 5.34 | Plasma Membrane | transmembrane receptor | 3594 |
| IL12RB2 | interleukin 12 receptor subunit beta 2 | 206999_at | 5.88 | Plasma Membrane | transmembrane receptor | 3595 |
| IL21R | interleukin 21 receptor | 219971_at | 7.08 | Plasma Membrane | transmembrane receptor | 50615 |
| IL2RA | interleukin 2 receptor subunit alpha | 211269_s_at | 24.53 | Plasma Membrane | transmembrane receptor | 3559 |
| IL2RG | interleukin 2 receptor subunit gamma | 204116_al | 9.79 | Plasma Membrane | transmembrane receptor | 3561 |
| IL6ST | interleukin 6 signal transducer | 212196_at | 6.98 | Plasma Membrane | transmembrane receptor | 3572 |
| STAT1 | signal transducer and activator of transcription 1 | 200887_s_at | 6.22 | Nucleus | transcription regulator | 6772 |
| TGFB1 | transforming growth factor beta 1 | 203084_at | 8.15 | Extracellular Space | growth factor | 7040 |

TABLE 13-continued

Genes overexpressed in the T cells vs. PBMCs

| Symbol | Entrez Gene Name | Affymetrix | Exp Fold Change | Location | Type(s) | Entrez Gene ID for Human |
|---|---|---|---|---|---|---|
| TGFBR2 | transforming growth factor beta receptor 2 | 207334_s_at | 12.04 | Plasma Membrane | kinase | 7048 |

ARYL HYDROCARBON RECEPTOR SIGNALING

| Symbol | Entrez Gene Name | Affymetrix | Exp Fold Change | Location | Type(s) | Entrez Gene ID for Human |
|---|---|---|---|---|---|---|
| AHRR | aryl-hydrocarbon receptor repressor | 229354_at | 15.64 | Nucleus | other | 57491 |
| ALDH18A1 | aldehyde dehydrogenase 18 family member A1 | 217791_s_at | 7.36 | Cytoplasm | kinase | 5832 |
| ALDH6A1 | aldehyde dehydrogenase 6 family member A1 | 221590_s_at | 5.07 | Cytoplasm | enzyme | 4329 |
| BAX | BCL2 associated X, apoptosis regulator | 208478_s_at | 18.02 | Cytoplasm | transporter | 581 |
| CCNA1 | cyclin A1 | 205899_at | 5.2 | Nucleus | other | 8900 |
| CCNA2 | cyclin A2 | 203418_at | 134.53 | Nucleus | other | 890 |
| CCND3 | cyclin D3 | 1562028_at | 10.69 | Nucleus | other | 896 |
| CCNE2 | cyclin E2 | 205034_at | 7.41 | Nucleus | other | 9134 |
| CDK2 | cyclin dependent kinase 2 | 211804_s_at | 6.86 | Nucleus | kinase | 1017 |
| CDK4 | cyclin dependent kinase 4 | 202246_s_at | 5.09 | Nucleus | kinase | 1019 |
| CDK6 | cyclin dependent kinase 6 | 235287_at | 11.25 | Nucleus | kinase | 1021 |
| CHEK2 | checkpoint kinase 2 | 210416_s_at | 14.75 | Nucleus | kinase | 11200 |
| CYP1A1 | cytochrome P450 family 1 subfamily A member 1 | 205749_at | 5.98 | Cytoplasm | enzyme | 1543 |
| CYP1B1 | cytochrome P450 family 1 subfamily B member 1 | 202437_s_at | 13.89 | Cytoplasm | enzyme | 1545 |
| DHFR | dihydrofolate reductase | 202533_s_at | 119.7 | Nucleus | enzyme | 1719 |
| E2F1 | E2F transcription factor 1 | 204947_at | 6.82 | Nucleus | transcription regulator | 1869 |
| FAS | Fas cell surface death receptor | 216252_x_at | 7.81 | Plasma Membrane | transmembrane receptor | 355 |
| FOS | Fos proto-oncogene, AP-1 transcription factor subunit | 209189_at | 8.18 | Nucleus | transcription regulator | 2353 |
| GSTA4 | glutathione S-transferase alpha 4 | 202967_at | 11.95 | Cytoplasm | enzyme | 2941 |
| GSTM4 | glutathione S-transferase mu 4 | 204149_s_at | 11.02 | Cytoplasm | enzyme | 2948 |
| IL1B | interleukin 1 beta | 39402_at | 17.14 | Extracellular Space | cytokine | 3553 |
| JUN | Jun proto-oncogene, AP-1 transcription factor subunit | 201466_s_at | 6.07 | Nucleus | transcription regulator | 3725 |
| MGST2 | microsomal glutathione S-transferase 2 | 204168_at | 9.22 | Cytoplasm | enzyme | 4258 |
| MGST3 | microsomal glutathione S-transferase 3 | 201403_s_at | 10.44 | Cytoplasm | enzyme | 4259 |
| NQO1 | NAD(P)H quinone dehydrogenase 1 | 201467_s_at | 29.55 | Cytoplasm | enzyme | 1728 |
| NQO2 | NAD(P)H quinone dehydrogenase 2 | 203814_s_at | 5.95 | Cytoplasm | enzyme | 4835 |
| NRIP1 | nuclear receptor interacting protein 1 | 202600_s_at | 5.06 | Nucleus | transcription regulator | 8204 |
| POLA1 | DNA polymerase alpha 1, catalytic subunit | 204835_at | 10.84 | Nucleus | enzyme | 5422 |
| RARA | retinoic acid receptor alpha | 211605_s_at | 6.64 | Nucleus | ligand-dependent nuclear receptor | 5914 |
| TFDP1 | transcription factor Dp-1 | 212330_at | 10.29 | Nucleus | transcription regulator | 7027 |
| TGFB1 | transforming growth factor beta 1 | 203084_at | 8.15 | Extracellular Space | growth factor | 7040 |
| TGM2 | transglutaminase 2 | 201042_at | 14.73 | Cytoplasm | enzyme | 7052 |

CHK PROTEINS IN CELL CYCLE CHECKPOINT CONTROL

| Symbol | Entrez Gene Name | Affymetrix | Exp Fold Change | Location | Type(s) | Entrez Gene ID for Human |
|---|---|---|---|---|---|---|
| ANAPC11 | anaphase promoting complex subunit 11 | 226414_s_at | 5.53 | Cytoplasm | enzyme | 51529 |
| CCNB1 | cyclin B1 | 228729_at | 109.94 | Cytoplasm | kinase | 891 |
| CCNB2 | cyclin B2 | 202705_at | 129.25 | Cytoplasm | other | 9133 |
| CDC20 | cell division cycle 20 | 202870_s_at | 77.39 | Nucleus | other | 991 |
| CDC25A | cell division cycle 25A | 204695_at | 22.51 | Nucleus | phosphatase | 993 |
| CDC25C | cell division cycle 25C | 217010_s_at | 22.79 | Nucleus | phosphatase | 995 |
| CDK1 | cyclin dependent kinase 1 | 203213_at | 112.57 | Nucleus | kinase | 983 |
| CHEK2 | checkpoint kinase 2 | 210416_s_at | 14.75 | Nucleus | kinase | 11200 |
| ESPL1 | extra spindle pole bodies like 1, separase | 204817_at | 5.39 | Nucleus | peptidase | 9700 |
| FBXO5 | F-box protein 5 | 218875_s_at | 6.72 | Nucleus | enzyme | 26271 |
| KIF11 | kinesin family member 11 | 204444_at | 34.58 | Nucleus | other | 3832 |

TABLE 13-continued

Genes overexpressed in the T cells vs. PBMCs

| Symbol | Entrez Gene Name | Affymetrix | Exp Fold Change | Location | Type(s) | Entrez Gene ID for Human |
|---|---|---|---|---|---|---|
| KIF23 | kinesin family member 23 | 204709_s_at | 58.62 | Cytoplasm | other | 9493 |
| PLK2 | polo like kinase 2 | 201939_at | 13.28 | Nucleus | kinase | 10769 |
| PLK3 | polo like kinase 3 | 204958_at | 10.76 | Nucleus | kinase | 1263 |
| PLK4 | polo like kinase 4 | 204887_s_at | 13.84 | Cytoplasm | kinase | 10733 |
| PPM1L | protein phosphatase, Mg2+/Mn2+ dependent 1L | 228108_at | 6.25 | Cytoplasm | phosphatase | 151742 |
| PPP2R3B | protein phosphatase 2 regulatory subunit B"beta | 219264_s_at | 13.75 | Nucleus | phosphatase | 28227 |
| PRC1 | protein regulator of cytokinesis 1 | 218009_s_at | 6.28 | Nucleus | other | 9055 |
| PTTG1 | pituitary tumor-transforming 1 | 203554_x_at | 12.57 | Nucleus | transcription regulator | 9232 |
| TGFB1 | transforming growth factor beta 1 | 203084_at | 8.15 | Extracellular Space | growth factor | 7040 |
| ATAXIA-TELANGIECTASIA MUTATED (ATM) SIGNALING | | | | | | |
| BRCA1 | BRCA1, DNA repair associated | 204531_s_at | 79.8 | Nucleus | transcription regulator | 672 |
| CCNB1 | cyclin B1 | 228729_at | 109.94 | Cytoplasm | kinase | 891 |
| CCNB2 | cyclin B2 | 202705_at | 129.25 | Cytoplasm | other | 9133 |
| CDC25A | cell division cycle 25A | 204695_at | 22.51 | Nucleus | phosphatase | 993 |
| CDC25C | cell division cycle 25C | 217010_s_at | 22.79 | Nucleus | phosphatase | 995 |
| CDK1 | cyclin dependent kinase 1 | 203213_at | 112.57 | Nucleus | kinase | 983 |
| CDK2 | cyclin dependent kinase 2 | 211804_s_at | 6.86 | Nucleus | kinase | 1017 |
| CHEK2 | checkpoint kinase 2 | 210416_s_at | 14.75 | Nucleus | kinase | 11200 |
| GADD45B | growth arrest and DNA damage inducible beta | 209304_x_at | 5.72 | Cytoplasm | other | 4616 |
| JUN | Jun proto-oncogene, AP-1 transcription factor subunit | 201466_s_at | 6.07 | Nucleus | transcription regulator | 3725 |
| RAD50 | RAD50 double strand break repair protein | 208393_s_at | 8.4 | Nucleus | enzyme | 10111 |
| RAD51 | RAD51 recombinase | 205024_s_at | 28.78 | Nucleus | enzyme | 5888 |
| RBBP8 | RB binding protein 8, endonuclease | 203344_s_at | 9.37 | Nucleus | enzyme | 5932 |
| SMC2 | structural maintenance of chromosomes 2 | 204240_s_at | 41.75 | Nucleus | transporter | 10592 |
| ZEB1 | zinc finger E-box binding homeobox 1 | 212758_s_at | 5.16 | Nucleus | transcription regulator | 6935 |
| ZNF420 | zinc finger protein 420 | 238937_at | 5.07 | Cytoplasm | other | 147923 |
| NF-κB ACTIVATION BY VIRUS | | | | | | |
| CXCR5 | C-X-C motif chemokine receptor 5 | 206126_at | 7.45 | Plasma Membrane | G-protein coupled receptor | 643 |
| FGFR1 | fibroblast growth factor receptor 1 | 210973_s_at | 5.49 | Plasma Membrane | kinase | 2260 |
| IRS2 | insulin receptor substrate 2 | 209184_s_at | 7 | Cytoplasm | enzyme | 8660 |
| ITGA1 | integrin subunit alpha 1 | 214660_at | 5.14 | Plasma Membrane | other | 3672 |
| ITGA4 | integrin subunit alpha 4 | 243366_s_at | 12.85 | Plasma Membrane | transmembrane receptor | 3676 |
| ITGA5 | integrin subunit alpha 5 | 201389_at | 7.35 | Plasma Membrane | transmembrane receptor | 3678 |
| ITGA6 | integrin subunit alpha 6 | 201656_at | 5.16 | Plasma Membrane | transmembrane receptor | 3655 |
| ITGAL | integrin subunit alpha L | 1554240_a_at | 5.11 | Plasma Membrane | transmembrane receptor | 3683 |
| ITGB1 | integrin subunit beta 1 | 1553530_a_at | 5.18 | Plasma Membrane | transmembrane receptor | 3688 |
| PIK3C2A | phosphatidylinositol-4-phosphate 3-kinase catalytic subunit type 2 alpha | 241905_at | 6.37 | Cytoplasm | kinase | 5286 |
| PIK3CA | phosphatidylinositol-4,5-bisphosphate 3-kinase catalytic subunit alpha | 204369_at | 6.08 | Cytoplasm | kinase | 5290 |

TABLE 13-continued

Genes overexpressed in the T cells vs. PBMCs

| Symbol | Entrez Gene Name | Affymetrix | Exp Fold Change | Location | Type(s) | Entrez Gene ID for Human |
|---|---|---|---|---|---|---|
| PRKD3 | protein kinase D3 | 242549_at | 5.7 | Nucleus | kinase | 23683 |
| RRAS | related RAS viral (r-ras) oncogene homolog | 212647_at | 12.45 | Cytoplasm | enzyme | 6237 |
| SUPERPATHWAY OF SERINE AND GLYCINE BIOSYNTHESIS | | | | | | |
| PHGDH | phosphoglycerate dehydrogenase | 201397_at | 7.01 | Cytoplasm | enzyme | 26227 |
| PSAT1 | phosphoserine aminotransferase 1 | 223062_s_at | 81.37 | Cytoplasm | enzyme | 29968 |
| PSPH | phosphoserine phosphatase | 205194_at | 24.17 | Cytoplasm | phosphatase | 5723 |
| SHMT1 | serine hydroxymethyltransferase 1 | 209980_s_at | 23.92 | Cytoplasm | enzyme | 6470 |
| SHMT2 | serine hydroxymethyltransferase 2 | 214437_s_at | 10.33 | Cytoplasm | enzyme | 6472 |
| ENDOCYTIC PATHWAYS LINKED WITH VIRAL ENTRY | | | | | | |
| ACTA2 | actin, alpha 2, smooth muscle, aorta | 200974_at | 5.58 | Cytoplasm | other | 59 |
| AP2B1 | adaptor related protein complex 2 beta 1 subunit | 200615_s_at | 12.33 | Plasma Membrane | transporter | 163 |
| CXADR | coxsackie virus and adenovirus receptor | 226374_at | 5.21 | Plasma Membrane | transmembrane receptor | 1525 |
| FGFR1 | fibroblast growth factor receptor 1 | 210973_s_at | 5.49 | Plasma Membrane | kinase | 2260 |
| FYN | FYN proto-oncogene, Src family tyrosine kinase | 1559101_at | 11.42 | Plasma Membrane | kinase | 2534 |
| IRS2 | insulin receptor substrate 2 | 209184_s_at | 7 | Cytoplasm | enzyme | 8660 |
| ITGA1 | integrin subunit alpha 1 | 214660_at | 5.14 | Plasma Membrane | other | 3672 |
| ITGA4 | integrin subunit alpha 4 | 243366_s_at | 12.85 | Plasma Membrane | transmembrane receptor | 3676 |
| ITGA5 | integrin subunit alpha 5 | 201389_at | 7.35 | Plasma Membrane | transmembrane receptor | 3678 |
| ITGA6 | integrin subunit alpha 6 | 201656_at | 5.16 | Plasma Membrane | transmembrane receptor | 3655 |
| ITGAL | integrin subunit alpha L | 1554240_a_at | 5.11 | Plasma Membrane | transmembrane receptor | 3683 |
| ITGB1 | integrin subunit beta 1 | 1553530_a_at | 5.18 | Plasma Membrane | transmembrane receptor | 3688 |
| ITGB7 | integrin subunit beta 7 | 205718_at | 6.63 | Plasma Membrane | transmembrane receptor | 3695 |
| PIK3C2A | phosphatidylinositol-4-phosphate 3-kinase catalytic subunit type 2 alpha | 241905_at | 6.37 | Cytoplasm | kinase | 5286 |
| PIK3CA | phosphatidylinositol-4,5-bisphosphate 3-kinase catalytic subunit alpha | 204369_at | 6.08 | Cytoplasm | kinase | 5290 |
| PRKD3 | protein kinase D3 | 242549_at | 5.7 | Nucleus | kinase | 23683 |
| RAC2 | ras-related C3 botulinum toxin substrate 2 (rho family, small GTP binding protein Rac2) | 207419_s_at | 10.13 | Cytoplasm | enzyme | 5880 |
| RAC3 | ras-related C3 botulinum toxin substrate 3 (rho family, small GTP binding protein Rac3) | 206103_at | 6.24 | Cytoplasm | enzyme | 5881 |
| RRAS | related RAS viral (r-ras) oncogene homolog | 212647_at | 12.45 | Cytoplasm | enzyme | 6237 |
| COLANIC ACID BIOSYNTHESIS | | | | | | |
| GALK1 | galactokinase 1 | 204374_s_at | 30.31 | Cytoplasm | kinase | 2584 |
| GALK2 | galactokinase 2 | 205219_s_at | 5.7 | Cytoplasm | kinase | 2585 |
| GMDS | GDP-mannose 4,6-dehydratase | 204875_s_at | 7.34 | Cytoplasm | enzyme | 2762 |
| GMPPA | GDP-mannose pyrophosphorylase A | 218070_s_at | 5.74 | Cytoplasm | enzyme | 29926 |
| TSTA3 | tissue specific transplantation antigen P35B | 201644_at | 5.26 | Plasma Membrane | enzyme | 7264 |

TABLE 13-continued

Genes overexpressed in the T cells vs. PBMCs

| Symbol | Entrez Gene Name | Affymetrix | Exp Fold Change | Location | Type(s) | Entrez Gene ID for Human |
|---|---|---|---|---|---|---|
| UGDH | UDP-glucose 6-dehydrogenase | 203343_at | 10.71 | Nucleus | enzyme | 7358 |
| LINOLENATE BIOSYNTHESIS | | | | | | |
| ACSL5 | acyl-CoA synthetase long-chain family member 5 | 222592_s_at | 7.34 | Cytoplasm | enzyme | 51703 |
| ACSL6 | acyl-CoA synthetase long-chain family member 6 | 229725_at | 6.49 | Cytoplasm | enzyme | 23305 |
| CYB5A | cytochrome b5 type A | 215726_s_at | 7.26 | Cytoplasm | enzyme | 1528 |
| FADS1 | fatty acid desaturase 1 | 208962_s_at | 35.99 | Plasma Membrane | enzyme | 3992 |
| FADS2 | fatty acid desaturase 2 | 202218_s_at | 25.1 | Plasma Membrane | enzyme | 9415 |
| SLC27A2 | solute carrier family 27 member 2 | 205768_s_at | 27.09 | Cytoplasm | transporter | 11001 |
| AGRANULOCYTE ADHESION AND DIAPEDESIS | | | | | | |
| ACTA2 | actin, alpha 2, smooth muscle, aorta | 200974_at | 5.58 | Cytoplasm | other | 59 |
| C5 | complement component 5 | 205500_at | 6.47 | Extracellular Space | cytokine | 727 |
| CCL4 | C-C motif chemokine ligand 4 | 204103_at | 6.29 | Extracellular Space | cytokine | 6351 |
| CCL13 | C-C motif chemokine ligand 13 | 206407_s_at | 5.68 | Extracellular Space | cytokine | 6357 |
| CCL17 | C-C motif chemokine ligand 17 | 207900_at | 25.39 | Extracellular Space | cytokine | 6361 |
| CCL18 | C-C motif chemokine ligand 18 | 209924_at | 21.71 | Extracellular Space | cytokine | 6362 |
| CCL20 | C-C motif chemokine ligand 20 | 205476_at | 18.69 | Extracellular Space | cytokine | 6364 |
| CCL22 | C-C motif chemokine ligand 22 | 207861_at | 20.55 | Extracellular Space | cytokine | 6367 |
| CKLF | chemokine-like factor | 223451_s_at | 30.79 | Extracellular Space | cytokine | 51192 |
| CXCL2 | C-X-C motif chemokine ligand 2 | 209774_x_at | 94.66 | Extracellular Space | cytokine | 2920 |
| CXCL8 | C-X-C motif chemokine ligand 8 | 202859_x_at | 27.39 | Extracellular Space | cytokine | 3576 |
| CXCL16 | C-X-C motif chemokine ligand 16 | 223454_at | 7.09 | Extracellular Space | cytokine | 58191 |
| FN1 | fibronectin 1 | 211719_x_at | 14.42 | Extracellular Space | enzyme | 2335 |
| IL1B | interleukin 1 beta | 39402_at | 17.14 | Extracellular Space | cytokine | 3553 |
| ITGA1 | integrin subunit alpha 1 | 214660_at | 5.14 | Plasma Membrane | other | 3672 |
| ITGA4 | integrin subunit alpha 4 | 243366_s_at | 12.85 | Plasma Membrane | transmembrane receptor | 3676 |
| ITGA5 | integrin subunit alpha 5 | 201389_at | 7.35 | Plasma Membrane | transmembrane receptor | 3678 |
| ITGA6 | integrin subunit alpha 6 | 201656_at | 5.16 | Plasma Membrane | transmembrane receptor | 3655 |
| ITGB1 | integrin subunit beta 1 | 1553530_a_at | 5.18 | Plasma Membrane | transmembrane receptor | 3688 |
| ITGB7 | integrin subunit beta 7 | 205718_at | 6.63 | Plasma Membrane | transmembrane receptor | 3695 |
| JAM3 | junctional adhesion molecule 3 | 212813_at | 12.14 | Plasma Membrane | other | 83700 |
| MMP25 | matrix metallopeptidase 25 | 207890_s_at | 13.29 | Plasma Membrane | peptidase | 64386 |
| MYL6B | myosin light chain 6B | 204173_at | 11.23 | Cytoplasm | other | 140465 |
| SDC4 | syndecan 4 | 202071_at | 5.93 | Plasma Membrane | other | 6385 |
| SELPLG | selectin P ligand | 209880_s_at | 9.3 | Plasma Membrane | other | 6404 |
| XCL1 | X-C motif chemokine ligand 1 | 206366_x_at | 18.61 | Extracellular Space | cytokine | 6375 |

TABLE 13-continued

Genes overexpressed in the T cells vs. PBMCs

| Symbol | Entrez Gene Name | Affymetrix | Exp Fold Change | Location | Type(s) | Entrez Gene ID for Human |
|---|---|---|---|---|---|---|
| XCL2 | X-C motif chemokine ligand 2 | 214567_s_at | 24.97 | Extracellular Space | cytokine | 6846 |
| CAVEOLAE-MEDIATED ENDOCHE SIGNALING | | | | | | |
| ACTA2 | actin, alpha 2, smooth muscle, aorta | 200974_at | 5.58 | Cytoplasm | other | 59 |
| COPG2 | coatomer protein complex subunit gamma 2 | 223457_at | 5.24 | Cytoplasm | transporter | 26958 |
| FLOT1 | flotillin 1 | 208748_s_at | 21.43 | Plasma Membrane | other | 10211 |
| FYN | FYN proto-oncogene, Src family tyrosine kinase | 1559101_at | 11.42 | Plasma Membrane | kinase | 2534 |
| ITGA1 | integrin subunit alpha 1 | 214660_at | 5.14 | Plasma Membrane | other | 3672 |
| ITGA4 | integrin subunit alpha 4 | 243366_s_at | 12.85 | Plasma Membrane | transmembrane receptor | 3676 |
| ITGA5 | integrin subunit alpha 5 | 201389_at | 7.35 | Plasma Membrane | transmembrane receptor | 3678 |
| ITGA6 | integrin subunit alpha 6 | 201656_at | 5.16 | Plasma Membrane | transmembrane receptor | 3655 |
| ITGAL | integrin subunit alpha L | 1554240_a_at | 5.11 | Plasma Membrane | transmembrane receptor | 3683 |
| ITGAX | integrin subunit alpha X | 210184_at | 9.34 | Plasma Membrane | transmembrane receptor | 3687 |
| ITGB1 | integrin subunit beta 1 | 1553530_a_at | 5.18 | Plasma Membrane | transmembrane receptor | 3688 |
| ITGB7 | integrin subunit beta 7 | 205718_at | 6.63 | Plasma Membrane | transmembrane receptor | 3695 |
| MAP3K2 | mitogen-activated protein kinase kinase kinase 2 | 227073_at | 5.83 | Cytoplasm | kinase | 10746 |

In a separate experiment, ten lines of HPV T cell and process control cells (T cells not exposed to an HPV PepMix) were generated using PBMC from 10 healthy donors. Pan T cells were purified from HPV T cell, process control cells and their donor matched PBMCs. RNA extraction from the 30 samples was performed. The gene expression profile of the purified T cells was characterized by using Affymetrix U133A Plus 2.0 array. The fold changes of gene expression were obtained by normalization with housekeeping genes (beta-2-microglobulin (B2M), hypoxanthine phosphoribosyltransferase (HPRT), and Large Ribosomal Protein (RPLPO)) followed by comparison of expression levels between samples. Thousands of genes were differentially expressed in HPV T cell compared to their matched PBMCs and/or process control cells. Six of the differentially expressed genes were chosen to be validated by quantitative real-time PCR with TaqMan gene expression assays. As a comparator, unpulsed T cells (that is, T cells generated in the absence of HPV16 and HPV18 E6 and E7 proteins) were used. In this experiment, six differentially-expressed genes were identified: CCL18 (chemokine (C-C motif) Ligand 18); CH13L1 (Chitinase-3-like protein); FN1 (Fibronectin 1); LYZ (Lysozyme); RCHY1 (Ring finger and CHY zinc finger 1); and PALLD (Palladin, cytoskeletal associated protein). CCL18, CHI3L1, FN1 and PALLD were significantly (at least 5-fold) up-regulated in the HPV T cell population, and LYZ and RCHY1 were down-regulated significantly (at least 5-fold), as compared to that in control unpulsed T cells from their matched donors.

6.10 Example 10: ELISPOT Assay for T Cells in Patient PBMC Samples

This Example describes an assay to quantify HPV-specific T cells in patient PBMC samples. The assay may also be used to reveal frequencies and cytokine signatures of antigen-specific T cells, e.g., cytotoxic T lymphocytes, and to quantify antigen-specific T cells in response to HPV antigen stimulation in PBMC.

Materials: Cryopreserved PBMCs from patients; phosphate-buffered saline (PBS), pH7.2 (Invitrogen, Cat #20012027); Tween-20 (Sigma, Cat #P2287); RPMI 1640 Medium (ATCC, Cat #ATCC30-2001); human IFN-γ ELISPOT set (BD Biosciences, Cat #551849)—set components: 51-2555KC Purified NA/LE Anti-Human IFN-γ; 51-1890KC Biotinylated Anti-Human IFN-γ; 51-2447KC BD ELISPOT Plates; and 51-9000209 Streptavidin-HRP; BD™ AEC Substrate Reagent Set (BD Biosciences, Cat #551951); CTL Anti-Aggregate Wash™ Medium (CTL, Cat #CTL-AA-005); CTL-Test Plus Medium (CTL, Cat #CTLTP-005); and human AB serum (Sigma, Cat #:H3667-100ML).

Antigens: A TAA antigen solution is made into 100 ug/ml each in distilled water using equal amounts of PepTivator HPV16E6 (Miltenyi, Cat #130-095-998); PepTivator HPV16E7 (Miltenyi, Cat #130-096-000); PepTivator HPV18E6 (Miltenyi, Cat #130-096-006); PepTivator HPV18E7 (Miltenyi, Cat #130-096-007).

Equipment: ViCell (Beckman Coulter, Fullerton, CA); AID EliSpot Reader (AID GmbH, Strassberg, Germany).

Preparation of medium and buffer. Coating Buffer: capture antibody stock is diluted at 1:200 in PBS (Stock: Purified NA/LE Anti-Human IFNγ, 1 mg/ml). Blocking Buffer: 5% v/v human AB serum is prepared in RPMI1640. Wash Buffer I: 1×PBS containing 0.05% Tween-20 is prepared, e.g., by adding 0.5 ml Tween-20 into 1 L PBS. Wash Buffer II: 1x PBS. Dilution Buffer: 1×PBS containing 5% human AB serum. Substrate Solution: No more than 15 minutes prior to use, one drop (200) of AEC chromogen is mixed with each 1 ml of AEC substrate, and mixed thoroughly.

Experiment procedures: Capture antibodies specific for IFNγ are coated onto a 96-well PVDF plate as follows. Coating buffer is prepared by diluting capture antibody stock at 1:200 in PBS (Stock: Purified NA/LE Anti-Human IFNγ, 1 mg/ml). Plates are coated by adding 100 μl of coating buffer to each well of the 96 well plate. The plate is then stored at 4° C. overnight. The plate is then blocked with blocking buffer. Blocking buffer is prepared as 5% Human AB serum in RPMI1640, e.g., by adding 25 ml of human AB serum into 475 ml of RPMI1640. Excess coating antibody is discarded. 200 μl/well Blocking Solution is added to each well and incubated for 2 hours at room temperature.

Cells are then activated with HPV antigen. Plate antigen solution: HPV antigen is diluted into CTL-Test Plus medium at 2 μg/ml, for example, to make 5 ml antigen solution by adding 25 ul antigen stock solution into 5 ml of medium. The blocking buffer is decanted, and 50 μl of antigen solution is added into each well of the 96 well plate, and the plate is incubated at 37° C. for 10-20 minutes before plating cells. PBMCs are plated by thawing the PBMCs in a 50 ml of conical tube, and diluting the cells by slowly adding pre-warmed 37° C. Anti-Aggregate medium. The PBMCs are centrifuged for 5 min at 400 g, the supernatant is decanted, and the resulting cell pellet is resuspended into anti-Aggregate medium. Cell number is determined using the ViCell. PBMC are centrifuged and resuspended into CTL-Test Plus medium at 20 million cells per ml. 1.5-fold serial dilution of PBMC suspension from the highest concentration are made in a new U bottom 96 well plate, as indicated in Table 14 below. Each cell concentration is preferably performed in triplicate.

TABLE 14

Serial dilution of PBMC suspension

| PBMC number/50 ul | Medium volume (ul) | PBMC volume of serial dilution | Dilution |
|---|---|---|---|
| 0.75 | 0 | 180 | 1.5fold |
| 0.50 | 60 | 120 | serial |
| 0.33 | 60 | 120 | dilution |
| 0.22 | 60 | 120 | |
| 0.15 | 60 | 120 | |
| 0.10 | 60 | 120 | |
| 0.07 | 60 | 120 | |
| 0.04 | 60 | 120 | |

50 μl of PBMC in a different density is transferred to the assay plate immediately placed into a 37° C. incubator. The plates are then incubated for 48 hours without disturbance. Captured cytokine (IFNAγ) is detected using biotinylated anti-human IFNγ (detection antibody). The cell suspension is aspirated, the wells washed 2× with deionized water, and 3× with 200 μl/well wash buffer I. 1:250 detection antibody is prepared in dilution buffer to make 2 μg/ml detection antibody solution, by adding 400 μl of 0.5 mg/ml detection antibody stock into 100 ml of dilution buffer. 100 μl is added per well and incubated for 2 h at room temperature.

Secreted cytokine is visualized by color development using 1:100 enzyme conjugate (Streptavidin-HRP) in Dilution Buffer, adding 100 μl/well diluted enzyme reagent, and incubating for 1 hour at room temperature. The enzyme conjugate solution is then discarded and the wells washed 4× with 200 μl/well wash buffer I, and 2× with 200 μl/well Wash Buffer II. 1000 of Final Substrate Solution is then added to each well, and color development is monitored from 5-60 min. The reaction is stopped by washing wells with DI water, and the plates are air-dried until completely dry. The resulting spots are enumerated with an AID EliSpot Reader with IFNγ spot reader program selected according to manufacturer instructions.

6.11 Example 11: Clinical Study Protocol

This Example describes a phase 1, multicenter, open-label, dose-escalating safety study of human peripheral blood-derived, culture expanded, autologous, T cell infusion in subjects with HPV+ recurrent and/or metastatic squamous cell carcinoma of the head and neck (SCCHN) following first-line chemotherapy with or without radiation therapy.

First-line therapy for the purposes of this study is the first treatment administered for the diagnosis of recurrent disease or metastatic disease. The study enrolls up to 84 subjects. The study consists of a Pre Standard of Care Screening Period, a Standard of Care Treatment Period, a T cell Screening Period, a T cell Treatment Period (Day −4 to Day 0), which includes a 3-day conditioning treatment (Day −4 to Day −2), and a T cell infusion on Day 0, and a Follow-up Period beginning on Day 1 to the time of progressive disease (PD). A Long Term Follow-up Period starts after PD or start of new therapy and includes collection of information for survival and additional therapies administered for SCCHN every three months until death, loss to follow-up, or withdrawal of consent, whichever occurs first. The anticipated participation time for subjects is five years.

Subjects have recurrent and/or metastatic oropharyngeal cancer that is p16 and/or HPV-16 and/or HPV-18 positive as determined by immunohistochemistry, polymerase chain reaction, or ribonuclic acid fluorescence in situ hybridization.

The primary objective of the study is to assess the safety and determine the maximum tolerated dose (MTD) of the T cells administered intravenously (IV) in subjects with HPV+ recurrent and/or metastatic SCCHN as defined by National Comprehensive Cancer Network (NCCN) guidelines.

The secondary objectives of the study are to explore potential clinical efficacy by assessing tumor response as measured by the Response Evaluation Criteria in Solid Tumors (RECIST v1.1) guidelines, and by assessing duration and rate of disease control, progression-free survival (PFS) and overall survival (OS), and to evaluate the tolerability of the pre-specified lymphodepletion regimens as measured by safety.

The study investigates up to 5 dose-level cohorts utilizing a low cyclophosphamide (LD-Cy) only regimen for lymphodepletion. Once the MTD of the T cells is identified, two alternative lymphodepletion regimens are investigated, high dose cyclophosphamide (HD-Cy) and cyclophosphamide and fludarabine (Cy-Flu).

Subjects undergo leukapheresis for the purposes of manufacturing T cells. After the subject undergoes leukapheresis, the subject receives front-line therapy as medically indicated, at the discretion of the treating physician, for example, subjects may receive up to 6 cycles of chemotherapy following standard of care practices. During front-line therapy, the subject undergoes clinical and radiological disease evaluation by the treating physician. Based on the totality of the data treating physician may advise the sponsor to proceed with T cell manufacturing for the subject.

Subject-specific T cells are then manufactured, tested and released for use over the course of approximately 28 days. T cell manufacturing is performed according to the methods described herein. Once the T cells are successfully manufactured and released for use, the subject may initiate treatment, the timing of which is at the discretion of the treating physician, but takes place after front-line chemotherapy is completed. In order to accommodate variances in length of first-line therapy and the possibility of early progression, subjects may be enrolled to the study for leukapheresis without a known date of T cell treatment.

The study enrolls up to a maximum of 84 T cell-treated subjects. No fewer than 3 dose-limiting toxicity (DLT)-evaluable subjects are investigated at each dose level cohort prior to any recommendation for dose escalation. In the event of the DLT, the cohort is expanded and no fewer than 6 DLT-evaluable subjects are investigated prior to dose level cohort escalation. In the event that 2 DLTs occur, enrollment to that specific cohort is halted at which time MTD recommendation is evaluated. Due to the variability of duration of first-line therapy, and the possibility of subjects not being treated with T cells, no more than 18 subjects may undergo leukapheresis without treatment of T cells or early termination at any given time during the escalation phase of the study. Once the conditioning regimen and MTD of T cells is identified, an 18 subject expansion is enrolled to provide additional safety information and contribute to additional efficacy data.

The T cell treatment period starts with a three day lymphodepletion regimen starting on Day −4 to Day −2. Initially a single agent regimen is utilized, specifically LD-Cy which includes cyclophosphamide at 300 mg/m$^2$/day administered on Day −4 to −2. T cells are administered on Day 0. Each subject receives a single dose of T cells, which may require multiple infusion bags.

Subjects are sequentially assigned to one of up to five dosing cohorts, based on time of entry into the study:
Dose Level 1: $5.0 \times 10^7$ cells/m$^2$
Dose Level 2: $1.5 \times 10^8$ cells/m$^2$
Dose Level 3: $4.5 \times 10^8$ cells/m$^2$
Dose Level 4: $1.3 \times 10^9$ cells/m$^2$
Dose Level 5: $2.0 \times 10^9$ cells/m$^2$ Once the MTD for the T cells is identified, two alternative lymphodepletion regimens are investigated in parallel based on time of treatment period entry. HD-Cy, which includes Cyclophosphamide at a higher dose of 900 mg/m$^2$/day for three days starting on Day −4 to −2, or Cy-Flu, which includes cyclophosphamide 300 mg/m$^2$/day for three days in combination with fludarabine 30 mg/kg/day for two days starting Day −4 to Day −3.

Subjects are pre-medicated with acetaminophen 650 mg orally (PO) and diphenhydramine 25 mg (PO/IV/intramuscularly [IM]) before and approximately 4 hours after the T cell infusion. Subjects are monitored for at least 24 hours post end of T cell infusion.

The decision to increase the size of the cohort is based upon the number of DLT events. For the first cohort, not more than 1 subject may begin treatment in any 14 day period.

Subjects are closely monitored for adverse reactions throughout the administration of the study treatment regimen. If adverse events (AEs) occur during the T cell infusion, with the potential of becoming severe (defined as National Cancer Institute [NCI]) common terminology criteria for adverse events [CTCAE]) Version 4.03 Grade 3 or above; or urgent intervention indicated to prevent increase in severity with the potential of becoming life threatening), the infusion is stopped and subjects continue to be followed.

After completion of the T cell administration, subjects are followed until PD. Thereafter, subjects are followed for survival until death, loss to follow up, or withdrawal of consent, whichever occurs first.

EQUIVALENTS

The present disclosure is not to be limited in scope by the specific embodiments described herein. Indeed, various modifications of the subject matter provided herein, in addition to those described, will become apparent to those skilled in the art from the foregoing description. Such modifications are intended to fall within the scope of the appended claims.

Various publications, patents and patent applications are cited herein, the disclosures of which are incorporated by reference in their entireties.

What is claimed is:

1. A method of producing a cell population comprising antigen-specific T cells, comprising the steps of:
   (a) isolating peripheral blood mononuclear cells (PBMCs) from a subject;
   (b) culturing said PBMCs in an antigen presenting cell (APC) induction medium comprising interleukin 4 (IL-4) and soluble CD40 ligand (sCD40L) and/or comprising granulocyte-macrophage colony-stimulating factor (GM-CSF) and interferon α (IFN-α), to produce a first population of cells, wherein the first population of cells comprises T cells;
   (c) culturing the first population of cells in the presence of one or more antigens, to produce a second population of cells; and
   (d) culturing the second population of cells in a T cell expansion medium comprising interleukin 7 (IL-7), interleukin 15 (IL-15), and IL-4, to produce a third population of cells;
   wherein the third population of cells comprises T cells that are CD3+ and are specific for an antigen added in step (c), and
   wherein all of the T cells of the third population of cells that are CD3+ and are specific of the antigen added in step (c) are derived from the T cells of the first population of cells.

2. The method of claim 1, wherein the third population of cells comprises T cells that are CD4+, CD8+, or CD4+ and CD8+.

3. The method of claim 1, wherein the antigen-specific T cells are cytotoxic T lymphocytes (CTLs).

4. The method of claim 1, wherein the APC induction medium comprises IL-4 and sCD40L.

5. The method of claim 4, wherein the APC induction medium further comprises synthetic oligonucleotides with unmethylated CpG dinucleotide motifs.

6. The method of claim 5, wherein the APC induction medium further comprises GM-CSF and IFN-α.

7. The method of claim 1, further comprising a step of culturing the third population of cells in a second T cell expansion medium comprising IL-7 and IL-15, but not comprising IL-4, to create a fourth population of cells; wherein the fourth population of cells comprises T cells that are CD$^{3+}$ and specific for an antigen added in step (c).

8. The method of claim 7, wherein the second T cell expansion medium comprises 40-60 ng/mL of IL-7 and 7-11 ng/mL of IL-15.

9. The method of claim 1, wherein the one or more antigens is one or more tumor-associated antigens or virus-associated antigens.

10. The method of claim 1, wherein the one or more antigens is one or more human papillomavirus (HPV)-associated antigens.

11. The method of claim 1, wherein the one or more antigens is a pool of peptides.

12. The method of claim 11, wherein the pool of peptides cover the sequences of one or more of human HPV16E6, HPV16E7, HPV18E6, and HPV18E7 proteins.

13. The method of claim 11, wherein the pool of peptides cover the complete sequence of human HPV16E6, HPV16E7, HPV18E6, and HPV18E7 proteins.

14. The method of claim 11, wherein the pool of peptides are at a concentration of 1 μg/mL.

15. The method of claim 1, wherein the APC induction medium comprises 8-12 ng/mL of IL-4 and 0.8-1.2 μg/mL of sCD40L.

16. The method of claim 1, wherein the T cell expansion medium comprises 40-60 ng/mL of IL-7, 7-11 ng/mL of IL-15, and 45-65 ng/mL of IL-4.

17. The method of claim 1, wherein the duration of step (b) is 1-3 days.

18. The method of claim 1, wherein the PBMCs are isolated from whole blood, buffy coat, or an enriched leukapheresis product.

19. The method of claim 1, further comprising a step of isolating T cells that are $CD^{3+}$ from the third population of cells or the fourth population of cells.

20. The method of claim 1, wherein the antigen-specific CD3+ cells are identified by intracellular cytokine staining (ICCS).

21. The method of claim 1, wherein step (c) is performed in APC induction medium.

22. The method of claim 1, wherein the culturing steps are performed in a gas-permeable enclosure.

23. The method of claim 1, wherein the APC induction medium comprises GM-CSF and IFN-α.

24. The method of claim 1, wherein the duration of step (d) is 8-16 days.

25. The method of claim 1, wherein the PBMCs are seeded in the APC induction medium at a density of 4-6× $10^6/cm^2$.

* * * * *